(12) United States Patent
Bayat et al.

(10) Patent No.: US 11,026,775 B2
(45) Date of Patent: *Jun. 8, 2021

(54) TEXTURED SURFACES FOR BREAST IMPLANTS

(71) Applicant: Establishment Labs S.A., Alajuela (CR)

(72) Inventors: Ardeshir Bayat, Manchester (GB); Ernie Hill, Manchester (GB); Daniel Kyle, Sunderland (GB); Antonios Oikonomou, Manchester (GB)

(73) Assignee: Establishment Labs S.A., Alajuela (CR)

( * ) Notice: Subject to any disclaimer, the term of this patent is extended or adjusted under 35 U.S.C. 154(b) by 0 days.

This patent is subject to a terminal disclaimer.

(21) Appl. No.: 16/784,479

(22) Filed: Feb. 7, 2020

(65) Prior Publication Data

US 2020/0188078 A1    Jun. 18, 2020

Related U.S. Application Data

(63) Continuation of application No. 15/119,264, filed as application No. PCT/GB2015/050438 on Feb. 16, 2015, now Pat. No. 10,595,979.

(30) Foreign Application Priority Data

Feb. 17, 2014   (GB) ..................... 1402804

(51) Int. Cl.
*A61F 2/00* (2006.01)
*A61F 2/12* (2006.01)
(Continued)

(52) U.S. Cl.
CPC .............. *A61F 2/0077* (2013.01); *A61F 2/12* (2013.01); *G03F 7/0037* (2013.01);
(Continued)

(58) Field of Classification Search
CPC .. A61F 2/0077; A61F 2/12; A67F 2002/0081; A67F 2002/0086
See application file for complete search history.

(56) References Cited

U.S. PATENT DOCUMENTS 3,761,047 A   9/1973 Mao
4,533,568 A   8/1985 McClinton et al.
(Continued)

FOREIGN PATENT DOCUMENTS

EP   0850604 A2   7/1998
JP   H0978102 A   3/1997
(Continued)

OTHER PUBLICATIONS

Barnsley, G.P. et al., "Textured surface breast implants in the prevention of capsular contracture among breast augmentation patients: a meta-analysis of randomized controlled trials," *Plast. Reconstr. Surg.*, vol. 117, No. 7, pp. 2182-2190 (2006), abstract only.

(Continued)

*Primary Examiner* — Joanna Pleszczynska
(74) *Attorney, Agent, or Firm* — Bookoff McAndrews, PLLC

(57) ABSTRACT

The invention provides new devices for implantation in a patient having irregular textured surfaces, which devices show significantly improved cellular response compared to conventional smooth and textured implants, indicating that significantly improved biocompatibility would be achieved in vivo. Methods for making such new devices and surface textures are also disclosed.

20 Claims, 68 Drawing Sheets

Specification includes a Sequence Listing.

(51) Int. Cl.

| | | |
|---|---|---|
| *G03F 7/00* | (2006.01) | |
| *H01J 37/305* | (2006.01) | |
| *B29C 64/112* | (2017.01) | |
| *B33Y 10/00* | (2015.01) | |
| *B33Y 80/00* | (2015.01) | |
| *B29K 83/00* | (2006.01) | |
| *B29L 31/00* | (2006.01) | |

(52) U.S. Cl.
CPC ... *H01J 37/3056* (2013.01); *A61F 2002/0081* (2013.01); *A61F 2002/0086* (2013.01); *A61F 2240/004* (2013.01); *B29C 64/112* (2017.08); *B29K 2083/00* (2013.01); *B29L 2031/7532* (2013.01); *B33Y 10/00* (2014.12); *B33Y 80/00* (2014.12); *H01J 2237/3174* (2013.01)

(56) References Cited

U.S. PATENT DOCUMENTS

| | | |
|---|---|---|
| 9,808,338 B2 | 11/2017 | Schuessler et al. |
| 2002/0119177 A1 | 8/2002 | Bowman et al. |
| 2004/0148024 A1 | 7/2004 | Williams |
| 2004/0162613 A1 | 8/2004 | Roballey |
| 2006/0219143 A1 | 10/2006 | Brennan et al. |
| 2009/0088858 A1* | 4/2009 | Zinger ............... C23G 1/106 623/18.11 |
| 2010/0016989 A1 | 1/2010 | Lyngstadaas et al. |
| 2010/0114303 A1 | 5/2010 | Su et al. |
| 2010/0226943 A1 | 9/2010 | Brennan et al. |
| 2011/0276134 A1 | 11/2011 | Manesis et al. |
| 2012/0165934 A1 | 6/2012 | Schuessler |
| 2013/0110243 A1 | 5/2013 | Patterson et al. |
| 2013/0190699 A1 | 7/2013 | Stephan |

FOREIGN PATENT DOCUMENTS

| | | |
|---|---|---|
| JP | H11240047 A | 9/1999 |
| WO | WO 2004/008983 A1 | 1/2004 |
| WO | WO 2009/046425 A1 | 4/2009 |
| WO | WO 2011/097499 A1 | 8/2011 |
| WO | WO 2011/127395 A1 | 10/2011 |
| WO | WO 2013/151755 A1 | 10/2013 |
| WO | WO 95/03752 A1 | 2/2015 |
| WO | WO 2017/093528 A1 | 8/2017 |
| WO | WO 2017/196973 A2 | 11/2017 |

OTHER PUBLICATIONS

Barr et al., "Current Implant Surface Technology: An Examination of Their Nanostructure and Their Influence on Fibroblast Alignment and Biocompatibility," *ePlasty*, vol. 9, p. 198-217 (2009).
Barr et al., "Patterning of Novel Breast Implant Surfaces by Enhancing Silicone biocompatibility, Using Biomimetric Topographies," *ePlasty*, vol. 10, pp. 246-268 (2010).
Barr, S. et al., "Breast implant surface development: perspectives on development and manufacture," *Aesthet. Surg. J.*, vol. 31, No. 1, pp. 56-67 (2011).
Barr, S. et al., "Development, Fabrication and Evaluation of a Novel Biomimetic Human Breast Tissue Derived Breast Implant Surface," *Acta Biomaterialia*, vol. 49, pp. 260-271 (2017).
Barr, S. et al., "Functional Biocompatibility Testing of Silicone Breast Implants and a Novel Classification System Based on Surface Roughness," *J. Mech. Behavior Biomed. Mater.*, vol. 75, pp. 75-81 (2017).
D'Andrea, F. et al., "Modification of cysteinyl leukotriene receptor expression in capsular contracture: Preliminary results," *Ann. Plast. Surg.*, vol. 58, No. 2, pp. 212-213 (2007), abstract only.
Davila et al., "Human Acellular Dermis versus Submuscular Tissue Expander Breast Reconstruction: A Multivariate Analysis of Short-Term Complications," *Archives of Plastic Surgery*, vol. 40, pp. 19-27 (2013).

Del Campo et al., "Fabrication Approaches for generating Complex Micro- and Nanopatterns on Polymeric Surfaces," *Chem. Rev.*, vol. 108, pp. 911-945 (2008).
Ferret et al., "Clarification of Cereplas Breast Implant Manufacturing Processes," *Aesthetic Surgery Journal*, vol. 31, p. 725 (2011).
Garabédian, C. et al., "A Multi-Topographical-Instrument Analysis: The Breast Implant Texture Measurement," *Surf. Topogr.: Metrol. Prop.*, vol. 5, pp. 1-12 (2017).
Harvey et al., "Designing Implant Surface Topography for Improved Biocompatibility," *Expert Rev. Med. Devices*, vol. 10, pp. 1-11 (2013).
"Implant Surfaces Analyzed," The University of Manchester, 2012 (approximate).
Kyle, D.J. et al., "Identification of molecular phenotypic descriptors of breast capsular contracture formation using informatics analysis of the whole genome transcriptome," *Wound Repair Regen.*, vol. 21, No. 5, pp. 762-769 (2013), abstract only.
Kyle, D. et al., "Development and Functional Evaluation of Biomimetic Silicone Surfaces with Hierarchical Micro/Nano-topographical Features Demonstrates Favourable in vitro Foreign Body Response of Breast-Derived Fibroblasts," *Biomaterials*, vol. 52, pp. 88-102 (2015).
Laboratoire national de métrologie et d'essais (LNE) Test Report, File L050836—Document DE/2, Dec. 8, 2010 (33 pages).
Laboratoire national de métrologie et d'essais (LNE) Test Report, File L050836—Document DE/3, Dec. 8, 2010 (33 pages).
Laboratoire national de métrologie et d'essais (LNE) Test Report, File L050836—Document DE/4, Dec. 8, 2010 (33 pages).
Liu et al., "Comparison of Outcomes Using AlloDerm Versus FlexHD for Implant-Based Breast Reconstruction," *Annals of Plastic Surgery*, pp. 105 (2013).
Mendonca, G. et al., "Advancing dental implant surface technology—from micron- to nanotopography," *Biomaterials*, vol. 29, No. 28, pp. 3822-3835 (2008), abstract only.
Militky et al., "Surface Roughness and Fractal Dimension," *The Journal of the Textile Institute*, vol. 92, pp. 91-113 (2001).
Rompen, E. et al., "The effect of material characteristics, of surface topography and of implant components and connections on soft tissue integration: a literature review," *Clin. Oral Implants Res.*, vol. 17, Suppl. 2, pp. 55-67 (2006).
Salzberg et al., "Immediate Breast Reconstruction Using Porcine Acellular Dermal Matrix (Strattice™): Long-term Outcomes and Complications," *Journal of Plastic, Reconstructive & Aesthetic Surgery*, vol. 66, pp. 323-328 (2013).
Schulte, V.A. et al., "Surface topography induces fibroblast adhesion on intrinsically nonadhesive poly(ethylene glycol) substrates," *Biomacromolecules*, vol. 10, No. 10, pp. 2795-2801 (2009), abstract only.
Seth et al., "A Comparative Analysis of Cryopreserved Versus Prehydrated Human Acellular Dermal Matrices in Tissue Expander Breast Reconstruction," *Annals of Plastic Surgery*, vol. 70, pp. 632-635 (2013).
Sforza, M. et al., "A Preliminary Assessment of the Predictability of Fat Grafting to Correct Silicone Breast Implant-Related Complications," *Aesthetic Surgery Journal*, vol. 36, pp. 886-894 (2016).
Sforza, M. et al., "The 21$^{st}$ Century Silicone Breast Implant," *J. Surg. Open Access*, vol. 2, pp. 1-2 (2016).
Sforza, M. et al., "Preliminary 3-Year Evaluation of Experience With SilkSurface and VelvetSurface Motiva Silicone Breast Implants: A Single-Center Experience With 5813 Consecutive Breast Augmentation Cases," *Aesthetic Surgery Journal*, vol. 38, pp. 562-573 (2018).
Shih, B. et al. "Identification of novel keloid biomarkers through profiling of tissue biopsies versus cell cultures in keloid margin specimens compared to adjacent normal skin," *Eplasty*, vol. 10, pp. 187-202 (2010).
Shih, B. et al., "Comparative genomic hybridisation analysis of keloid tissue in Caucasians suggests possible involvement of HLA-DRBS in disease pathogenesis," *Arch. Dermatol. Res.*, vol. 304, No. 3, pp. 241-249 (2012), abstract only.
Syed, F. et al., "Fibroblasts from the growing margin of keloid scars produce higher levels of collagen I and III compared with intralesional

(56) References Cited

OTHER PUBLICATIONS and extralesional sites: clinical implications for lesional site-directed therapy," *Br. J. Dermatol.*, vol. 164, No. 1, pp. 83-96 (2011), abstract only.

Tan, K.T. et al., "Tumour necrosis factor-α expression is associated with increased severity of periprosthetic breast capsular contracture," *Eur. Surg. Res.*, vol. 45, Nos. 3-4, pp. 327-332 (2010), abstract only.

Tan et al., "Hyaluronan, TSG-6, and Inter-α-Inhibitor in Periprosthetic Breast Capsules: Reduced Levels of Free Hyaluronan and TSG-6 Expression in Contracted Capsules," *Aesthetic Surgery Journal*, vol. 31, pp. 47-55 (2011).

Valencia-Lazcano et al., "Characterization of Breast Implant Surfaces and Correlation with Fibroblast Adhesion," Journal of the Mechanical Behavior of Biomedical Materials, vol. 21, pp. 133-148 (2013).

Castel, N. et al., "Polyurethane-coated breast implants revisited: a 30-year follow-up," *Arch. Plast. Surg.*, vol. 42, No. 2, pp. 186-193 (2015).

Derby, B.M. et al., "Textured silicone breast implant use in primary augmentation: core data update and review," *Plast. Reconstr. Surg.*, vol. 135, No. 1, pp. 113-124 (2015).

Efanov, J.I. et al., "Breast-implant texturing associated with delamination of capsular layers: A histological analysis of the double capsule phenomenon," *Ann. Chir. Plast. Esthet.*, vol. 62, No. 3, pp. 196-201 (2017).

Flemming, R.G. et al., "Effects of synthetic micro- and nano-structured surfaces on cell behavior," Biomaterials, vol. 20, No. 6, pp. 573-588 (1999).

Gabriel, A. et al., "The Evolution of Breast Implants," *Clin. Plast. Surg.*, vol. 42, No. 4, pp. 399-404 (2015).

Glicksman, C.A. et al., "A Step Forward Toward the Understanding of the Long-Term Pathogenesis of Double Capsule Formation in Macrotextured Implants: A Prospective Histological Analysis," *Aesthet. Surg. J.*, vol. 39, No. 11, pp. 1191-1199 (2018).

Headon, H. et al., Capsular Contracture after Breast Augmentation: An Update for Clinical Practice, *Arch. Plast. Surg.*, vol. 42, No. 5, pp. 532-543 (2015).

Maxwell, G.P. et al., "Benefits and Limitations of Macrotextured Breast Implants and Consensus Recommendations for Optimizing Their Effectiveness," *Aesthet. Surg. J.*, vol. 34, No. 6, pp. 876-881 (2014).

Mempin, M. et al., "The A, B and C's of Silicone Breast Implants: Anaplastic Large Cell Lymphoma, Biofilm and Capsular Contracture," *Materials*, vol. 11, pp. 1-11. doi:10.3390/ma11122393 (2018).

Munhoz, A.M. et al., "Nanotechnology, nanosurfaces, and silicone gel breast implants: current aspects," *Case Reports Plast. Surg. Hand Surg.*, vol. 4, No. 1, pp. 99-113 (2017).

Stevens, W.G. et al., "Risk factor analysis for capsular contracture: a 5-year Sientra study analysis using round, smooth, and textured implants for breast augmentation," *Plast. Reconstr. Surg.*, vol. 132, No. 5, pp. 1115-1123 (2013).

\* cited by examiner (*; $p < 0.05$)

(*; p <0.05)

(*; p <0.05)

(*; p <0.05)

(*; p <0.05)

(*; p <0.05)

(*; p <0.05)

ISO 25178 Height parameters (Surface texture: Areal)

| | | |
|---|---|---|
| Sa | 326 | nm |
| Sku | 3.21 | |
| Sp | 1671 | nm |
| Sq | 412 | nm |
| Ssk | -0.122 | |
| Sv | -1433 | nm |
| Sz | 3104 | nm |

| ISO 25178 Height parameters (Surface texture: Areal) | | |
|---|---|---|
| Sa | 41.6 | nm |
| Sku | 2.87 | |
| Sp | 191 | nm |
| Sq | 50.8 | nm |
| Ssk | 0.125 | |
| Sv | -160 | nm |
| Sz | 351 | nm |

ISO 25178 Height parameters (Surface texture: Areal)

| | | |
|---|---|---|
| Sa | 4.98 | nm |
| Sku | 2.96 | |
| Sp | 19.4 | nm |
| Sq | 6.29 | nm |
| Ssk | -0.106 | |
| Sv | -23 | nm |
| Sz | 42.3 | nm |

ISO 25178 Height parameters (Surface texture: Areal)

| | | |
|---|---|---|
| Sa | 40 | nm |
| Sku | 19 | |
| Sp | 567 | nm |
| Sq | 74.2 | nm |
| Ssk | 2.53 | |
| Sv | -305 | nm |
| Sz | 871 | nm |

| ISO 25178 Height parameters (Surface texture: Areal) | | |
|---|---|---|
| Sa | 34.73 | µm |
| Sku | 2.89 | |
| Sp | 86.68 | µm |
| Sq | 40.46 | µm |
| Ssk | 0.13 | |
| Sv | -71.95 | µm |
| Sz | 158.63 | µm |

| ISO 25178 Height parameters (Surface texture: Areal) | | |
|---|---|---|
| Sa | -10.81 | μm |
| Sku | 1.77 | |
| Sp | -2 | μm |
| Sq | -13.39 | μm |
| Ssk | 0.43 | |
| Sv | -60.10 | μm |
| Sz | -58.1 | μm |

Figure 24A

| Surface | Scan Size (μm) | Sa (nm) Mean | Sa (nm) ± | Sq (nm) Mean | Sq (nm) ± | Sz (nm) Mean | Sz (nm) ± | Sv (nm) Mean | Sv (nm) SD ± | SP (nm) Mean | SP (nm) ± | Ssk Mean | Ssk ± | Excess Sku (Sku -3) Mean | Excess Sku (Sku -3) ± | Fractal Dimension Mean | Fractal Dimension ± |
|---|---|---|---|---|---|---|---|---|---|---|---|---|---|---|---|---|---|
| ADM BM | 1000x1000 | 6730 | 2009 | 9229 | 2636 | 42796 | 7319 | -19529 | 2505 | 19208 | 8853 | 0.14 | 0.63 | -0.15 | 0.47 | 2.37 | 0.1 |
| | 90x90 | 480.4375 | 177 | 607.63 | 221.9 | 4020.68 | 1352.282 | -2009.8 | 827.42 | 2010.89 | 644.18 | 0.0053 | 0.32 | 0.029 | 0.49 | 2.33 | 0.049 |
| | 10x10 | 69.3 | 29.18 | 87.64 | 34.25 | 572.06 | 177.76 | -268.2 | 98.7 | 303.69 | 92.6 | 0.018 | 0.227 | -0.05 | 0.43 | 2.28 | 0.05 |
| | 1x1 | 5.84 | 2.33 | 7.39 | 2.94 | 46.89 | 15.6 | -23.85 | 7.65 | 23 | 9.18 | -0.043 | 0.14 | -0.1 | 0.73 | 2.29 | 0.02 |
| Smooth (Mentor Smooth) | 1000x1000 | 82.65 | 14.23 | 114.8 | 63.6 | 1238 | 403.4 | -194.45 | 122.7 | 1043.75 | 394.3 | 3.58 | 0.54 | 26.7 | 4.28 | 2.07 | 0.13 |
| | 90x90 | 22.18 | 9.60 | 36.14 | 22.26 | 483 | 258.42 | -144.08 | 114.73 | 339.4 | 154.95 | 1.95 | 0.77 | 12.62 | 6.22 | 2.06 | 0.09 |
| | 10x10 | 4.86 | 1.22 | 7.35 | 2.53 | 126.15 | 57.45 | -27.93 | 10.90 | 98.02 | 51.77 | 2.47 | 0.46 | 28.15 | 34.29 | 2.49 | 0.09 |
| | 1x1 | 4.36 | 2.43 | 5.7 | 3.32 | 46.64 | 34.07 | -22.76 | 18.24 | 25.86 | 17.58 | 0.11 | 0.43 | 0.93 | 0.91 | 2.36 | 0.13 |

Figure 24B

| Textured (Mentor Siltex) | Scan Size | Sa (µm) | Sq (µm) | Sz (µm) | Sv (µm) | SP (µm) | Ssk | | Adj. Sku | | Fractal Dimension | |
|---|---|---|---|---|---|---|---|---|---|---|---|---|
| | 1cmx1cm | 41.73 | 13.70 | 51.38 | 17.68 | 273.43 | 102.40 | -117.69 | 78.10 | 155.73 | 85.30 | 0.57 | 0.36 | -1.88 | 0.13 | 2.81 | 0.11 |
| | 1mmx1mm | 34.73 | 9.31 | 40.46 | 9.8 | 158.63 | 36.79 | -71.95 | 18.34 | 86.68 | 24.88 | 0.29 | 0.33 | -3.02 | 0.76 | 2.27 | 0.06 |
| | 100umx100um | 8.24 | 4.76 | 10 | 5.80 | 40.02 | 20.94 | -20.60 | 11.88 | 19.42 | 9.64 | -0.02 | 0.46 | -3.21 | 0.60 | 2.05 | 0.17 |

Figure 25

| Surface | Scan Size (μm) | Sa (nm) | | Sq (nm) | | Sz (nm) | | Sv (nm) | | Sp (nm) | | Ssk | | Excess Sku (Sku -3) | | Fractal Dimension | |
|---|---|---|---|---|---|---|---|---|---|---|---|---|---|---|---|---|---|
| | | Mean | ± | Mean | ± | Mean | ± | Mean | SD ± | Mean | ± | Mean | ± | Mean | ± | Mean | ± |
| ADM BM Native | 90x90 | 480.44 | 177 | 607.63 | 221.9 | 4020.68 | 1352.282 | -2009.8 | 827.42 | 2010.89 | 644.18 | 0.0053 | 0.32 | 0.029 | 0.49 | 2.33 | 0.049 |
| | 10x10 | 69.3 | 29.18 | 87.64 | 34.25 | 572.06 | 177.76 | -268.2 | 98.7 | 303.69 | 92.6 | 0.018 | 0.227 | -0.05 | 0.43 | 2.28 | 0.05 |
| | 1x1 | 5.84 | 2.33 | 7.39 | 2.94 | 46.89 | 15.6 | -23.85 | 7.65 | 23 | 9.18 | -0.043 | 0.14 | -0.1 | 0.73 | 2.29 | 0.02 |
| ADM BM PDMS F | 90x90 | 484 | 187.88 | 550 | 231.57 | 3366 | 1119.39 | -1692 | 648.16 | 1674 | 472.55 | -0.068 | 0.06 | -0.18 | 0.23 | 2.29 | 0.07 |
| | 10x10 | 95.62 | 27.27 | 122.78 | 35.97 | 762 | 315.77 | -436.8 | 213.1 | 325 | 105.93 | -0.15 | 0.31 | 0.22 | 0.55 | 2.25 | 0.03 |
| | 1x1 | 5.93 | 0.035 | 7.435 | 0.007 | 48.4 | 0.28 | -23.4 | 0.84 | 25 | 1.13 | -0.0085 | 0.28 | 0.14 | 0.09 | 2.25 | 0.029 |
| ADM BM PDMS C | 90x90 | 522.71 | 155.08 | 664 | 191.32 | 4501.14 | 1204.97 | -2235.29 | 883.62 | 2266 | 407.13 | 0.12 | 0.26 | 0.19 | 0.22 | 2.3 | 0.012 |
| | 10x10 | 73.62 | 17.32 | 90.84 | 21.23 | 548 | 137.29 | -280.8 | 90.49 | 267 | 65.48 | 0.038 | 0.15 | -0.19 | 0.44 | 2.27 | 0.09 |
| | 1x1 | 6.28 | 0.91 | 7.91 | 1.23 | 50.32 | 9.52 | -23.4 | 3.66 | 26.92 | 6.99 | 0.03 | 0.29 | 0.09 | 0.47 | 2.25 | 0.03 |

2D image of ADM BM                2D image of ADM BM PDMS F 3D image of ADM BM                3D image of ADM BM PDMS F Profile of ADM BM Profile of ADM BM PDMS F 2D image of ADM BM                2D image of ADM BM PDMS C 3D image of ADM BM        3D image of ADM BM PDMS C Profile of ADM BM Profile of ADM BM PDMS C Section profile S Parameters - Height
Sa      624 nm
Sku     2.45
Sp      1889 nm
Sq      760 nm
Ssk     -0.0981
Sv      -2328 nm
Sz      4217 nm
FD      2.29

ADM BM 90x90um AFM scan

Horizontal autocorrelation function = 7.212±0.32

Vertical autocorrelation function = 9.468±0.37

ADM BM F PDMS 90x90um AFM scan

Horizontal autocorrelation function = 5.977±0.32

Vertical autocorrelation function = 10.856±0.45

ADM BM F PDMS 10x10um AFM scan

Horizontal autocorrelation function = 899.65nm±47nm

Vertical autocorrelation function = 1.47um±75nm

ADM BM 1x1um AFM scan

Horizontal autocorrelation function = 63.622nm±3.2nm

Vertical autocorrelation function = 98.684nm±4.6nm

ADM BM F PDMS 1x1um AFM scan

Horizontal autocorrelation function
=54.41nm±3.0nm

Vertical autocorrelation function =
90.67nm±3.5nm

Section profile

S Parameters - Height
Sa      624 nm
Sku     2.45
Sp      1889 nm
Sq      760 nm
Ssk     -0.0981
Sv      -2328 nm
Sz      4217 nm
FD      2.29

ADM BM 90x90um AFM scan

Horizontal autocorrelation function = 7.212um±0.32

Vertical autocorrelation function = 9.468um±0.37

ADM BM C PDMS 90x90um AFM scan

Horizontal autocorrelation function = 6..86um±0.50

Vertical autocorrelation function = 9.801um±0.43

Section profile

| S Parameters - Height | |
|---|---|
| Sa | 41.1 nm |
| Sku | 2.65 |
| Sp | 185 nm |
| Sq | 50.2 nm |
| Ssk | 0.120 |
| Sv | -157 nm |
| Sz | 342 nm |
| FD | 2.30 |

ADM BM 10x10um AFM scan

Horizontal autocorrelation function = 677.77nm±39nm

Vertical autocorrelation function = 1.047um±46nm

ADM BM 1x1um AFM scan

Horizontal autocorrelation function = 63.62nm±3.2nm

Vertical autocorrelation function = 98.68nm±4.6nm

ADM BM C PDMS 1x1um AFM scan

Horizontal autocorrelation function = 65.36nm±3.6nm

Vertical autocorrelation function = 80.21nm±2.6

Figure 43

| Sample | Size | Autocorrelation Length | | | |
|---|---|---|---|---|---|
| | | Horizontal | | Vertical | |
| | | Mean | SD ± | Mean | SD ± |
| ADM BM Native | 90 x 90um | 8.07 μm | 1.25 | 9.20 μm | 1.85 |
| | 10 x 10um | 1117.31 nm | 245.56 | 1414.27 nm | 337.32 |
| | 1 x 1um | 98.17 nm | 22.58 | 93.71 nm | 23.85 |
| ADM BM PDMS F | 90 x 90um | 6.37um | 0.54 | 10.67um | 0.65 |
| | 10 x 10um | 906.66nm | 234.13 | 1326.4nm | 384.67 |
| | 1 x 1um | 126.47nm | 52.55 | 130nm | 29.81 |
| ADM BM PDMS C | 90 x 90um | 7.02um | 1.061 | 9.77um | 1.96 |
| | 10 x 10um | 1005.8nm | 245.43 | 1390.8nm | 368.03 |
| | 1 x 1um | 87.53nm | 25.11 | 105.7nm | 23.12 |

```
                         SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: PCNA Primer Sequence Left

<400> SEQUENCE: 1
tggagaactt ggaaatggaa a                                                   21

<210> SEQ ID NO 2
<211> LENGTH: 24
<212> TYPE: DNA
<213> ORGANISM: Artificial Sequence
<220> FEATURE:
<223> OTHER INFORMATION: PCNA Primer Sequence Right

<400> SEQUENCE: 2
gaactggttc attcatctct atgg                                                24

<210> SEQ ID NO 3
<211> LENGTH: 19
<212> TYPE: DNA
<213> ORGANISM: Artificial Sequence
<220> FEATURE:
<223> OTHER INFORMATION: VCL Primer Sequence Left

<400> SEQUENCE: 3
ctgaaccagg ccaaaggtt                                                      19

<210> SEQ ID NO 4
<211> LENGTH: 20
<212> TYPE: DNA
<213> ORGANISM: Artificial Sequence
<220> FEATURE:
<223> OTHER INFORMATION: VCL Primer Sequence Right

<400> SEQUENCE: 4
gatctgtctg atggcctgct                                                     20

<210> SEQ ID NO 5
<211> LENGTH: 20
<212> TYPE: DNA
<213> ORGANISM: Artificial Sequence
<220> FEATURE:
<223> OTHER INFORMATION: IL8 Primer Sequence Left
```

```
<400> SEQUENCE: 5
agacagcaga gcacacaagc                                               20

<210> SEQ ID NO 6
<211> LENGTH: 18
<212> TYPE: DNA
<213> ORGANISM: Artificial Sequence
<220> FEATURE:
<223> OTHER INFORMATION: IL8 Primer Sequence Right

<400> SEQUENCE: 6
atggttcctt ccggtggt                                                 18

<210> SEQ ID NO 7
<211> LENGTH: 20
<212> TYPE: DNA
<213> ORGANISM: Artificial Sequence
<220> FEATURE:
<223> OTHER INFORMATION: TNF-a Primer Sequence Left

<400> SEQUENCE: 7
agcccatgtt gtagcaaacc                                               20

<210> SEQ ID NO 8
<211> LENGTH: 18
<212> TYPE: DNA
<213> ORGANISM: Artificial Sequence
<220> FEATURE:
<223> OTHER INFORMATION: TNF-a Primer Sequence Right

<400> SEQUENCE: 8
tctcagctcc acgccatt                                                 18
```

TEXTURED SURFACES FOR BREAST IMPLANTS

CROSS-REFERENCE TO RELATED APPLICATIONS

This application is a continuation of U.S. application Ser. No. 15/119,264 filed on Aug. 16, 2016, issued as U.S. Pat. No. 10,595,979, which is the U.S. national phase entry under 35 U.S.C. § 371 of International Application No. PCT/GB2015/050438, filed on Feb. 16, 2015, each incorporated by reference in its entirety, which claims the benefit of priority to GB Application No. 1402804.7, filed on Feb. 17, 2014.

SEQUENCE LISTING

This application contains a sequence listing, which has been submitted electronically in ASCII format and is hereby incorporated by reference in its entirety. The sequence listing was created on Jan. 19, 2021, under the filename Sequence Listing.txt and is 1,948 bytes in size.

TECHNICAL FIELD

This invention relates to biocompatible implant materials having textured surface topographies for reducing capsular contracture and an undesirable cellular response upon implantation into the body, with particular application to prosthetic implants, such as silicone breast implants. Methods for preparing such surfaces are also disclosed.

BACKGROUND

Fibrous capsule formation around soft tissue body implants remains a persistent problem for many patients following prosthesis implantation. Silicone shell breast implants are particularly troublesome with potential development of capsular contracture, which is considered to be one of the primary reasons for device failure.

Capsular Contracture

The pathoetiology of capsular contracture formation around silicone mammary implants is both complex and enigmatic, however; it is thought to be an over-exaggeration of the normal foreign body reaction. There are a number of known risk factors for its development such as implantation post-radiotherapy and bacterial infection around the implant. In addition, some studies have shown an association between capsular contracture in the case of mammary implants with sub-glandular versus sub-muscular placement of the implant and use of smooth versus textured silicone shells.

There is a consensus that in the case of breast implants, the use of textured silicone implants lowers the incidence of capsular contracture formation. It is thought that the extremely roughened surface of these implants disrupts and prevents the formation of parallel collagen bundles around the implant thus preventing thickened capsule formation, which can contract around the prosthesis and result in firmness, deformation and pain; the signs and symptoms most commonly associated with this pathology.

The pathoetiology of breast capsular contracture formation can be loosely viewed in two broadly distinct explanations: one school of thought is that the initial protein adsorption and subsequent cell attachment to the mammary prosthesis in the first minutes to hours after implantation can dictate the extent of the subsequent foreign body reaction and clinical outcome through cell mediated cytokine/chemokine release and extracellular matrix production. Thus, the nano- and micro-scale features on implants are important to this hypothesis as it is primarily centred on the initial cell response at a microscopic level and involves specific cell-surface (motif-integrin) binding via adsorbed proteins from human serum. In contrast, another hypothesis, which led to the production of textured implants, centres on the problem of parallel bundle fibres forming in the capsule tissue adjacent to the implant. It is proposed that parallel collagen fibres within the capsule promote an increased capsular contraction around the implant. Textured implants therefore aim to disrupt the capsule tissue formation around the implant, through its roughened texture such that parallel collagen fibres are unable to form and thus co-ordinated myofibroblast initiated contraction is inhibited. The latter hypothesis, however, neglects to consider the initial reaction of the body to the implant and instead focuses on attempting to firmly integrate the implant within the breast so that the movement of the prosthesis is minimized; potentially leading to reduced contracture. However, this approach can be viewed more as altering the course of capsular contracture as opposed to preventing the capsule contracture from being initiated. Furthermore, once capsular contracture has occurred around a textured implant, surgical removal proves much more traumatic and can result in the unnecessary loss of the surrounding breast tissue as there is excessive tissue ingrowth into the more heavily textured implant (the so called "velcro effect").

Present methods of addressing the problems associated with adverse cellular response, cell ingrowth and capsule contracture have been approached from two distinct directions. Researchers have for example reported some success in avoiding adverse cellular response by using soft tissue matrix allografts (typically in the form of acellular dermal matrix) to cover the implant in the implant site and thus providing a scaffold on which the patient's own cells can repopulate and vascularise the graft, see e.g. [Davila, A. A. 2012], [Salzberg, C. A. 2012] and [Liu, D. Z. 2013]. Secondly, researchers have focused on investigating and refining the respective implant surfaces in order to improve cellular interactions.

The Implant Surface

The basic design and fabrication of current commercially available breast implants was generally conceived in the 1960's with limited scientific consideration or evaluation in particular due to the available scientific know-how and technology at the time. Nonetheless, the primary concern for inventors and producers over time has been gaining approval from the relevant device regulatory authorities such as the Food and Drug Administration (FDA) approval of silicone implant safety in the United States. Thus, implants created to date were designed mostly to reduce capsular contracture formation rather than minimisation of the foreign body reaction and as a consequence, extensive analysis of the physical, mechanical and chemical properties of breast implants would likely benefit from further detailed investigation.

A number of factors have since been considered by investigators in this field when designing a high performance, functional and long lasting implant. In particular, there are a number of surface properties, which appear to influence the response of cells to an implant both in vitro and in vivo. Included among these are the effects of surface roughness, topography, wettability and elastic modulus on cell response. Since silicone is transparent, highly elastic, durable, permeable to oxygen, FDA approved and extensively biologically tested, it remains the primary material for breast prosthesis fabrication. The innate properties of vulcanized silicone, in the form required for implantation (high tensile strength and tear resistance), mean that the chemical and mechanical surface properties of implants are already established and resistant to change. Thus, prior art approaches have focused on modulating surface topography/roughness in attempts to alter or improve prosthesis performance.

Surface Texture

In general, implant surfaces may have a primary surface profile made up of the surface form, which is the general shape of the material surface. For instance, the surface of a breast implant will generally adopt a curved form, perhaps with additional contours/waves which may be natural features/undulations that form as a result of the physical make-up of the implant. The way in which such surfaces interact with body tissue at a cellular level is however better described by reference to the surface roughness, which refers to the topographical texture of the primary implant surface on a smaller scale. Surface roughness is typically classified on three distinct scales; macro roughness (1 µm and greater), micro roughness (100 nm to 1 µm) and nano roughness (1 nm to 100 nm). Each of these different roughness scales has been observed to have a distinct effect on both initial cell response (up to 24 hours) and longer-term cell response (up to weeks and months). Of course, a surface may comprise one or more of these roughness levels. For instance, the primary implant surface may contain only one of topographical macro-roughness (i.e. wherein surface features at a micro roughness and/or nano roughness scale are not present), micro-roughness (i.e. wherein surface features at a macro roughness and/or nano roughness scale are not present) and nano roughness (i.e. wherein surface features at a macro roughness and/or micro roughness scale are not present). Alternatively, implant surfaces may possess surface roughness on more than one of these scales. For instance, the primary implant surface may contain topographical macro-roughness as well as micro-roughness and/or nano-roughness. In such surfaces, the relevant features may appear as adjacent textures and/or as superimposed textures within the primary surface profile. An example of superimposed features is wherein the macro-roughness profile further contains micro- and/or nano-roughness textures as secondary/tertiary roughness profiles respectively.

Surface Texture and Cellular Response

It is generally understood by researchers in the field that surface topography and roughness can influence cell response to a material [Schulte, V. A. 2009], [van Kooten, T. G. 1998], [Rompen, E. 2006]. Research has for example shown that surface topography can influence clinical outcomes for patients with hip replacements, dental implants and silicone breast implants [Barnsley, G. P. 2006], [Harvey, A. G. 2013], [Mendonca, G. 2008]. In particular, textured implants have been shown to significantly reduce capsular contracture in comparison to smooth implants [Barnsley, G. P. 2006]. However, as explained below there has been a great degree of difficulty in identifying key surface feature(s) that affect the cellular response upon implantation.

The idea of "contact guidance" first postulated by Weiss in 1934 is now well recognised by researchers in the field of biomaterial/surface-substrate interaction. It has been shown on a number of occasions that cells are able to sense and respond to topographical cues down to nanometre scale. The main cues for cell attachment to and spreading on a substrate (whether to native extra-cellular matrix (ECM) in vivo or a substrate in vitro) and subsequent proliferation are through chemokine/growth factor stimulation in addition to both mechanical and topographical cues which cells are able to sense in their environment via their filopodia.

Surface topography and degree of surface roughness (i.e. macro, micro or nano—as discussed above) can influence both cell genotype and phenotype. The roughness scale to which cells are most responsive is, however, quite complex. For instance, cell response can depend on cell type, surface substrate, surface topography and time scale. Furthermore, the outcomes measured can also vary and include cell attachment, alignment, migration, proliferation, gene and protein expression. Therefore, the best results for the design of a novel surface topography to initiate and encourage specific cellular response are likely to be achieved if targeted at the particular desired cell response. As a result, the surface features that might be important for providing desirable cell responses in a given environment have been difficult to identify.

Therefore, new approaches are now required for the design, development and manufacture of textured implants in order to reduce capsular contracture. [Harvey, A. G. 2013].

Preparation of Smooth and Textured Implants

Early approaches at manufacturing breast implants had focused on using polyurethane as the implant surface and had some success in minimising capsular contracture. However, due to health concerns, use of polyurethane was eventually superseded by silicone as the polymer material of choice due to silicone's biologically benign nature and its FDA approval as discussed above.

Breast implants are typically formed by dipping an implant-shaped template (mandrel) into liquid polymer so that it becomes uniformly coated. Prior to curing, the implant can be subjected to a texturizing process such as imprinting on a mould to create a patterned texture in silicone (Mentor Siltex™ Implant). The mandrel is then placed in a hot, laminar flow cabinet to allow for the polymer to solidify around the template (curing). This curing step allows for an equal amount of heat to be applied around the implant so that a homogenous surface is created. This process can be repeated several times to increase the thickness of the implant and the implant may then be further treated with a solvent if it is to be smooth (to further smooth out the surface). Silicone breast implants are thus typically made through this same basic process, regardless of whether they are designed to be smooth or textured.

In this regard, implant surfaces that are "smooth" do in fact usually exhibit an unintentional minor degree of surface roughness as a result of fine ripples, grooves and/or other surface anomalies that are an inherent bi-product of the process by which the surfaces are prepared (for instance forming during the curing process as the liquid silicone trickles down the mandrel under force of gravity).

Formally "textured" surfaces, however, typically comprise a heavily textured surface topography. Such textures may be regular repeating geometric patterns or may be irregular in nature.

WO2009/046425 for example describes textured implant surfaces having a highly ordered regular geometric repeating pattern (parallel bars) at the micro- or nano-scale which are claimed to disrupt bacterial biofilm formation on the implant surface. The repeating pattern is formed by production of a master pattern using photolithographic techniques as applied in semiconductor manufacture and the master pattern is then used to contact print replicated patterns on the surface of the implant. However, whilst conventional photolithographic techniques can provide simple geometric structures such as the grooves depicted in WO2009/046425, such methods are not attractive when more complex geometric patterns are sought (e.g. spheres, wedges) since such patterns depend on the preparation and use of photo-masks with graded levels of opacity through which graded levels of UV light may pass onto the photoresist. Such photo-masks are expensive to produce and cannot be altered once produced, meaning that each desired design/pattern requires the prior preparation of bespoke photo-masks.

WO95/03752 (see FIG. 4) also depicts an implant surface having a highly ordered regular geometric repeating pattern (pillars). These uniform micro-textured surfaces may be produced by use of ion-beam thruster technology (see e.g. page 2 of WO95/03752). However, such uniformly patterned implant surfaces typically lead to the orientation of fibroblasts in conformity with the respective surface pattern (see e.g. paragraphs 28, 34 and FIGS. 14 and 15 of WO2009/046425). As explained above, however, the organised orientation of fibroblasts and, subsequently, collagen is understood to be a key stage in the promotion of fibrotic capsule contracture. Thus, while such ordering of fibroblast might be more acceptable in external applications such as for use in wound healing, such highly ordered patterned surfaces are not therefore ideal for use in prosthetic implants, such as breast implants, which are prone to capsule formation and contracture.

A variety of irregular (i.e. non-uniform) textured implant surfaces have however been proposed in the literature with a range of different cellular outcomes observed. A number of approaches to providing textured surfaces have however failed to reduce or prevent capsule formation and subsequent contracture. For instance, paragraphs 86-89 and FIGS. 7 to 9 of WO 2011/097499 describe a number of irregular textured surfaces, which fail to provide desirable capsule modulation. A 'salt loss' technique is used in the production of commercially available Biocell™ (Allergan, Inc.). Such surfaces are described and illustrated in more detail in [Barr, S. 2009]. This technique results in an open-cell structure. Implant surfaces formed by this "salt loss" technique are also depicted in FIG. 5 of WO95/03752. Such implants are not however ideal as introduction of foreign particles to the silicone surface may lead to detrimental effects on the silicone implant properties, for instance if the relevant salts become encapsulated in the silicone.

An alternative technique for forming an open-cell structure involves the use of an open cell foam or fibrous polymeric fabric to either form or imprint a pattern on the implant surface. For instance, the commercially available Siltex™ implant (Mentor), uses a mandrel with a polyurethane foam texture that is imprinted into the silicone during curing. Similar fabric/open cell foam-based texturizing techniques are also described in US 2011/0276134, WO 2011/097499 and US2002/0119177. If such open cell-like structures are achieved using a fabric with a uniform geometry, then open-cell structures with small-scale irregularity but long-distance uniformity may be achieved (see e.g. FIGS. 10 and 12 of US 2011/0276134). Whilst such open cell structures are reported to achieve some success in preventing capsule formation, they also have drawbacks because the fine interstices and edges formed as a result of the process may lack robustness and may break away from the implant surface under frictional forces leading to detached silicone fragments in the body. Furthermore, the large, typically macroscopic, pores formed by such processes have deep sides and pits which means that cells become embedded in the deep valleys of the implant and cannot migrate due to sides that are too steep for the cells to climb. Whilst this may hinder the process of capsule formation, the cells cannot display natural migratory and proliferative behaviour with contact inhibition of cells within deep troughs of heavily textured implants. This is undesirable since an adherent cell such as a fibroblast that is able to attach, migrate, proliferate and function on a surface with minimal stress and without inhibition, is likely to behave as a fibroblast would in vivo within native ECM. Nonetheless, the deep troughs typically still allow the eventual substantial in-growth of cells into the surface pores, but whilst this may firmly anchor the implant in place in the body, excessive tissue in-growth may lead to difficulties later if the implant has to be removed or replaced (for instance if capsular contraction nonetheless occurs) as a large amount of body tissue will also have to be cut away with the implant.

WO95/03752 discloses an alternative method for producing irregular surface topographies in silicone breast implants by adding filtered silicone particles to the still tacky surface of the mandrel before curing and application of a top-coat (pages 10 to 12).

As discussed, present methods for forming irregular implant surfaces typically rely on crude and inherently unpredictable processes. Such methods thus provide non-reproducible surfaces, which may differ significantly from batch to batch, leading to potentially unreliable results. It is however desirable to be able to control the surface features with a high degree of accuracy, particularly in the case of prosthetic implants such as breast implants, where differences in micro and nano features have been shown to play an important role in cellular interaction, biocompatibility and capsular contraction. Thus, there remains a need for methods which provide control of irregular surface features with a higher degree of accuracy and reproducibility and/or which provide a higher degree of flexibility for producing different designs.

As discussed above, it is therefore desirable for an implant surface to promote effective cell attachment, migration and proliferation (such as would naturally occur within native extra-cellular matrix (ECM)) and/or to minimise the stressed cellular response (which can for example result in cells secreting inflammatory and fibro-proliferative cytokines such as tumour necrosis factor alpha (TNF-α) and others) with the object of reducing implant capsular contracture formation. For cosmetic or prosthetic implants that are placed below the skin surface (typically below mammary tissue in the case of breast implants) but which change the external appearance of the body, e.g. breast implants, it is also desirable for the implant to be well anchored and to maintain a natural appearance while also being easily surgically removable should some capsular contracture arise, without having to remove a significant amount of adherent normal tissue with it.

As is evident from the above comments, there is a need to provide new and/or improved implants with surface topographies that mitigate or obviate one or more of the problems identified above. For instance, there is a desire to provide new implants which mitigate or obviate capsular contraction, provide desirable levels of tissue anchoring and cellular in-growth, and/or which minimise the stress/inflammatory response. Ideally, such surfaces should show high levels of biocompatibility and preferably allow the implant to retain a natural appearance. There is also a desire for methods that can produce such topographical features reliably and accurately on an implant surface.

SUMMARY OF INVENTION

The inventors propose new biomimetic textured surface topographies for implants, particularly breast implants. The inventors have found in particular that by controlling aspects of the surface texture, for example the surface roughness at macro, micro and/or nano scale to resemble corresponding features of the general surface topography of the basement membrane and/or papillary dermis of human skin, desirable and indeed improved cellular response, reduced capsular contraction and appropriate cellular anchoring/in-growth could be achieved compared to conventional smooth and textured implants.

The inventors also propose novel methods for preparing textured surface structures on implants based on the surface topographies of biological tissue. Such methods allow the controlled replication of textured surface features and have the potential for wide applicability in the field of texturizing implants in general.

This approach to designing implant surface structures from first principles rather than by modification of currently available devices, which represents a significant departure from current trends and is expected to have a large impact on the implant industry.

DETAILED DESCRIPTION

In an aspect of the invention is provided a synthetic implant material comprising textured surface, suitably an irregular textured surface, said surface characterised by having one or more of the group consisting of i) to vii):

i) a mean surface roughness Sa value of:
   a) from 1 μm to 20 μm, optionally 1 to 15 μm, optionally 2 to 12 μm, optionally 3 to 9 μm, at an area scale of 1 mm×1 mm; and/or
   b) from 0.1 μm to 5 μm, optionally 0.2 μm to 2 μm, optionally 0.2 μm to 1 μm at an area scale of 90 μm×90 μm; and/or
   c) from 10 nm to 1 μm, optionally 30 nm to 500 nm, optionally 30 nm to 200 nm at an area scale of 10 μm×10 μm; and/or
   d) from 2 nm to 15 nm, optionally 2 nm to 10 nm, optionally 2 nm to 9 nm, optionally 3 nm to 9 nm, at an area scale of 1 μm×1 μm;

ii) a root mean square height Sq value of:
   a) from 2 μm to 30 μm at an area scale of 1 mm×1 mm; and/or
   b) from 0.2 μm to 5 μm, optionally 0.2 μm to 1.5 μm, optionally 0.3 μm to 1.0 μm at an area scale of 90 μm×90 μm; and/or
   c) from 20 nm to 250 nm, optionally 30 nm to 250 nm, optionally 40 nm to 250 nm, optionally 60 nm to 200 nm at an area scale of 10 μm×10 μm; and/or
   d) from 2 nm to 20 nm, optionally 4 nm to 12 nm, optionally 4 nm to 11 nm, optionally 5 nm to 11 nm, optionally 6 nm to 10 nm, optionally 6 nm to 9 nm, at an area scale of 1 μm×1 μm;

iii) a maximum peak height to trough depth Sz value of:
   a) from 10 μm to 60 μm, at an area scale of 1 mm×1 mm; and/or
   b) from 1 μm to 10 μm, optionally 1 μm to 7 μm, optionally 2 μm to 7 μm, optionally 2 μm to 6 μm at an area scale of 90 μm×90 μm; and/or
   c) from 0.1 μm to 2 μm, optionally 0.1 μm to 1.5 μm, optionally 0.3 μm to 1.2 μm at an area scale of 10 μm×10 μm; and/or
   d) from 10 nm to 100 nm, optionally 30 nm to 70 nm, optionally 40 nm to 65 nm, optionally 40 nm to 60 nm, at an area scale of 1 μm×1 μm;

iv) a mean surface skewness Ssk value of:
   a) from −1.0 to +1.0, optionally −0.7 to +0.7, optionally −0.5 to +0.5 at an area scale of 1 mm×1 mm; and/or
   b) from −1.0 to +1.0, optionally −0.7 to +0.7, optionally −0.5 to +0.5 at an area scale of 90 μm×90 μm; and/or
   c) from −0.7 to +0.7, optionally −0.5 to +0.5, optionally −0.3 to +0.3 at an area scale of 10 μm×10 μm; and/or
   d) from −0.5 to +0.5, optionally −0.4 to +0.4, optionally −0.3 to +0.3, at an area scale of 1 μm×1 μm;

v) a mean excess kurtosis value (Sku minus 3) of:
   a) from −1.0 to +1.0, optionally −0.7 to +0.7 at an area scale of 1 mm×1 mm; and/or
   b) from −1.0 to +1.0, optionally −0.7 to +0.7, optionally −0.5 to +0.5, optionally −0.3 to +0.3 at an area scale of 90 μm×90 μm; and/or
   c) from −1.5 to +1.5, optionally −1.0 to +1.0, optionally −0.8 to +0.8, optionally −0.7 to +0.7, optionally −0.5 to +0.5, optionally −0.3 to +0.3 at an area scale of 10 μm×10 μm; and/or
   d) from −0.9 to +0.7, optionally −0.5 to +0.5, optionally −0.3 to +0.3, optionally −0.2 to +0.2, at an area scale of 1 μm×1 μm;

vi) a fractal dimension of
   a) from 2.1 to 2.5, optionally 2.2 to 2.5 at an area scale of 1 mm×1 mm; and/or
   b) from 2.1 to 2.5, optionally 2.2 to 2.4 at an area scale of 90 μm×90 μm; and/or
   c) from 2.1 to 2.5, optionally 2.2 to 2.4 at an area scale of 10 μm×10 μm; and/or
   d) from 2.1 to 2.5, optionally 2.1 to 2.4, optionally 2.1 to 2.35, optionally 2.2 to 2.35, at an area scale of 1 μm×1 μm;

vii) a linear (horizontal or vertical) autocorrelation length of:
   a) from 20 μm to 200 μm, optionally 30 μm to 200 μm, optionally 50 μm to 200 μm, optionally 60 μm to 190 μm, at an area scale of 1 mm×1 mm; and/or
   b) from 3 μm to 15 μm, optionally 4 μm to 15 μm, optionally 5 μm to 13 μm, optionally 5 μm to 10 μm at an area scale of 90 μm×90 μm; and/or
   c) from 0.5 μm to 2.5 μm, optionally 0.5 μm to 2 μm, optionally 0.6 μm to 2 μm, optionally 0.6 μm to 1.8 μm, optionally 0.7 μm to 1.8 μm at an area scale of 10 μm×10 μm and/or
   d) from 40 nm to 200 nm, optionally 20 nm to 180 nm, optionally 60 nm to 180 nm, optionally 50 nm to 150 nm, optionally 60 nm to 130 nm, optionally 70 nm to 130 nm at an area scale of 1 μm×1 μm.

In embodiments, the surface is characterised in having one selected from the following:
1. (i)
2. (ii)
3. (iii)
4. (iv)
5. (v)
6. (vi)
7. (vii)
8. (i) and (ii)
9. (i) and (iii)
10. (i) and (iv)
11. (i) and (v)
12. (i) and (vi)
13. (i) and (vii)
14. (ii) and (iii)
15. (ii) and (iv)
16. (ii) and (v)
17. (ii) and (vi)
18. (ii) and (vii)
19. (iii) and (iv)

20. (iii) and (v)
21. (iii) and (vi)
22. (iii) and (vii)
23. (iv) and (v)
24. (iv) and (vi)
25. (iv) and (vii)
26. (v) and (vi)
27. (v) and (vii)
28. (vi) and (vii)
29. (i), (ii) and (iii)
30. (i), (ii) and (iv)
31. (i), (ii) and (v)
32. (i), (ii) and (vi)
33. (i), (ii) and (vii)
34. (i), (iii) and (iv)
35. (i), (iii) and (v)
36. (i), (iii) and (vi)
37. (i), (iii) and (vii)
38. (i), (iv) and (v)
39. (i), (iv) and (vi)
40. (i), (iv) and (vii)
41. (i), (v) and (vi)
42. (i), (v) and (vii)
43. (i), (vi) and (vii)
44. (ii), (iii) and (iv)
45. (ii), (iii) and (v)
46. (ii), (iii) and (vi)
47. (ii), (iii) and (vii)
48. (ii), (iv) and (v)
49. (ii), (iv) and (vi)
50. (ii), (iv) and (vii)
51. (ii), (v) and (vi)
52. (ii), (v) and (vii)
53. (ii), (vi) and (vii)
54. (iii), (iv) and (v)
55. (iii), (iv) and (vi)
56. (iii), (iv) and (vii)
57. (iii), (v) and (vi)
58. (iii), (v) and (vii)
59. (iii), (vi) and (vii)
60. (iv), (v) and (vi)
61. (iv), (v) and (vii)
62. (iv), (vi) and (vii)
63. (v), (vi) and (vii)
64. (i), (ii), (iii) and (iv)
65. (i), (ii), (iii) and (v)
66. (i), (ii), (iii) and (vi)
67. (i), (ii), (iii) and (vii)
68. (i), (ii), (iv) and (v)
69. (i), (ii), (iv) and (vi)
70. (i), (ii), (iv) and (vii)
71. (i), (ii), (v) and (vi)
72. (i), (ii), (v) and (vii)
73. (i), (ii), (vi) and (vii)
74. (i), (iii), (iv) and (v)
75. (i), (iii), (iv) and (vi)
76. (i), (iii), (iv) and (vii)
77. (i), (iii), (v) and (vi)
78. (i), (iii), (v) and (vii)
79. (i), (iii), (vi) and (vii)
80. (i), (iv), (v) and (vi)
81. (i), (iv), (v) and (vii)
82. (i), (iv), (vi) and (vii)
83. (i), (v), (vi) and (vii)
84. (ii), (iii), (iv) and (v)
85. (ii), (iii), (iv) and (vi)
86. (ii), (iii), (iv) and (vii)
87. (ii), (iii), (v) and (vi)
88. (ii), (iii), (v) and (vii)
89. (ii), (iii), (vi) and (vii)
90. (ii), (iv), (v) and (vi)
91. (ii), (iv), (v) and (vii)
92. (ii), (iv), (vi) and (vii)
93. (ii), (v), (vi) and (vii)
94. (iii), (iv), (v) and (vi)
95. (iii), (iv), (v) and (vii)
96. (iii), (iv), (vi) and (vii)
97. (iii), (v), (vi) and (vii)
98. (iv), (v), (vi) and (vii)
99. (i), (ii), (iii), (iv) and (v)
100. (i), (ii), (iii), (iv) and (vi)
101. (i), (ii), (iii), (iv) and (vii)
102. (i), (ii), (iii), (v) and (vi)
103. (i), (ii), (iii), (v) and (vii)
104. (i), (ii), (iii), (vi) and (vii)
105. (i), (iii), (iv), (v) and (vi)
106. (i), (iii), (iv), (v) and (vii)
107. (i), (iii), (iv), (vi) and (vii)
108. (i), (iii), (v), (vi) and (vii)
109. (i), (iv), (v), (vi) and (vii)
110. (ii), (iii), (iv), (v) and (vi)
111. (ii), (iii), (iv), (v) and (vii)
112. (ii), (iii), (iv), (vi) and (vii)
113. (ii), (iii), (v), (vi) and (vii)
114. (ii), (iv), (v), (vi) and (vii)
115. (iii), (iv), (v), (vi) and (vii)
116. (i), (ii), (iii), (iv), (v) and (vi)
117. (i), (ii), (iii), (iv), (v) and (vii)
118. (i), (ii), (iii), (iv), (vi) and (vii)
119. (i), (ii), (iii), (v), (vi) and (vii)
120. (i), (ii), (iv), (v), (vi) and (vii)
121. (i), (iii), (iv), (v), (vi) and (vii)
122. (ii), (iii), (iv), (v), (vi) and (vii)
123. (i), (ii), (iii), (iv), (v), (vi) and (vii)

In embodiments, the surface is characterised in having one selected from the following:
(A) any one of (i) to (vii)
(B) any two of (i) to (vii)
(C) any three of (i) to (vii)
(D) any four of (i) to (vii)
(E) any five of (i) to (vii)
(F) any six of (i) to (vii)
(G) all of (i) to (vii)

Thus, in embodiments, the surface is characterised in having one selected from the following:
(A) any one of 1. to 7. above
(B) any one of 8. to 28. above
(C) any one of 29. to 63. above
(D) any one of 64. to 98. above
(E) any one of 99. to 115. above
(F) any one of 116. to 122. above
(G) 123. above In embodiments, the surface has (i) a mean surface roughness Sa as described above and is characterised in having surface properties selected from the following:
1, 8 to 13, 29 to 43, 64 to 83, 99 to 109, 116 to 121, and 123.

In embodiments, the surface has (ii) a mean surface roughness Sq as described above and is characterised in having surface properties selected from the following:
4, 10, 15, 19, 30, 34, 38 to 40, 44, 48 to 50, 54 to 56, 60 to 62, 64, 68 to 70, 74 to 76, 80 to 82, 84 to 86, 90 to 92, 94 to 96, 99 to 101, 105 to 107, 109 to 112, 114 to 118, and 120 to 123.

In embodiments, the surface has (iii) a maximum peak height to trough depth Sz as described above and is characterised in having surface properties selected from the following:

5, 11, 16, 20, 23, 31, 35, 38, 41 to 42, 45, 48, 51 to 52, 54, 57 to 58, 60 to 61, 65, 68, 71 to 72, 74, 77 to 78, 80 to 81, 83 to 84, 87 to 88, 90 to 91, 93 to 95, 97 to 99, 102 to 103, 105 to 106, 108 to 111, 113 to 117, and 119 to 123.

In embodiments, the surface has (iv) a mean surface skewness Ssk as described above and is characterised in having surface properties selected from the following:

2, 14 to 18, 29 to 33, 44 to 53, 64 to 73, 84 to 93, 99 to 104, 110 to 114, 116 to 120 and 123.

In embodiments, the surface has (v) a mean excess kurtosis value (Sku minus 3) as described above and is characterised in having surface properties selected from the following:

2, 14 to 18, 29 to 33, 44 to 53, 64 to 73, 84 to 93, 99 to 104, 110 to 114, 116 to 120, and 123.

In embodiments, the surface has (vi) a fractal dimension as described above and is characterised in having surface properties selected from the following:

6, 12, 17, 21, 24, 26, 28, 32, 36, 39, 41, 43, 46, 49, 51, 53, 55, 57, 59 to 60, 62 to 63, 66, 69, 71, 73, 75, 77, 79 to 80, 82 to 83, 85, 87 to 89 to 90, 92 to 94, 96 to 98, 100, 102, 104 to 105, 107 to 110, 112 to 116, 118 to 123.

In embodiments, the surface has (vii) a linear (horizontal or vertical) autocorrelation length as described above and is characterised in having surface properties selected from the following:

7, 13, 18, 22, 25, 27 to 28, 33, 37, 40, 42 to 43, 47, 50, 52 to 53, 56, 58 to 59, 61 to 63, 67, 70, 72 to 73, 76, 78 to 79, 81 to 83, 86, 88 to 89, 91 to 93, 95 to 98, 101, 103 to 104, 106 to 109, 111 to 115, 117 to 123.

From within each of (i) to (vii) described above, the textured surface may have one or more of a), b), c) and d). Specifically, the textured surface may have, for each of (i) to (vii) any one selected from the following:

a)
b)
c)
d)
a) and b)
a) and c)
a) and d)
a), b) and c)
a), b) and d)
a), c) and d)
a), b), c) and d)
b) and c)
b) and d)
b), c) and d)
c) and d)

In an aspect of the invention is provided a synthetic implant material comprising a textured surface, said surface having (i). In particular, the surface is characterised in having a feature or features selected from the following (i) a); (i) b); (i) c); (i) d); (i) a) and b); (i) a) and c); (i) a) and d); (i) a), b) and c); (i) a), b) and d); (i) a), c) and d); (i) a), b), c) and d); (i) b) and c); (i) b) and d); and (i) b), c) and d).

In an aspect of the invention is provided a synthetic implant material comprising a textured surface, said surface having (ii). In particular, the surface is characterised in having a feature or features selected from the following (ii) a); (ii) b); (ii) c); (ii) d); (ii) a) and b); (ii) a) and c); (ii) a) and d); (ii) a), b) and c); (ii) a), b) and d); (ii) a), c) and d); (ii) a), b), c) and d); (ii) b) and c); (ii) b) and d); and (ii) b), c) and d).

In an aspect of the invention is provided a synthetic implant material comprising a textured surface, said surface having (iii). In particular, the surface is characterised in having a feature or features selected from the following (iii) a); (iii) b); (iii) c); (iii) d); (iii) a) and b); (iii) a) and c); (iii) a) and d); (iii) a), b) and c); (iii) a), b) and d); (iii) a), c) and d); (iii) a), b), c) and d); (iii) b) and c); (iii) b) and d); and (iii) b), c) and d).

In an aspect of the invention is provided a synthetic implant material comprising a textured surface, said surface having (iv). In particular, the surface is characterised in having a feature or features selected from the following (iv) a); (iv) b); (iv) c); (iv) d); (iv) a) and b); (iv) a) and c); (iv) a) and d); (iv) a), b) and c); (iv) a), b) and d); (iv) a), c) and d); (iv) a), b), c) and d); (iv) b) and c); (iv) b) and d); and (iv) b), c) and d).

In an aspect of the invention is provided a synthetic implant material comprising a textured surface, said surface having (v). In particular, the surface is characterised in having a feature or features selected from the following (v) a); (v) b); (v) c); (v) d); (v) a) and b); (v) a) and c); (v) a) and d); (v) a), b) and c); (v) a), b) and d); (v) a), c) and d); (v) a), b), c) and d); (v) b) and c); (v) b) and d); and (v) b), c) and d).

In an aspect of the invention is provided a synthetic implant material comprising a textured surface, said surface having (vi). In particular, the surface is characterised in having a feature or features selected from the following (vi) a); (vi) b); (vi) c); (vi) d); (vi) a) and b); (vi) a) and c); (vi) a) and d); (vi) a), b) and c); (vi) a), b) and d); (vi) a), c) and d); (vi) a), b), c) and d); (vi) b) and c); (vi) b) and d); and (vi) b), c) and d).

In an aspect of the invention is provided a synthetic implant material comprising a textured surface, said surface having (vii). In particular, the surface is characterised in having a feature or features selected from the following (vii) a); (vii) b); (vii) c); (vii) d); (vii) a) and b); (vii) a) and c); (vii) a) and d); (vii) a), b) and c); (vii) a), b) and d); (vii) a), c) and d); (vii) a), b), c) and d); (vii) b) and c); (vii) b) and d); and (vii) b), c) and d).

Each of the areal (S) surface texture parameters (i) to (vii) discussed herein is described in ISO 25178-2: 2012(E). The measurement and calculation methodology used to arrive at the values for the parameters is discussed below.

As noted above, suitably the textured surface is an irregular textured surface.

Suitably, the implant material is a synthetic implant material (e.g. an artificial implant material), and in preferred embodiments is a biomimetic material.

Area Scales/Resolution in Surfaces of the Invention

The implant materials described herein may thus include macro-surface roughness features, such as described by a) above, and/or micro roughness features, such as described by b) above, and/or nano surface features, such as described by c) and/or d) above.

Thus, in embodiments of any of the aspects herein, for each of the scale-dependent features a) to d), said surface may have a), b), c) or d), for instance a). Alternatively, the surface may have b). The surface may on the other hand have c). Alternatively, the surface may have d). In other embodiments, the surface may have more than one, e.g. 2, 3 or 4 of the roughness features a) to d). In embodiments, the surface has a)+b), such as where the surface does not include c) or d). In other embodiments, the surface has a)+c), such as where the surface does not include b) or d). In other embodiments the surface has a)+d), such as where the surface does not include b) or c). In further embodiments, the surface has b)+c), such as where the surface do not include a) or d). In other embodiments the surface has b)+d), such as where the surface does not include a) or c). In other embodiments, the surface has a)+b)+c), but not d). In other embodiments, the surface has a)+c)+d), but not b). In other embodiments, the surface has a)+b)+d), but not c). In other embodiments, the surface has b)+c)+d), but not a). In other embodiments, the surface has a)+b)+c)+d).

The implant material of the invention may have a surface comprising one or more of these roughness scales at discrete, e.g. adjacent, parts of the implant. Typically however, where more than one, for instance two, three or four of the respective area scales are provided on the implant, they are superimposed to provide a complex surface with a primary surface topography corresponding to the larger roughness value (e.g. a) or b)), a secondary surface topography superimposed onto the primary surface topography and optionally a tertiary surface topography superimposed onto the secondary surface topography. Where the primary topography is formed by surface features at area scale a), a secondary topography may be provided according to area scale b) and/or c). Similarly, if the primary topography is formed by surface features at area scale b), a secondary topography may be provided according to area scale c). A tertiary surface topography may be provided according to area scale d).

Implant material according to the invention may optionally also comprise surface waviness, gradients or contours at a comparatively large-scale perspective on which the surface roughness features discussed herein are superimposed.

As explained above, surface roughness amongst other things is known to have an effect on cellular response upon implantation in the body. Surface roughness in the general micron-scale is thought to play a key role in disrupting the capsular formation and contraction by disrupting the alignment and organisation of fibroblasts. Moreover, the implant surfaces of the present invention may show one or more of improved cellular attachment, proliferation and survival and altered genotypic response. Data comparing implants of the present invention with "conventional" comparative smooth and textured implant surfaces (see cellular response data in examples) demonstrates that these valuable technical effects have been achieved.

In particular, the inventors have found that the novel textured surfaces exhibit diminished inflammatory genotype and cytokine profile for cells on the surface.

Without wishing to be bound by theory, the inventors propose that the improved results are a direct result of the novel surface roughness features of the invention. The present surfaces are on average comparatively rougher than commercial smooth implants, but significantly less rough than comparative rough (commercially available textured) implants. The inventors submit that the improved cellular proliferation exhibited by these novel implant surfaces is a direct result of this "tailored" surface roughness. In particular, whilst organised capsule formation and contracture may be prevented by the novel surfaces, the vertical height and sloped contours of the surfaces allow usual contact guidance and cellular mobility processes to continue, providing a largely natural environment for the cells and reducing the cell stress response. This was unexpected, especially given the abundance of textured implants having substantially greater roughness in comparison, especially open cell foams which often typically have surface roughness features at the 100 micron-1000 micron scale and which large scale roughness features were conventionally thought to be crucial to their function (see e.g. column 5, paragraph 63 of US2011/0276134).

Even more advantageously, the controlled texture roughness of the implant surfaces of the present claims not only means that reduced capsular contraction, enhanced cellular proliferation and immune response can be achieved, but the reduced level of roughness compared to conventional textured implants means that extensive cellular in-growth may not occur, meaning that the implant can be removed more easily later because very little of the patient's own tissue would also need to be surgically excised, minimising unnecessary tissue loss and the post-operative trauma.

The data obtained for the implant surfaces of the present claims also indicates the importance of nano-scale features to the cellular response. In particular, material of the invention prepared by a lower resolution fabrication method of the present invention (and so lacking in roughness features on the smaller nano-scale) showed similar potential compared to surfaces of the present invention having finer nano features prepared by a higher resolution casting method of the present invention), but surfaces having nano-features showed better cell proliferation and survival data. The inventors propose that this reflects the ability of the cells to recognise nano-scale features and in particular for the biomimetic nano-scale roughness features to produce a more natural environment and less stressed response.

Surface Roughness

Mean Surface Roughness (Sa)

In embodiments of any of the aspects herein, the implant material at an area scale of 1 mm×1 mm comprises a mean surface roughness Sa value of from 1 µm to 20 µm, suitably 1 µm to 15 µm, suitably 2 µm to 12 µm, suitably 3 µm to 9 µm, suitably 4 µm to 8 µm, for instance 5 to 7 µm. In embodiments, the surface roughness Sa value is 15 µm or less or less at this area scale, more typically less than 12 µm, suitably less than 10 µm, suitably less than 9 µm, such as less than 8 µm, preferably around 7 µm. In embodiments, the surface roughness Sa value is 1 µm or more at this area scale, suitably 2 µm or more, suitably 3 µm or more.

In embodiments of any of the aspects herein, the implant material at an area scale of 90 µm×90 µm comprises a mean surface roughness Sa value of from 0.1 µm to 5 µm, suitably 0.2 µm to 2 µm, suitably 0.2 µm to 1 µm, suitably 0.1 µm to 0.9 µm, for instance 0.2 µm to 0.8 µm, such as 0.3 µm to 0.7 µm, such as 0.4 to 0.6 µm. In embodiments, the surface roughness Sa value is 5 µm or less at this area scale, more typically less than 2 µm, suitably less than 1 µm, suitably less than 0.6 µm, such as about 0.5 µm. In embodiments, the surface roughness Sa value is 0.1 µm or more at this area scale, suitably 0.2 µm or more, suitably 0.3 µm or more, suitably 0.4 µm or more.

In embodiments of any of the aspects herein, the implant material at an area scale of 10 µm×10 µm comprises a mean surface roughness Sa value of from 10 nm to 1000 nm, suitably 10 nm to 500 nm, suitably 30 nm to 500 nm, suitably 30 nm to 200 nm, for instance 30 nm to 140 nm, such as 50 nm to 100 nm. In embodiments, the surface roughness Sa value is 300 nm or less at this area scale, suitably 200 nm or less, suitably 150 nm or less, e.g. about 65 nm to 100 nm. In embodiments, the surface roughness Sa value is 10 nm or more at this area scale, suitably 30 nm or more, suitably 40 nm or more, suitably 50 nm or more, suitably 60 nm or more, e.g. about 65 nm to 100 nm.

In embodiments of any of the aspects herein, the implant material at an area scale of 1 µm×1 µm comprises a mean surface roughness Sa value of from 2 nm to 15 nm, suitably 2 nm to 10 nm, suitably 2 nm to 9 nm, suitably 3 nm to 9 nm, for instance 4 nm to 7 nm, such as 5 nm to 7 nm. In embodiments, the surface roughness Sa value is 10 nm or less at this area scale, suitably 9 nm or less, suitably 8 nm or less, suitably 7 nm or less, e.g. about 4 nm to 7 nm. In embodiments, the surface roughness Sa value is 2 nm or more at this area scale, suitably 3 nm or more, suitably 4 nm or more, e.g. about 4 nm to 7 nm.

For example, in embodiments, the implant material comprises a mean surface roughness Sa value of:
a) from 4 μm to 8 μm at an area scale of 1 mm×1 mm; and/or
b) from 0.1 μm to 0.9 μm at an area scale of 90 μm×90 μm; and/or
c) from 10 nm to 200 nm at an area scale of 10 μm×10 μm; and/or
d) from 2 nm to 8 nm at an area scale of 1 μm×1 μm.

In embodiments, the implant material according to any of the aspects herein has a mean surface roughness Sa value of from 2 nm to 15 nm at an area scale of 1 μm×1 μm, for instance 3 nm to 10 nm, such as from 4 nm to 9 nm, e.g. around 6 nm. In typical embodiments, the surface roughness Sa value is 20 nm or less at this area scale, more typically less than 15 nm, such as less than 10 nm.

In preferred embodiment, the implant surface Sa value is substantially as disclosed in any one or more of FIGS. 16A to 18D, and 26A to 41.

Embodiments have, in addition to the Sa value(s) described above, one or more of the Sq value(s) described herein and/or one or more of the Sz value(s) described herein and/or one or more of the Ssk value(s) described herein and/or one or more of the kurtosis (Sku minus 3) value(s) described herein and/or one or more of the fractal dimension (FD) value(s) described herein and/or one or more of the surface linear auto correlation function (ACF) value(s) described herein.

Root Mean Square Height (Sq)

In embodiments of any of the aspects herein, the implant material at an area scale of 1 mm×1 mm comprises a root mean square height Sq value of from 2 μm to 30 μm, suitably 4 to 15 μm, such as from 5 to 10 μm. In embodiments, the Sq value is 30 μm or less, suitably 20 μm or less, suitably 15 μm or less at this area scale, more typically less than 12 μm, suitably 10 μm or less, suitably 9 μm or less, suitably 8 μm or less, e.g. 4 μm to 8 μm. In embodiments, the Sq value is 2 μm or more at this area scale, suitably 3 μm or more, suitably 4 μm or more, suitably 5 μm or more, e.g. 5 μm to 8 μm.

In embodiments of any of the aspects herein, the implant material at an area scale of 90 μm×90 μm comprises a root mean square height Sq value of from 0.2 μm to 5 μm, suitably 0.2 μm to 1.5 μm, suitably 0.3 μm to 1 μm, suitably 0.4 μm to 0.9 μm, suitably 0.5 to 0.8 μm, e.g. about 0.5 to 0.7 μm. In embodiments, the Sq value is 5 μm or less at this area scale, suitably 3 μm or less, suitably 2 μm or less, suitably 1.5 μm or less, suitably 1 μm or less, suitably 0.8 μm or less, suitably 0.7. In embodiments, the Sq value is 0.2 μm or more at this area scale, suitably 0.3 μm or more, suitably 0.4 μm or more, suitably 0.5 μm or more.

In embodiments of any of the aspects herein, the implant material at an area scale of 10 μm×10 μm comprises a root mean square height Sq value of from 20 nm to 250 nm, suitably 30 nm to 250 nm, suitably 40 nm to 250 nm, suitably 50 nm to 200 nm, suitably 60 nm to 200 nm, e.g. 80 nm to 140 nm. In embodiments, the Sq value is 250 nm or less at this area scale, suitably 200 nm or less, suitably 180 nm or less, suitably 160 nm or less, suitably 140 nm or less, suitably 130 nm or less. In embodiments, the Sq value is 20 nm or more at this area scale, suitably 30 nm or more, suitably 40 nm or more, suitably 50 nm or more, suitably 60 nm or more, suitably 70 nm or more, suitably 80 nm or more.

In embodiments of any of the aspects herein, the implant material at an area scale of 1 μm×1 μm comprises a root mean square height Sq value of from 2 nm to 20 nm, suitably 2 nm to 12 nm, suitably 3 nm to 10 nm, suitably 4 nm to 10 nm, suitably 5 nm to 10 nm, suitably 6 nm to 10 nm, e.g. 6 nm to 9 nm. In embodiments, the Sq value is 12 nm or less at this area scale, suitably 11 nm or less, suitably 10 nm or less, suitably 9 nm or less, suitably 8 nm or less. In embodiments, the Sq value is 2 nm or more at this area scale, suitably 3 nm or more, suitably 4 nm or more, suitably 5 nm or more, suitably 6 nm or more, suitably 7 nm or more.

For example, in embodiments, the implant material comprises a root mean square height Sq value of:
a) from 2 μm to 20 μm at an area scale of 1 mm×1 mm;
b) from 0.2 μm to 1.5 μm at an area scale of 90 μm×90 μm; and/or
c) from 20 nm to 250 nm at an area scale of 10 μm×10 μm; and/or
d) from 4 nm to 12 nm at an area scale of 1 μm×1 μm.

In preferred embodiments, the implant surface Sq value is substantially as disclosed in any one or more of FIGS. 16A to 18D, and 26A to 41.

Embodiments have, in addition to the Sq value(s) described above, one or more of the Sa value(s) described herein and/or one or more of the Sz value(s) described herein and/or one or more of the Ssk value(s) described herein and/or one or more of the kurtosis (Sku minus 3) value(s) described herein and/or one or more of the fractal dimension (FD) value(s) described herein and/or one or more of the surface linear (horizontal or vertical) auto correlation function (ACF) value(s) described herein.

Maximum Peak Height to Trough Depth (Sz)

In embodiments of any of the aspects herein, the implant material at an area scale of 1 mm×1 mm comprises a mean Sz value of from 10 μm to 80 μm, suitably 10 μm to 60 μm, suitably 20 μm to 60 μm, suitably 30 μm to 60 μm, suitably 30 to 50 μm, e.g. 35 μm to 45 μm. In embodiments, the Sz value is 80 μm or less at this area scale, suitably 60 μm or less, suitably 55 μm or less, suitably 50 μm or less, suitably 48 μm or less, suitably 45 μm or less. In embodiments, the Sz value is 5 μm or more at this area scale, suitably 10 μm or more, suitably 15 μm or more, suitably 20 μm or more, suitably 30 μm or more, suitably 35 μm or more, suitably 40 μm or more.

In embodiments of any of the aspects herein, the implant material at an area scale of 90 μm×90 μm comprises a mean Sz value of from 1 μm to 10 μm, suitably 1 μm to 8 μm, suitably 2 μm to 8 μm, suitably 2 μm to 7 μm, suitably 3 μm to 6 μm, e.g. about 3 μm to 5 μm. In embodiments, the Sz value is 10 μm or less at this area scale, suitably 8 μm or less, suitably 7 μm or less, suitably 6 μm or less, suitably 5 μm or less. In embodiments, the Sz value is 1 μm or more at this area scale, suitably 2 μm or more, suitably 3 μm or more.

In embodiments of any of the aspects herein, the implant material at an area scale of 10 μm×10 μm comprises a mean Sz value of from 0.1 μm to 2 μm, suitably 0.1 μm to 1.5 μm, suitably 0.3 μm to 1.2 μm, suitably 0.4 μm to 0.8 μm, e.g. about 0.5 μm to 0.8 μm. In embodiments, the Sz value is 2 μm or less at this area scale, suitably 1.5 μm or less, suitably 1.2 μm or less, suitably 1 μm or less, suitably 0.9 μm or less, suitably 0.8 μm or less.

In embodiments of any of the aspects herein, the implant material at an area scale of 1 µm×1 µm comprises a mean Sz value of from 10 nm to 100 nm, suitably 30 nm to 70 nm, suitably 40 nm to 65 nm, suitably 40 nm to 60 nm, suitably 40 nm to 55 nm, e.g. about 45 nm to 55 nm. In embodiments, the Sz value is 70 nm or less at this area scale, suitably 65 nm or less, suitably 60 nm or less, suitably 55 nm or less. In embodiments, the Sz value is 30 nm or more at this area scale, suitably 35 nm or more, suitably 40 nm or more, suitably 45 nm or more.

For example, in embodiments, the implant material comprises an Sz value of:
a) from 10 µm to 60 µm, optionally 30 µm to 50 µm at an area scale of 1 mm×1 mm;
b) from 2 µm to 8 µm at an area scale of 90 µm×90 µm; and/or
c) from 0.1 µm to 1.5 µm at an area scale of 10 µm×10 µm; and/or
d) from 30 nm to 70 nm at an area scale of 1 µm×1 µm.

In preferred embodiments, the implant surface Sz value is substantially as disclosed in any one or more of FIGS. 16A to 18D, and 26A to 41.

Embodiments have, in addition to the Sz value(s) described above, one or more of the Sa value(s) described herein and/or one or more of the Sq value(s) described herein and/or one or more of the Ssk value(s) described herein and/or one or more of the kurtosis (Sku minus 3) value(s) described herein and/or one or more of the fractal dimension (FD) value(s) described herein and/or one or more of the surface linear (horizontal or vertical) auto correlation function (ACF) value(s) described herein.

Skewness (Ssk)

In embodiments of any of the aspects herein the ratio of the average peak height to average trough depth at the respective area scale is from 2:3 to 3:2, optionally from 4.5:5.5 to 5.5:4.5, optionally wherein the average peak height and average trough height are substantially equal.

In embodiments, the distribution of surface peak relative to trough heights is substantially symmetrical about the mean height value at the respective scales, optionally wherein the surface heights are substantially normally distributed about the mean height value at the respective scales.

In embodiments of any of the aspects herein, the implant material at an area scale of 1 mm×1 mm comprises a mean Ssk value of from −1.0 to 1.0, suitably −0.8 to 0.8, suitably −0.7 to 0.7, suitably −0.5 to 0.5, suitably −0.4 to 0.4, suitably −0.3 to 0.3, suitably −0.2 to 0.2, suitably −0.15 to 0.15, e.g. about zero. In embodiments, the Ssk value is 1.0 or less at this area scale, suitably 0.8 or less, suitably 0.6 or less, suitably 0.5 or less, suitably 0.4 or less, suitably 0.3 or less, suitably 0.25 or less, suitably 0.2 or less, suitably 0.15 or less. In embodiments, the Ssk value is −0.5 or more at this area scale, suitably −0.4 or more, suitably −0.3 or more, suitably −0.2 or more, suitably −0.1 or more, suitably 0 or more, suitably 0.05 or more.

In embodiments of any of the aspects described herein, the implant material at an area scale of 90 µm×90 µm comprises a mean Ssk value of from −1.0 to 1.0, suitably −0.9 to 0.9, suitably −0.8 to 0.8, suitably −0.6 to 0.6, suitably −0.4 to 0.4, suitably −0.3 to 0.3, suitably −0.2 to 0.2, suitably −0.15 to 0.15, e.g. around zero. In embodiments, the Ssk value is 1.0 or less at this area scale, suitably 0.8 or less, suitably 0.6 or less, suitably 0.4 or less, suitably 0.3 or less, suitably 0.25 or less, suitably 0.2 or less, suitably 0.18 or less, suitably 0.15 or less. In embodiments, the Ssk value is −1.0 or more at this area scale, suitably −0.8 or more, suitably −0.6 or more, suitably −0.4 or more, suitably −0.2 or more, suitably −0.1 or more, suitably −0.08 or more.

In embodiments of any aspects herein, the implant material at an area scale of 10 µm×10 µm comprises a mean Ssk value of from −0.8 to 0.8, suitably −0.7 to 0.7, suitably −0.6 to 0.6, suitably −0.5 to 0.5, suitably −0.4 to 0.4, suitably −0.3 to 0.3, suitably −0.2 to 0.2, e.g. around zero. In embodiments, the Ssk value is 0.8 or less at this area scale, suitably 0.7 or less, suitably 0.6 or less, suitably 0.5 or less, suitably 0.4 or less, suitably 0.3 or less, suitably 0.2 or less, suitably 0.15 or less. In embodiments, the Ssk value is −0.8 or more at this area scale, suitably −0.7 or more, suitably −0.6 or more, suitably −0.5 or more, suitably −0.4 or more, suitably −0.3 or more, suitably −0.2 or more, suitably −0.18 or more, suitably −0.15 or more.

In embodiments of any of the aspect or embodiment described herein, the implant material at an area scale of 1 µm×1 µm comprises a mean Ssk value of from −0.5 to 0.5, suitably −0.4 to 0.4, suitably −0.3 to 0.3, suitably −0.2 to 0.2, suitably −0.1 to 0.1, suitably −0.05 to 0.05, e.g. around zero. In embodiments, the Ssk value is 0.5 or less at this area scale, suitably 0.4 or less, suitably 0.3 or less, suitably 0.2 or less, suitably 0.1 or less, suitably 0.08 or less, suitably 0.06 or less. In embodiments, the Ssk value is −0.5 or more at this area scale, suitably −0.4 or more, suitably −0.3 or more, suitably −0.2 or more, suitably −0.1 or more, suitably −0.08 or more, suitably −0.06 or more.

The invention thus provides an implant material according to any aspect or embodiment herein wherein the surface at the respective area scales has a mean surface skewness Ssk value of:
a) from −1.0 to +1.0, suitably −0.2 to +0.2 at an area scale of 1 mm×1 mm; and/or
b) from −1.0 to +1.0, suitably −0.2 to +0.2 at an area scale of 90 µm×90 µm; and/or
c) from −0.7 to +0.7, suitably −0.2 to +0.2 at an area scale of 10 µm×10 µm; and/or
d) from −0.5 to +0.5, suitably −0.1 to 0.1 at an area scale of 1 µm×1 µm.

In preferred embodiments, the implant material has a mean surface skewness Ssk value of −0.2 to 0.2, suitably −0.15 to 1.5, suitably about zero at each respective area scale.

In embodiments, the implant surface Ssk value is substantially as disclosed in any one or more of FIGS. 16A to 18D, and 26A to 41.

In embodiments of any of the aspects herein 40% to 60% of the surface at the respective area scale consists of peaks, optionally wherein from 45% to 55% of the surface at the respective area scale consists of peaks, such as around 50% of the surface at the respective area scale consists of peaks.

In embodiments of any of the aspects herein, from 40% to 60% of the surface at the respective area scale consists of troughs, optionally wherein from 45% to 55% of the surface at the respective area scale consists of troughs, such as around 50%.

Embodiments have, in addition to the Ssk value(s) described above, one or more of the Sa value(s) described herein and/or one or more of the Sq value(s) described herein and/or one or more of the Sz value(s) described herein and/or one or more of the kurtosis (Sku minus 3) value(s) described herein and/or one or more of the fractal dimension (FD) value(s) described herein and/or one or more of the surface linear (horizontal or vertical) auto correlation function (ACF) value(s) described herein.

Kurtosis and Mean Excess Kurtosis Value (Sku Minus 3)

The invention provides an implant material according to any aspect or embodiment disclosed herein wherein the surface is substantially free of peaks and troughs that deviate significantly from the mean surface height roughness Sa value at the respective areas scale. In embodiments, the surface is substantially free of peaks or troughs which deviate from the mean surface height roughness Sa value by more than 200% of the mean surface height value at the respective area scales, suitably by more than 150% of the mean surface height value at the respective area scales, such as by more than 100%. In this context, substantially free means that less than 2%, suitably less than 1%, preferably less than 0.5%, of the implant material surface area consists of such significantly deviating peaks.

In embodiments, the peak profile of the implant material surface according to any aspect herein is substantially rounded, squashed or flattened, e.g. compared to Mentor Siltex textured implant surfaces.

In embodiments of any of the aspect or embodiment described herein, the implant material at an area scale of 1 mm×1 mm comprises a mean excess kurtosis value Sku minus 3 of from −1.5 to 1.5, suitably −1.0 to 1.0, suitably −0.7 to 0.7, suitably −0.5 to 0.5, suitably −0.3 to 0.3, suitably −0.2 to 0.2. In embodiments, the Sku minus 3 value is 1.5 or less at this area scale, suitably 1.0 or less, suitably 0.8 or less, suitably 0.7 or less, suitably 0.6 or less, suitably 0.5 or less, suitably 0.4 or less, suitably 0.3 or less, suitably 0.25 or less, suitably 0.2 or less, suitably 0.18 or less, suitably 0.15 or less. In embodiments, the Skuu minus 3 value is −1.5 or more at this area scale, suitably −1.0 or more, suitably −0.8 or more, suitably −0.7 or more, suitably −0.6 or more, suitably −0.5 or more, suitably −0.4 or more, suitably −0.3 or more, suitably −0.2 or more, suitably −0.15 or more, suitably −0.1 or more, suitably −0.05 or more, suitably 0 or more.

In embodiments of any of the aspect or embodiment described herein, the implant material at an area scale of 90 μm×90 μm comprises a mean excess kurtosis value Sku minus 3 of from −1.5 to 1.5, suitably −1.0 to 1.0, suitably −0.7 to 0.7, suitably −0.5 to 0.5, suitably −0.3 to 0.3, suitably −0.2 to 0.2. In embodiments, the Sku minus 3 value is 1.5 or less at this area scale, suitably 1.0 or less, suitably 0.8 or less, suitably 0.7 or less, suitably 0.6 or less, suitably 0.5 or less, suitably 0.4 or less, suitably 0.3 or less, suitably 0.25 or less, suitably 0.2 or less, suitably 0.18 or less, suitably 0.15 or less. In embodiments, the Skuu minus 3 value is −1.5 or more at this area scale, suitably −1.0 or more, suitably −0.8 or more, suitably −0.7 or more, suitably −0.6 or more, suitably −0.5 or more, suitably −0.4 or more, suitably −0.3 or more, suitably −0.2 or more, suitably −0.15 or more, suitably −0.1 or more, suitably −0.05 or more, suitably 0 or more.

In embodiments of any of the aspect or embodiment described herein, the implant material at an area scale of 10 μm×10 μm comprises a mean excess kurtosis value Sku minus 3 of from −1.5 to 1.5, suitably −1.0 to 1.0, suitably −0.7 to 0.7, suitably −0.5 to 0.5, suitably −0.3 to 0.3, suitably −0.2 to 0.2. In embodiments, the Sku minus 3 value is 1.5 or less at this area scale, suitably 1.0 or less, suitably 0.8 or less, suitably 0.7 or less, suitably 0.6 or less, suitably 0.5 or less, suitably 0.4 or less, suitably 0.3 or less, suitably 0.25 or less, suitably 0.2 or less, suitably 0.18 or less, suitably 0.15 or less. In embodiments, the Skuu minus 3 value is −1.5 or more at this area scale, suitably −1.0 or more, suitably −0.8 or more, suitably −0.7 or more, suitably −0.6 or more, suitably −0.5 or more, suitably −0.4 or more, suitably −0.3 or more, suitably −0.2 or more, suitably −0.18 or more, suitably −0.16 or more, suitably −0.15 or more, suitably −0.1 or more, suitably −0.05 or more, suitably 0 or more.

In embodiments of any of the aspect or embodiment described herein, the implant material at an area scale of 1 μm×1 μm comprises a mean excess kurtosis value Sku minus 3 of from −1.5 to 1.5, suitably −1.0 to 1.0, suitably −0.8 to 0.8, suitably −0.7 to 0.7, suitably −0.5 to 0.5, suitably −0.3 to 0.3, suitably −0.2 to 0.2. In embodiments, the Sku minus 3 value is 1.5 or less at this area scale, suitably 1.0 or less, suitably 0.8 or less, suitably 0.7 or less, suitably 0.6 or less, suitably 0.5 or less, suitably 0.4 or less, suitably 0.3 or less, suitably 0.25 or less, suitably 0.2 or less, suitably 0.18 or less, suitably 0.15 or less. In embodiments, the Skuu minus 3 value is −1.5 or more at this area scale, suitably −1.0 or more, suitably −0.8 or more, suitably −0.7 or more, suitably −0.6 or more, suitably −0.5 or more, suitably −0.4 or more, suitably −0.3 or more, suitably −0.2 or more, suitably −0.18 or more, suitably −0.16 or more, suitably −0.15 or more, suitably −0.1 or more, suitably −0.05 or more, suitably 0 or more.

In embodiments of any of the aspects herein is provided an implant material having a mean excess kurtosis value (Sku minus 3) of:
a) from −1.0 to +1.0, suitably −0.2 to +0.2 at an area scale of 1 mm×1 mm; and/or
b) from −1.0 to +1.0, suitably −0.2 to +0.2 at an area scale of 90 μm×90 μm; and/or
c) from −1.0 to +1.0, suitably −0.2 to +0.2 at an area scale of 10 μm×10 μm; and/or
d) from −1.5 to +1.5, suitably −0.1 to +0.1 at an area scale of 1 μm×1 μm.

In preferred embodiments, the implant material has a mean excess kurtosis value (Sku minus 3) of about zero at any one or more of the respective area scales.

In embodiments, the implant surface kurtosis value is substantially as disclosed in any one or more of FIGS. 16A to 18D, and 26A to 41.

Embodiments have, in addition to the kurtosis (Sku minus 3) value(s) described above, one or more of the Sa value(s) described herein and/or one or more of the Sq value(s) described herein and/or one or more of the Sz value(s) described herein and/or one or more of the Ssk value(s) described herein and/or one or more of the fractal dimension (FD) value(s) described herein and/or one or more of the surface linear (horizontal or vertical) auto correlation function (ACF) value(s) described herein.

Fractal Dimension (FD)

In the aspects and embodiments herein, the implant material may have a fractal dimension at the respective area scale of from 2.0 to 2.6. Suitably, the fractal dimension at the respective area scale is from 2.1 to 2.5, suitably 2.2 to 2.4.

In embodiments of any of the aspect or embodiment described herein, the implant material at an area scale of 1 mm×1 mm comprises a fractal dimension value FD of from 2.0 to 2.6, suitably 2.1 to 2.5, suitably 2.2 to 2.4. In embodiments the FD value is 2.6 or less at this area scale, suitably 2.5 or less, suitably 2.45 or less, suitably 2.4 or less. In embodiments the FD value is 2.0 or more at this area scale, suitably 2.1 or more, suitably 2.2 or more, suitably 2.25 or more.

In embodiments of any of the aspect or embodiment described herein, the implant material at an area scale of 90 μm×90 μm comprises a fractal dimension value FD of from 2.0 to 2.6, suitably 2.1 to 2.5, suitably 2.2 to 2.4. In embodiments the FD value is 2.6 or less at this area scale, suitably 2.5 or less, suitably 2.45 or less, suitably 2.4 or less, suitably 2.35 or less. In embodiments the FD value is 2.0 or more at this area scale, suitably 2.1 or more, suitably 2.2 or more, suitably 2.25 or more.

In embodiments of any of the aspect or embodiment described herein, the implant material at an area scale of 10 μm×10 μm comprises a fractal dimension value FD of from 2.0 to 2.6, suitably 2.1 to 2.5, suitably 2.2 to 2.4. In embodiments the FD value is 2.6 or less at this area scale, suitably 2.5 or less, suitably 2.45 or less, suitably 2.4 or less, suitably 2.35 or less. In embodiments the FD value is 2.0 or more at this area scale, suitably 2.1 or more, suitably 2.2 or more, suitably 2.25 or more.

In embodiments of any of the aspect or embodiment described herein, the implant material at an area scale of 1 μm×1 μm comprises a fractal dimension value FD of from 2.0 to 2.6, suitably 2.1 to 2.5, suitably 2.2 to 2.4. In embodiments the FD value is 2.6 or less at this area scale, suitably 2.5 or less, suitably 2.45 or less, suitably 2.4 or less, suitably 2.35 or less. In embodiments the FD value is 2.0 or more at this area scale, suitably 2.1 or more, suitably 2.2 or more, suitably 2.25 or more.

In preferred embodiments, all of the respective area scales selected from a) to d) have a fractal dimension as described above. Such preferred implant materials of the invention are therefore self-similar in the respective area dimensions (because the fractal dimension at each area scale is similar). This mimics the fractal arrangements of tissue surfaces in the body, e.g. in the BM layer of the dermis of the skin and is proposed to provide a more natural biomimetic environment for cellular attachment and proliferation.

In preferred embodiments, the implant material according to any of the aspects herein has a fractal dimension substantially as defined in any one or more of FIGS. 16A to 18D, and 24A to 28B.

Embodiments have, in addition to the Fractal Dimension described above, one or more of the Sa value(s) described herein and/or one or more of the Sq value(s) described herein and/or one or more of the Sz value(s) described herein and/or one or more of the Ssk value(s) described herein and/or one or more of the kurtosis (Sku minus 3) value(s) described herein and/or one or more of the surface linear (horizontal or vertical) auto correlation function (ACF) value(s) described herein.

Surface Linear (Horizontal or Vertical) Auto Correlation Function (ACF)

The correlation length is defined using a Gaussian fit in accordance with Equation 1 to the first half of data points in the ACF. An example of such fit being illustrated in FIG. 42.

$$G(\tau_x, \tau_y) = \int\int_{-\infty}^{\infty} z_1 z_2 w(z_1, z_2, \tau_x, \tau_y) dz_1 dz_2 \quad \text{Equation 1}$$
$$= \lim_{S\to\infty} \frac{1}{S} \int\int_S \xi(x_1, y_1)\xi(x_1+\tau_x, y_1+\tau_y) dx_1 dy_1$$

where $z_1$ and $z_2$ are the values of heights at points $(x_1, y_1)$, $(x_2, y_2)$; furthermore, $\tau_x = x_1 - x_2$ and $\tau_y = y_1 - y_2$. The function $w(z_1, z_2, \tau_x, \tau_y)$ denotes the two-dimensional probability density of the random function $\xi(x, y)$ corresponding to points $(x_1, y_1)$, $(x_2, y_2)$, and the distance between these points τ. (Gwyddion user guide; http://gwyddion.net/documentation/user-guide-en/).

Reference herein to "Horizontal" and "Vertical" in the context of linear auto correlation function is a reference to the plan (planar) view, i.e. the X-axis (horizontal) and Y-axis (vertical).

In embodiments of any of the aspect or embodiment described herein, the implant material at an area scale of 1 mm×1 mm has a linear autocorrelation length of from 20 μm to 200 μm, suitably 30 μm to 200 μm, suitably 50 μm to 200 μm, suitably 60 μm to 190 μm. In embodiments the linear autocorrelation length is 200 μm or less at this area scale, suitably 190 μm or less, suitably 180 μm or less. In embodiments the autocorrelation length is 20 μm or more at this area scale, suitably 25 μm or more, suitably 30 μm or more, suitably 35 μm or more.

In embodiments of any of the aspect or embodiment described herein, the implant material at an area scale of 90 μm×90 μm has a linear autocorrelation length of from 3 μm to 20 μm, suitably 3 μm to 15 μm, suitably 3 μm to 13 μm, suitably 4 μm to 13 μm, suitably 5 μm to 11 μm, suitably 5 μm to 10 μm. In embodiments the linear autocorrelation length is 20 μm or less at this area scale, suitably 15 μm or less, suitably 13 μm or less, suitably 12 μm or less, suitably 11 μm or less, suitably 10 μm or less, suitably 9 μm or less. In embodiments the autocorrelation length is 2 μm or more at this area scale, suitably 3 μm or more, suitably 4 μm or more, suitably 5 μm or more, suitably 5.5 μm or more, suitably 6 μm or more.

In embodiments of any of the aspect or embodiment described herein, the implant material at an area scale of 10 μm×10 μm has a linear autocorrelation length of from 0.5 μm to 2.5 μm, suitably 0.5 μm to 2 μm, suitably 0.6 μm to 2 μm, suitably 0.6 μm to 1.8 μm, suitably 0.7 μm to 1.8 μm. In embodiments the linear autocorrelation length is 2.5 μm or less at this area scale, suitably 2 μm or less, suitably 1.9 μm or less, suitably 1.8 μm or less, suitably 1.75 μm or less, suitably 1.7 μm or less, suitably 1.65 μm or less, suitably 1.6 or less, suitably 1.6 or less, suitably 1.55 μm or less, suitably 1.5 μm or less. In embodiments the autocorrelation length is 0.5 μm or more at this area scale, suitably 0.55 μm or more, suitably 0.6 μm or more, suitably 0.65 μm or more, suitably 0.7 μm or more, suitably 0.75 μm or more, suitably 0.8 μm or more, suitably 0.85 μm or more.

In embodiments of any of the aspect or embodiment described herein, the implant material at an area scale of 1 μm×1 μm has a linear autocorrelation length of from 40 nm to 200 nm, suitably 20 nm to 180 nm, suitably 40 nm to 180 nm, suitably 60 nm to 180 nm, suitably 50 nm to 150 nm, suitably 60 nm to 130 nm. In embodiments the linear autocorrelation length is 200 nm or less at this area scale, suitably 190 nm or less, suitably 180 nm or less, suitably 175 nm or less, suitably 170 nm or less, suitably 165 nm or less, suitably 160 nm or less, suitably 155 nm or less, suitably 155 nm or less, suitably 150 nm or less, suitably 145 nm or less, suitably 140 nm or less, suitably 135 nm or less, suitably 130 nm or less. In embodiments the autocorrelation length is 40 nm or more at this area scale, suitably 45 nm or more, suitably 50 nm or more, suitably 55 nm or more, suitably 60 nm or more, suitably 65 nm or more, suitably 70 nm or more, suitably 75 nm or more, suitably 80 nm or more, suitably 85 nm or more.

In embodiments, the implant material has a surface having a linear correlation length of:
a) from 20 μm to 200 μm, suitably 60 μm to 190 μm, at an area scale of 1 mm×1 mm; and/or
b) from 3 μm to 15 μm, suitably 5 μm to 13 μm at an area scale of 90 μm×90 μm; and/or
c) from 0.5 μm to 2.5 μm, suitably 0.7 μm to 2 μm at an area scale of 10 μm×10 μm and/or
d) from 40 nm to 150 nm, suitably 60 nm to 130 nm at an area scale of 1×1 μm.

In embodiments, the ranges and values given above are the horizontal auto correlation length. Thus, embodiments have a horizontal auto correlation length satisfying the ranges given above.

In embodiments, the values given above are the vertical auto correlation length. Thus, embodiments have a vertical auto correlation length satisfying the ranges given above.

In embodiments, the values given above are for both the horizontal auto correlation length and the vertical auto correlation length. Thus, embodiments have a horizontal auto correlation length satisfying the ranges given above and a vertical auto correlation length satisfying the ranges given above.

In embodiments, the horizontal auto correlation length is:
a) from 20 μm to 200 μm, suitably 60 μm to 190 μm, at an area scale of 1 mm×1 mm; and/or
b) from 3 μm to 15 μm, suitably 5 μm to 13 μm at an area scale of 90 μm×90 μm; and/or
c) from 0.5 μm to 2.5 μm, suitably 0.7 μm to 2.0 μm at an area scale of 10 μm×10 μm and/or
d) from 40 nm to 150 nm, suitably 60 nm to 130 nm at an area scale of 1×1 μm.

In embodiments, the vertical autocorrelation length is:
a) from 20 μm to 200 μm, suitably 60 μm to 190 μm, at an area scale of 1 mm×1 mm; and/or
b) from 3 μm to 15 μm, suitably 5 μm to 13 μm at an area scale of 90 μm×90 μm; and/or
c) from 0.5 μm to 2.5 μm, suitably 0.7 μm to 2.0 μm at an area scale of 10 μm×10 μm and/or
d) from 40 nm to 150 nm, suitably 60 nm to 130 nm at an area scale of 1×1 μm.

In embodiments of any of the aspects herein, the implant material at an area scale of 1 mm×1 mm has a minimum in the ACF from 200 to 600 μm and optionally a second maximum from 500 to 850 μm.

In embodiments of any of the aspects herein, the implant material at an area scale of 90 μm×90 μm has a minimum in the ACF from 15 to 50 μm and optionally a second maximum from 50 to 85 μm.

In embodiments of any of the aspects herein, the implant material at an area scale of 10 μm×10 μm has a minimum in the ACF from 1 to 6 μm and optionally a second maximum from 6 to 9 μm.

In embodiments of any of the aspects herein, the implant material at an area scale of 1×1 μm may have a minimum in the ACF from 0.1 to 0.6 μm and optionally a second maximum from 0.6 to 0.9 μm.

In embodiments, the implant material according to any of the aspects herein has a first minimum and optionally a second maximum in the ACF substantially as described herein in FIG. 42.

In embodiments at least half, preferably more than half, more preferably substantially all, most preferably all of the peaks and troughs of the surfaces of the invention have a gradually sloped gradient. In preferred embodiments, the textured surfaces of the invention are substantially free from steep slopes or side-walls (such as slopes having an incline of around 60-90%). This feature has the advantage of improving cellular mobility and survival by preventing cells becoming trapped within troughs in the surface on implantation.

Preferably the surfaces of the invention are substantially free, suitably free from open cell textures.

Implant Material

In embodiments of any of the aspects herein the implant material comprises, suitably comprises as a major component (e.g. at least 50 wt % of the total weight of the implant material, preferably at least 60 wt %, more preferably at least 70 wt %, more preferably at least 80 wt %, more preferably at least 90 wt %) in embodiments consist substantially of, in typical embodiments consist of, a suitable biocompatible material.

Suitably the material is capable of being shaped, e.g. by casting etching and/or moulding into a textured surface. Suitably, the material may comprise suitably comprises as a major component (e.g. at least 50 wt % of the total weight of the implant material, preferably at least 60 wt %, more preferably at least 70 wt %, more preferably at least 80 wt %, more preferably at least 90 wt %, more preferably at least 95 wt %, more preferably at least 99 wt %) in embodiments consist substantially of, typically consist of, a biocompatible synthetic polymer, suitably an organo-silicon polymer, preferably a silicone, and more preferably polydimethylsiloxane (PDMS).

It is particularly preferred that the surface of the implant material for which surface roughness parameters are specified herein (i.e. the surface intended to contact the patient's tissue, i.e. the tissue-engaging surface) comprises the above-mentioned biocompatible synthetic polymer. Indeed, as noted above, suitably the surface consists substantially of an organo-silicon polymer, preferably PDMA. Thus, in embodiments, the surface (tissue-engaging surface) is a textured organo-silicon surface, the texture being as described herein.

Suitably the composition of the implant material is substantially homogeneous, especially in a depth direction from the surface (tissue-engaging surface) into the bulk material.

The implant material suitably forms at least part of the surface layer of the relevant implant. Thus, surfaces of implants of the invention may partly comprise conventional implant surfaces as well as the novel and advantageous surfaces described herein. In embodiments, the implant material surfaces of the invention described herein forms at least half, in suitable embodiments more than half, preferably substantially all (e.g. at least 90%, 95%, 98% or 99% by area of the implant surface) of the tissue contacting surface of the implant, such as wherein the tissue contacting surface of the implant consists of said implant material. The material comprising the surfaces of the invention may be different to other materials in the implant or may be the same.

Thus the implant may comprise an underlayer layer of the same of different material to the implant surface layer of the invention.

The implant may be any suitable implant capable of insertion into a patient, preferably a prosthetic implant, optionally an implant for internal insertion beneath the skin surface of a patient, more preferably a breast implant.

The implant materials of the present invention are preferably configured so as to be inserted subcutaneously within a patient or may be administered externally. Preferably the implant is administered (is intended to be located) internally, e.g. subcutaneously.

Templates

In a further aspect of the invention is provided a template for use in preparing an implant material according to any aspect or embodiment herein. Suitably, said template comprises a textured surface as described according to any aspect or embodiment herein, or a negative (e.g. an inverse cast) of a textured surface as described herein. The template may typically comprise the 3-dimensional information, i.e. X,Y,Z information, corresponding to the implant material surface of the invention as defined according to any aspect and embodiment herein. In embodiments, the template is a stamp or mould, e.g. a stamp for imprinting a surface texture of the invention onto an implant surface or moulding the implant surface, optionally wherein the stamp or mould is a silicone stamp or mould. Thus, a surface may be stamped or moulded a number of times to provide an implant material having a surface as defined above. In embodiments, the template itself is a mould. The use of moulds is beneficial as they can be used to manufacture a large number of implants quickly.

Methods

In an aspect of the invention is provided a method of preparing an implant material having a textured surface comprising the steps of acquiring spatial data in the X, Y and Z dimensions (i.e. three-dimensional spatial data) from a tissue surface and using said spatial data to create the textured surface of the implant.

Suitably, the use of the spatial data further comprises the step of processing the spatial data and using the processed data to create the textured surface of the implant. Preferably the textured surface is an irregular textured surface.

The inventors thus propose the acquisition of 3D image/topography data corresponding to a tissue surface for reproduction on (formation of) an implant surface. This approach represents a considerable departure from conventional approaches to texturising implant surfaces, which are largely based on trial and error application of crude and often irreproducible methods which do not provide suitable control of the implant surfaces produced (e.g. by making open cell foam or by texturising using salt methods).

In embodiments, the step of acquiring the spatial X,Y,Z data is performed by any suitable contact or non-contact profilometer, suitably by atomic force microscopy, 3D laser scanner or optical profiler. Preferably, atomic force microscopy is used.

In embodiments, the step of creating the textured surface using the spatial X,Y,Z data includes three dimensional printing or photolithography or E-beam lithography, particularly optical photolithography, e.g. UV lithography. The level of resolution which can be achieved in the implant surfaces using a lithography method of the invention (see, e.g. Example 1) may be adjusted by a number of steps in the manufacture method. For instance, AFM scanners typically do not allow measurement of multiple 10's of microns in vertical scale. The grayscale lithography method as disclosed herein (see Example 1) is capable of reproducing lateral resolution of ~500 nm and thus is excellent as a method of reproducing micro scale and larger nano-scale features in surfaces of the present invention but excluding nano-scale features and long distance waviness features, etc. Thus, in an embodiment, the method includes the step of processing the 3D data (spatial X,Y,Z) by converting, suitably digitally converting the respective data to a form of data that can be read by a maskless lithography system. In an embodiment, the processing step includes formation of a two or more 8 bit (or optionally 16 bit) grayscale image wherein the 256 (e.g. or optionally 65536) different grayscale intensities corresponds to changes in vertical height of a measured surface. Alternatively or additionally, the processing step includes joining two or more grayscale images (maps) to form a mosaic montage of surface images prior to applying the image to a surface, for example prior to assigning a number of radiation doses on every pixel and thus controlling the exposure of the photoresist.

Use of such methods thus allows the production of controlled irregular surface features in an implant surface, which are, based on the reproduction of surface roughness features taken from a natural cellular environment and not from surfaces manufactured by the crude and uncontrolled ways reported in prior art. The method is more versatile than prior art methods and adaptation of the digital X,Y,Z information can provide not only the cell topography itself, but a variety of surface topographies using the tissue surface features as the original inspiration. Processing and manipulation of the surface data during the lithography or printing allows for reproduction of an endless range of surface designs. FIG. 25 describes a surface produced according to the grayscale method compared with natural material to show the similarities.

Use of Electron Beam (E-beam) Lithography may allow the reproduction of features that are <50 nm in lateral resolution. Thus, in an embodiment, the process of forming the surface of the invention from using the spatial X,Y,Z data includes using Electron Beam (E-beam) Lithography.

In embodiments, the method further comprises using the spatial X,Y,Z data to expose a photoresist (for example an E-beam photoresist) comprising the respective X,Y,Z information.

The method suitably includes use of the exposed and developed photoresist (for example an E-beam resist) to form the textured surface. The step of using the exposed and developed photoresist to transfer the textured surface onto a template may optionally comprise using an etching method, optionally deep reactive ion etching.

Embodiments of the method include use of the spatial X,Y,Z data to expose the photoresist and/or an e-beam resist comprising using the spatial X,Y,Z data to instruct the delivery of varying doses of radiation to a photoresist and/or E-beam resist surface so as to expose a photoresist and/or E-beam resist comprising the respective X,Y,Z information. Usually photolithography methods for preparing 3D features in objects (such as commonly used in the semiconductor industry) use a graded photomask to control the relative intensity of radiation received by various parts of the photoresist during the photolithography step. However, it is expensive and time-consuming to prepare such photomasks and once made, they cannot be varied and must be used to make a range of identical patterns. To the contrary, the use of the X,Y,Z data (e.g. the colour or grayscale depiction of peak-trough height) to control the relative intensity of radiation received at a given point of the photoresist (such as by using laserwriter configured to read such grayscale data) can advantageously allow for the exposure of a photoresist having, after development, the surface features directly rather than using a photomask. In other words, in embodiments, the lithography method is a maskless lithography method.

In embodiments, the step of preparing the photoresist includes increasing or decreasing the scale of the original X, Y and/or Z parameters for reproduction in the photoresist. This may be used advantageously if the photoresist needs to be thinner in the vertical direction that the vertical features of the surface being reproduced. The features may this be scaled up again during another step, such as using etching, e.g. deep reactive ion etching.

In another aspect is a method of preparing an implant material having a textured surface comprising the step of making a cast of a textured tissue surface, the cast containing spatial data representing the X,Y and Z dimensions and using said cast to make the textured implant material.

Casting of the tissue surface (see Example 2 and FIGS. 27A-27C) has the advantage that it allows for precise replication of the topographical features of tissue samples, such as human-derived decellularised dermis, e.g. acellular dermis (ADM). Moreover, casting method allows replication of the full range of features of the tissue surface topography and thus is not limited by the inherent resolution of imaging and/or lithography methods (see FIGS. 27A-27C for a comparison of natural ADM BM tissue surface and ADM BM C as cast according to the method above showing a close reproduction of the natural features in the cast implant surface).

Method of Applying Texture to the Surfaces of the Invention

In embodiments, the method comprises the step of preparing said textured implant material surface by etching, stamping or moulding. In embodiments, the method comprises the step of preparing said textured implant material surface by etching. In embodiments the method comprises the step of preparing said textured implant material surface by stamping, optionally multiple stamping of a single surface to produce a textured surface having a number of stamped irregular textured regions, e.g. wherein the stamped images cover at least half, suitably more than half, and in embodiments substantially all of the implant surface configured to contact a patient's tissue when inserted. In embodiments the method comprises the step of preparing said textured implant material surface by moulding.

In embodiments the implant material prepared by said method is an implant material as described in any one of the aspects and embodiments of the invention described herein.

Data Set

In an aspect of the invention is the use of spatial data representing the X, Y and Z dimensions acquired from a tissue surface in a method of preparing a textured material or a photoresist for use in preparing a textured material. In embodiments, the textured material is a textured implant material as described herein or a template as described herein.

In an aspect of the invention is a method of processing and/or modifying spatial data in the X, Y and Z dimensions, suitably so as to provide a data set capable of being used by a printer, for example a laser writer or 3D printer.

In embodiments, the use includes wherein the spatial data acquired from the tissue surface is processed before use in said method of preparation.

In an aspect of the invention is spatial data in the X, Y and Z dimensions acquired from a tissue surface.

In an aspect of the invention is a data carrier, suitably a computer readable data carrier, comprising spatial data as defined herein.

Tissue

In the above methods of uses, the tissue (i.e. the tissue from which spatial data is the X, Y and Z dimensions has been obtained or is representative of) may be any suitable body tissue, preferably internal body tissues. In embodiments, the tissue is dermal tissue, optionally wherein said dermal tissue is selected from the basement membrane of the skin, the papillary dermis layer of the skin; or the basement membrane superimposed on the papillary dermis of the skin, preferably wherein the respective dermal tissue is the BM surface layer of acellular dermal matrix.

In embodiments the tissue is acellular dermal matrix, optionally wherein the acellular dermal matrix is selected from the basement membrane of acellular dermis, the papillary dermis layer of acellular dermis or the basement membrane overlying papillary dermis layer in the acellular dermis.

The basement membrane (BM) is a thin layer (20-100 nm thick) of collagens (IV and VII), glycoproteins (entactin and perlecan) and proteoglycans (heparan sulfate and glycosaminoglycans) that separate epidermis and dermis within skin and epithelial and underlying layers within other tissues/organs throughout the body. Its function is organ specific and therefore its composition and morphology throughout the body reflects this. The BM in skin is a fusion of the basal lamina (BL) and lamina reticularis (LR) through anchoring fibrils such as collagen VII. The basal lamina can be separated further into 2 distinct layers: lamina lucida (LL) and lamina densa (LD). Within skin, the LD and LR (deepest layers of BM) provide spatial and mechanical cues for fibroblasts to attach to and perform their individual functions. It directs cell differentiation and cell process through a synergising effect of attached growth factors, topographical and mechanical (stiffness) cues.

The BM overlying PD within skin contains an abundance of specifically periodic and specially orientated motifs for cell attachment, and/or proliferation/differentiation. The topographical features of the BM are nanometre size whilst the underlying PD is on a micron scale; working synergistically. These topographical cues are specific to the cells interacting with them and appear to encourage normal cellular processes. Therefore, a fibroblast in vivo attached to the BM will not be in an unfamiliar or stressed state. Accordingly, in normal circumstances in the body, cells are not inflammatory or hyperproliferative and a foreign body reaction does not ensue. Further, collagen type IV is necessary for normal mammary epithelial cell attachment in vivo and while not essential for normal mammary fibroblast attachment it may still promote effective cell attachment. As mentioned previously, collagen type IV is a component of the basement membrane and therefore replication of BM topography into silicone may promote mammary epithelial and fibroblast cell attachment and proliferation in vivo.

Through mimicking the topographical cues of BM/PD onto the surface of a silicone implant, cells that encounter it attach and stabilize without becoming stressed and transforming into a pro-inflammatory/fibrotic phenotype resulting in the initiation of chronic inflammation and fibrosis around the implant through attraction and activation of neutrophils and macrophages (see cellular response data and discussion). Consequently, it is thought that the extent of the foreign body reaction and subsequent capsular contracture formation would be potentially averted.

Whilst it is understood that natural BM/PD may be able to effect such functions in the body, it is entirely surprising that the excellent results achieved using the fabricated and cast materials prepared would show the excellent results observed when the 3D topographic features were reproduced in silicone implant surfaces as discussed in the examples section. The investigation by the present inventors has therefore led to a ground-breaking innovation that has the potential to have significant impact on 3D surface design for implants, particularly in the breast implant field with the effect of reducing problems associated with this growing demand for this surgical procedure on medical and/or cosmetic grounds.

As discussed, present methods for forming irregular implant surfaces typically rely on crude and inherently unpredictable processes. Such methods thus provide non-reproducible surfaces that may differ significantly from batch to batch, leading to potentially unreliable results. It is however desirable to be able to control the surface features with a high degree of accuracy, particularly in the case of prosthetic implants such as breast implants, where differences in micro and nano features have been proven to play an important role in cellular interaction, biocompatibility and capsular contraction. The present invention thus addresses the need for methods which provide control of irregular surface features with a higher degree of accuracy and reproducibility and/or which provide a higher degree of flexibility for producing different designs.

Further Aspects

In a further aspect is provided an implant material comprising a textured surface as prepared by a method as defined according to any aspect or embodiment herein.

Also provided is a template for use in preparing an implant material of the invention as described herein, said template having textured surface parameters as defined according to any previous claim, or a negative of said textured surface parameters, optionally wherein the template is a mould or stamp, such as defined above.

The invention also provides the use of a template as described according to any embodiment above in a method of making a textured implant material. Typically the template is a silicone template, most preferably PDMS.

A cosmetic method comprising the step of inserting an implant material as described in any of the aspects and embodiments of the invention disclosed herein subcutaneously in a patient. Suitably said method is so as to provide minimal or no capsular contraction and/or cellular immunogenic response. Furthermore, in embodiments the method is for reconstructions of the breast.

General

The term "comprising" encompasses "including" as well as "consisting" e.g. an implant "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

The use of the term "irregular" in the context of the surfaces of the present invention will be well understood by the skilled person. Suitably, the term "irregular" in the context of the surfaces of the present invention refers to surface areas which are devoid of regular geometric patterns (such as repeating patterns), such as at the relevant macro, micro and/or nano scales (such as at the 1 cm×1 cm, 1 mm×1 mm, 100 micron×100 micron and/or at sub-micron level). The term "irregular" in the context of the surfaces of the present invention thus includes surfaces which appear to be disordered.

It will be appreciated on reading the present application that the surface of implants prepared according to the present invention may be formed by use of a stamp having an irregular textured surface which imparts its irregular surface topography to the implant on stamping. The stamp may thus be used repeatedly over the surface of the implant to ultimately provide up to complete surface coverage consisting of the substantially repeated irregular surface imprinted by the stamp. It is thus intended that the term "irregular" within the meaning of the present invention includes surfaces which have more than one, such as a plurality of repeating areas of such irregular surface topography.

The terms "ACD" and "ADM" are used interchangeably and refer to acellular (decellularised) dermal matrix.

DESCRIPTION OF FIGURES

FIG. 16A shows the 2D planar surface depiction image of the AFM data, FIG. 16B shows the corresponding 3D image, FIG. 16C shows the AFM line profile data (in the vertical and horizontal direction) corresponding to the diagonal line shown in FIG. 16D (FIG. 16D also showing the respective ISO 25178 areal data for the surface of FIG. 16A).

FIG. 17A shows the 2D planar surface depiction image of the AFM data, FIG. 17B shows the corresponding 3D image, FIG. 17C shows the AFM line profile data (in the vertical and horizontal direction) corresponding to the diagonal line shown in FIG. 17D (FIG. 17D also showing the respective ISO 25178 areal data for the surface of FIG. 17A).

FIG. 18A shows the 2D planar surface depiction image of the AFM data, FIG. 18B shows the corresponding 3D image, FIG. 18C shows the AFM line profile data (in the vertical and horizontal direction) corresponding to the diagonal line shown in FIG. 18D (FIG. 18D also showing the respective ISO 25178 areal data for the surface of FIG. 18A).

FIG. 19A shows the 2D planar surface depiction image of the AFM data, FIG. 19B shows the corresponding 3D image, FIG. 19C shows the AFM line profile data (in the vertical and horizontal direction) corresponding to the diagonal line shown in FIG. 19D (FIG. 19D also showing the respective ISO 25178 areal data for the surface of FIG. 19A).

FIG. 20A shows the 2D planar surface depiction image of the AFM data, FIG. 20B shows the corresponding 3D image, FIG. 20C shows the AFM line profile data (in the vertical and horizontal direction) corresponding to the diagonal line shown in FIG. 20D (FIG. 20D also showing the respective ISO 25178 areal data for the surface of FIG. 20A).

FIG. 21A shows the 2D planar surface depiction image of the AFM data, FIG. 21B shows the corresponding 3D image, FIG. 21C shows the AFM line profile data (in the vertical and horizontal direction) corresponding to the diagonal line shown in FIG. 21D (FIG. 21D also showing the respective ISO 25178 areal data for the surface of FIG. 21A).

FIG. 23B: 100 μm scale left, 50 μm scale right; and FIG. 23C: 20 μm scale left and 10 um scale right); natural ADM BM surface topography (FIG. 23D: 1 mm scale left, 500 μm scale right; FIG. 23E: 100 μm scale left, 50 um scale right; and FIG. 23F: 20 um scale left and 10 μm scale right); comparative smooth implant (Mentor Smooth) surface topography (FIG. 23G: 100 μm scale; FIG. 23H: 50 μm scale; and FIG. 23I: 1 μm scale); and comparative textured implant (Mentor Siltex) surface topography (FIG. 23J: 1 mm scale; FIG. 23K: 500 μm scale; and FIG. 23L: 1 μm scale bottom).

FIGS. 24A-24B depict ISO 25178 areal surface roughness measurements calculated as described herein describing (FIG. 24A) the 3D surface texture of ADM BM surface according to the invention compared to commercially available smooth (Mentor smooth) and (FIG. 24B) textured (Mentor Siltex) implants.

FIG. 25 Comparison of roughness values of Native ADM BM in comparison to ADM BM PDMS F and ADM BM PDMS C at different length scales.

FIG. 26A shows the 2D image of each surface (natural ADM BM at left, and ADM BM PDMS F at right), FIG. 26B shows the 3D image, and FIG. 26C shows the 2D profile data (vertical vs lateral dimension).

FIG. 27A shows the 2D image of each surface (natural ADM BM at left, and ADM BM PDMS C at right), FIG. 27B shows the 3D image, and FIG. 27C shows the 2D profile data (vertical vs lateral dimension).

FIG. 43 shows autocorrelation length data for native ADM BM, ADM BM PDMS F and ADM BM PDMS C at different length scales.

Figure 1:
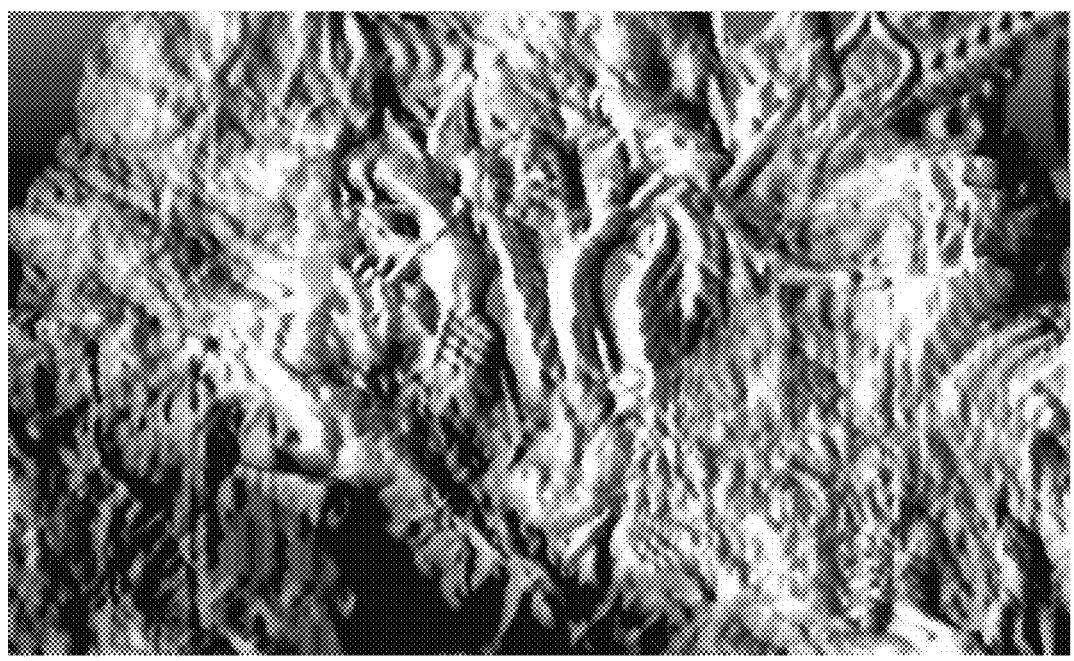
FIG. 1 depicts a grayscale montage of AFM images of ADM BM as produced by the fabrication method of the invention described in example 1.

The invention is described in more detail by way of example only with reference to the following Examples and experimental procedures.

General Methods

Isolation of Acellular Dermis (ACD) from Cadaver Skin

ADM is soft and buff white in colour. Donors have been screened for potential infective organisms and tissue has been deemed to be suitable for transplantation based on the results of stringent donor testing. The ADM sample was completely aseptically decellularised and freeze dried while preserving biological components and morphology of dermal matrix.

Storage and Preparation of ADM for Imaging

Method A: Samples were stored at −20° C. and thawed on ice when required. A 5 cm×5 cm of human acellular dermal matrix was removed from the packaging and placed in a petri dish. A section of ADM, approximately 2×2 cm, was excised from the sample and spread out in another petri dish. This sample was fixed in 2% glutaraldehyde, in 0.1 M pH 7.4 phosphate buffer solution at 8° C. for 12 hours. The tissue was then washed with phosphate buffer solution (PBS)×3 to remove any residual glutaraldehyde. The tissue was then dehydrated using increasing concentrations of intermediary fluid (ethanol) and was kept in 100% ethanol until it was ready for critical point drying (CPD). After CPD the sample was ready for imaging.

Method B: The ADM was removed from storage in −20° C. freezer and allowed to thaw. Samples were cut into 2 cm×2 cm sections and washed in sterile PBS×3 to remove any freeze protectants. The samples were then placed BM side up onto microscope slides and allowed to slowly air dry at 4° C. for 24 hours. Samples were not fixed or critical point dried. After drying the sample was ready for imaging.

H&E and Immmunoperoxidase Staining of BM Proteins—Collagen IV, Collagen VII and Laminin 5.

H&E staining to look at morphological features of ADM BM and immunoperoxidase staining to confirm presence of the BM was carried out using standard laboratory protocols. Immunoperoxidase staining was performed for collagen IV, collagen VII and laminin 5. It was important to stain for BM proteins so that it was certain that all imaging and analysis was actually conducted on the BM. It is clear in practice to see increased staining along the top of ADM where there is thin strip of tissue. This is the basement membrane and it has stained positively for three of the main basement membrane proteins; collagen 4, collagen 7 and laminin 5. These images confirm the presence of the basement membrane, superior to ADM and confirm that all the measurements and analysis conducted are of the ADM BM.

METHODS OF PREPARING IMPLANT
SURFACES OF THE INVENTION

Example 1—Production of ADM BM PDMS
F—Fabricated Implant Surface by Grayscale
Lithography of Acellular (Decellularised) Dermal
Matrix Pattern and Reproduction in Silicon by
Modified Deep Reactive Ion Etching (DRIE) to
Create a Template Before Creating Stamps of ADM
BM Pattern in PDMS Imaging the ADM BM Surface The basement membrane (BM) side of the ADM BM surface is distinguished from dermal side through visually checking the tissue for roughness and a buff-colour. Further, BM characteristically repels water and the contact angle of the water is higher than on BM side than PD side. The samples were then placed BM side up onto microscope slides and allowed to slowly air dry at 4° C. for 24 hours. Over one hundred 90 µm×90 µm$^2$ AFM scans were conducted in different areas of the ADM sample, on a number of different samples.

Preparing an Electronic File from Height Information of Grayscale AFM Images

The raw images from the AFM database were loaded into the following scanning probe analysis software, NanoScope Analysis. A plane fit (0-2 orders) was applied to all images. The images were then exported as bitmaps (BMP's). The BMP's were loaded into the following open source scanning probe analysis software Gwyddion (http:/gwyddion.net/) to convert to 8 bit grayscale BMP's. Each AFM image was re-scaled as 180 pixels. The ADM montage was created using an open source imaging software to stitch together various AFM images of ADM, which were chosen based upon their superior image quality. AFM images of ADM BM were stitched together based upon similarities in height at the edges of the images so that images could be blended without leaving stitch lines The ADM montage was converted to an 8 bit grayscale image, which consists of 256 grayscale levels, which could be read by a laserwriter (Microtech Laserwrited LW405, but other laserwriters can be used). FIG. 1 shows an exemplary 3D rendered grayscale image montage of the ACD.

Exposing ADM Pattern into Photoresist

Maskless grayscale photolithography was performed using a laserwriter. The 8-bit grayscale image prepared as above, was loaded into the laserwriter software and the exposure dose for each pixel assigned. Vertical features of the ADM were scaled down for incorporation into the S1813 photoresist as it is thin (1.3 microns) whereas vertical features of the ADM topography were larger than 2 microns. A 2 cm×2 cm plain silicon wafer was sonicated for 5 minutes in acetone, distilled water and isopropyl alcohol (IPA). The sample was then dried with nitrogen gas and dehydrated on a hot plate set at 130° C. for 10 minutes. Immediately after removing from the hotplate the sample is placed into the spinner and hexamethlydisilazane (HMDS) is applied to the surface. It is then left to rest for 10 seconds and spun at 4000 rpm for 60 seconds. S1813 photoresist was spin coated onto silicon wafers at 3000 rpm for 60 seconds, after application of HMDS, followed by soft bake at 72° C. for 2 minutes. The prepared grayscale BMP is loaded into the Laserwriter and the pixel size is set at 0.5 um in X and Y, which is the smallest possible pixel size. (A 180×180 pixel image will therefore be 90×90 um after exposure). Using a gain of 5.5 and bias of 1, exposure to UV leads to degradation of the resist as performed by the Laserwriter. The exposure is developed in MF319 for 40 seconds with gentle agitation before 40 seconds in IPA. A final rinsing in distilled water was performed and the wafer was dried with nitrogen gas.

Modified Deep Reactive Ion Etching (DRIE)

Deep reactive ion etching using a modified Bosch process with scale up of the vertical features allowed permanent fixture/transfer of the ADM surface topography in the silicon template.

| Grayscale etching recipe: Etch selectivity: 10:1. | | | | | | |
|---|---|---|---|---|---|---|
| Step | Step time | Pressure (mTorr) | RF power | ICP power | SF$_6$ (Sscm) | C$_4$f$_8$ (Sscm) | O$_2$ (Sscm) |
| Etch | 3 | 10 | 5 | 300 | 100 | 5 | 0 |
| O$_2$ Etch | 3 | 10 | 5 | 300 | 0 | 0 | 30 |
| Deposition | 4 | 10 | 5 | 300 | 5 | 100 | 0 |
| Repeats | | | | | 80-100 | | |

Manufacture of PDMS Medical Grade Casts

The PDMS used was MED-6215 (Nusil, Calif., U.S) optically clear PDMS elastomer. The PDMS came in two parts; a viscid PDMS elastomer (Part A) and a runny platinum curing agent, "Part B", which were mixed together at a ratio of 10:1 by weight. The PDMS was de-gassed in a desiccator for 1 hour to remove any bubbles. The silicon wafer was vapor treated with a silanizing agent (TMCS) for 10 mins in a desiccator under vacuum, in order to ease the release of PDMS from the silicon wafer. PDMS was spun at 130 rpm on to silicon wafer containing the 1.5 cm×1.5 cm exposure of ADM montages. Spinning at 130 RPM produced PDMS with a thickness of approximately 450-600 um, which is similar to the thickness of commercially available silicone breast implant shells and could also be peeled away easily from the silicon wafer without fragmenting. PDMS was spun onto wafers using a programmable resist spinner. A curing step was required to crosslink and harden the PDMS and therefore the PDMS was baked in an oven at 80° C. overnight. The 1.5×1.5 PDMS stamp was then cut out using a scalpel, which creates the finished PDMS stamp containing the surface features of ADM reproduced in it.

AFM imaging was used to acquire the respective images for reproduction via the fabrication method. However, higher or lower resolution image data may be obtained using alternative imaging technologies. Any suitable contact or non-contact profilometers can be used, suitably to produce grayscale images where each pixel correlates to a given height. Thus, surfaces having a variety of macro, micro and nano surface features according the invention may be produced. In addition, since the fabrication method allows for production of digital information of the surface, the surface information can thus be processed (such as to filter out certain features) to produce a variety of surface topographies, including those according to the invention.

Example 2—Creation of ADM BM C—Casting of Acellular Dermal Matrix in PDMS

Preparation of Acellular Dermal Matrix (ADM)

ADM washed in sterile deionised water×3 and attached BM side up onto microscope slide and allowed to slowly air dry for 24 hours at 4° C. Basement membrane (BM) side of ADM is distinguished from dermal side through visually checking the tissue for roughness and a buff-colour. Further, BM characteristically repels water and the contact angle of the water is higher than on BM side than RD side.

Silanization

To allow easy peeling of PDMS from ADM BM, the ADM was silanized. Silanization performed by placing ADM in vacuum desiccator on a steel-meshed platform with 100 ul of the fluorosilane TMCS in a 3 cm diameter petri dish beneath the ADM. The vacuum was pumped for 30 seconds-1 min until the TMCS is visibly beginning to bubble and evaporate. At this stage the desiccator is held under vacuum for 10 minutes to allow the TMCS to silanize the ADM surface. The ADM is then ready for casting.

Creation of Inverted Cast

PDMS is spun onto the ADM at 4000 RPM for 1 minute then left at room temperature (17° C.) for 48 hours. This step was repeated twice. The PDMS was carefully peeled off ADM and place on a cured square of PDMS on a clean microscope slide, pattern facing upwards. The PDMS was then cured overnight at 120° C.

Creating Final Cast of ADM

PDMS is again silanized with TMCS using method outlined above. PDMS (Mentor Corporation) is spun onto the inverted ADM PDMS pattern at 4000 RPM for 1 minute then baked at 25° C. for 48 hours. This step was repeated twice. PDMS was then spun onto the surface at 2000 RPM for 1 minute followed by baking at 60° C. for 1 hour. This was repeated twice. PDMS was again spun at 1000 RPM for 1 minute then baked at 60° C. for 30 minutes, followed by spinning of more PDMS at 500 RPM for 1 minute then curing overnight at 120° C. This resulted in an implant thickness of 450-600 um thick (Same range as commercially available implants. The resulting ADM BM PDMS cast was then characterised as described below and subject to biological cellular assays as described below.

Comparison of Fabrication Method to Casting Method

Figure 26A:
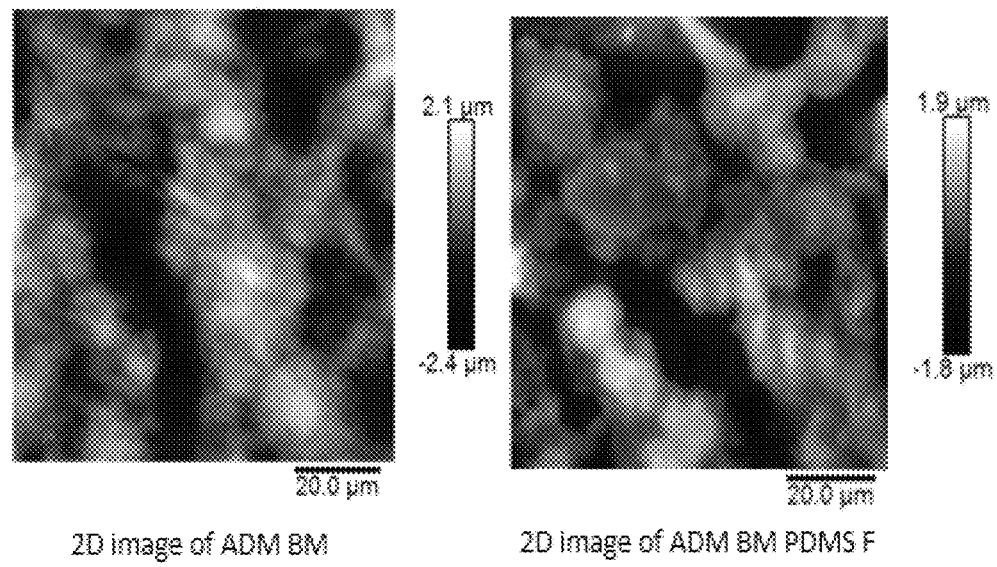
FIGS. 26A-26C depict Atomic Force Microscope (AFM) data for an image scan size of 90×90 μm for natural ADM BM surface topography and ADM BM F surface topography manufactured according to the maskless grayscale lithography method of the invention as described herein.
Figure 26B:
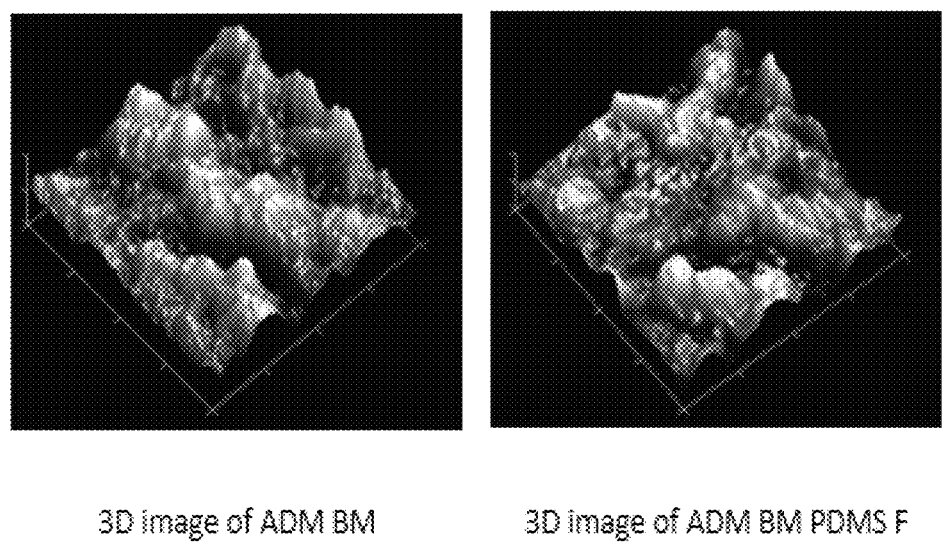
Figure 26C:
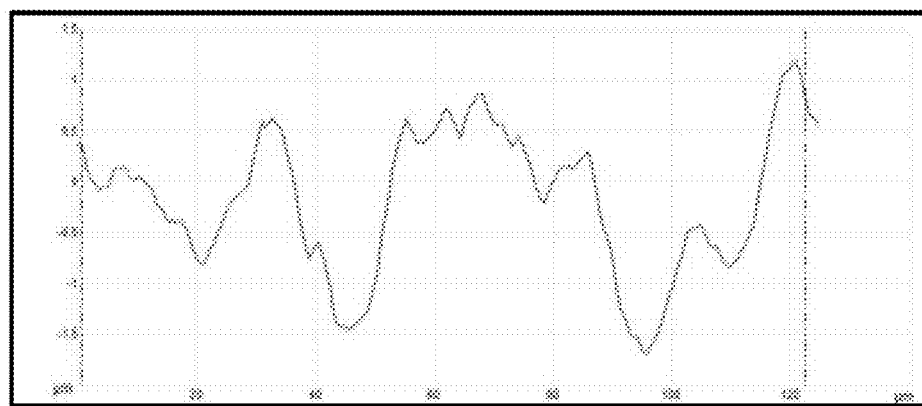
Figure 26C:
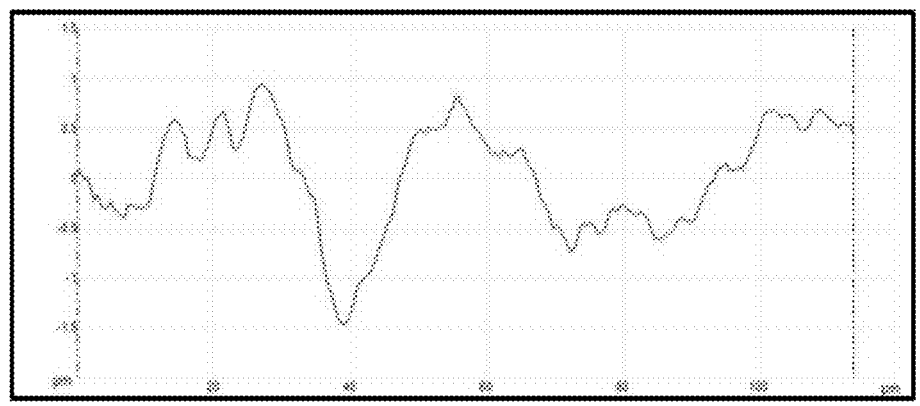
Figure 27A:
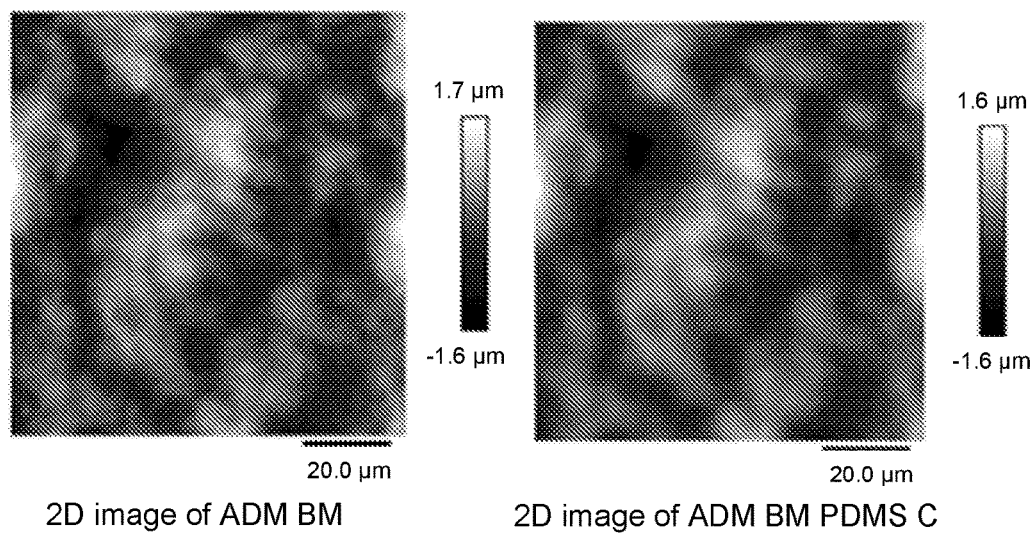
FIGS. 27A-27C depict Atomic Force Microscope (AFM) data for an image scan size of 90×90 μm for natural ADM BM surface topography and ADM BM C surface topography manufactured according to the casting method of the invention as described herein.
Figure 27B:
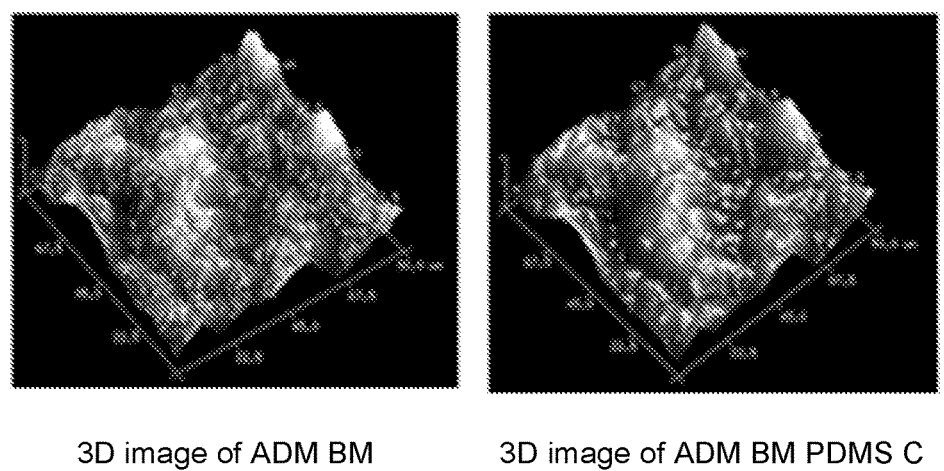
Figure 27C:
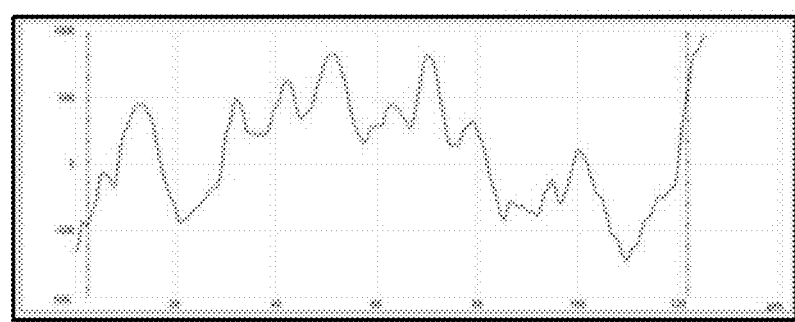
Figure 27C:
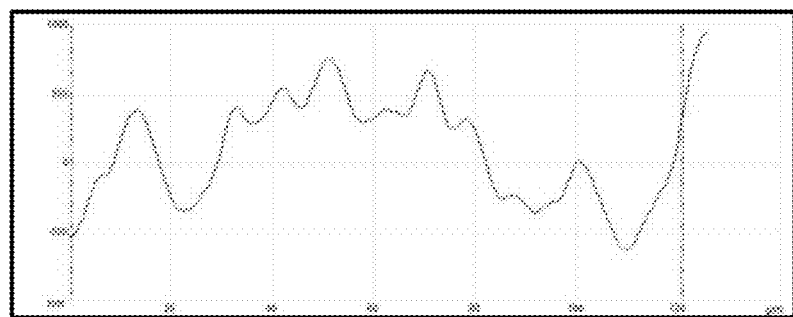
Figure 28A:
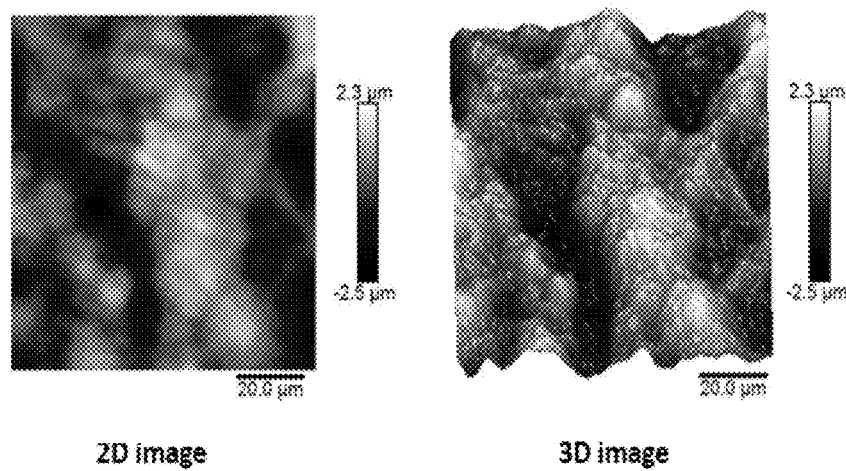
FIGS. 28A-28B show a comparison of native ADM BM (FIG. 28A) to ADM BM PDMS F (FIG. 28B) at 90×90 μm.
Figure 28A:
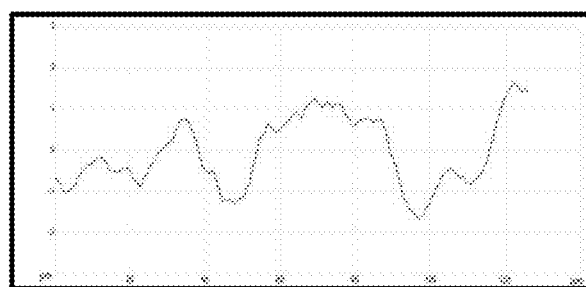
Figure 28B:
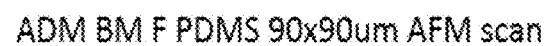
Figure 28B:
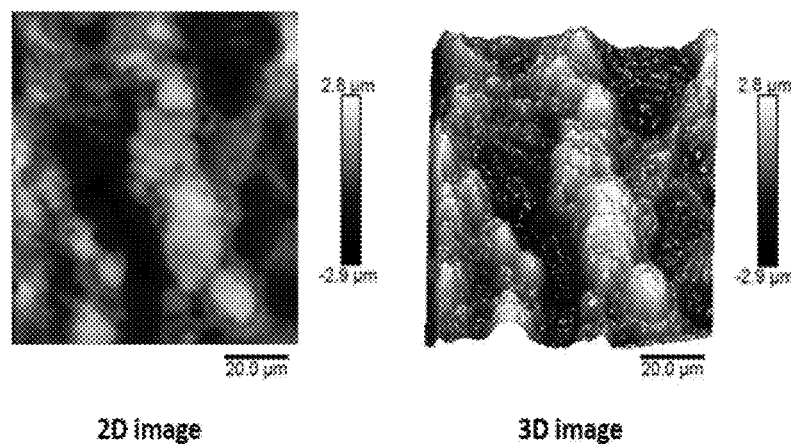
Figure 28B:
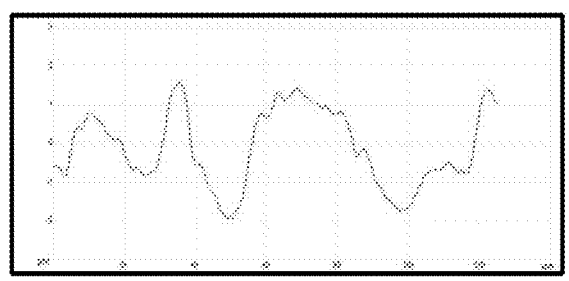
Figure 29A:
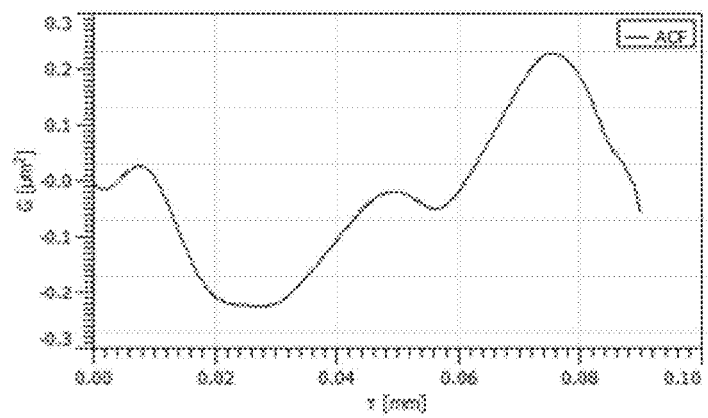
FIGS. 29A-29B show a comparison of native ADM BM (FIG. 29A) to ADM BM PDMS F (FIG. 29B) at 90×90 µm—Autocorrelation lengths.
Figure 29A:
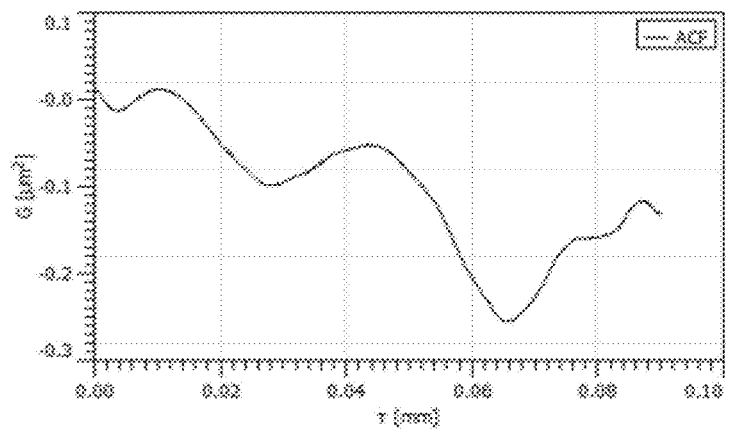
Figure 29B:
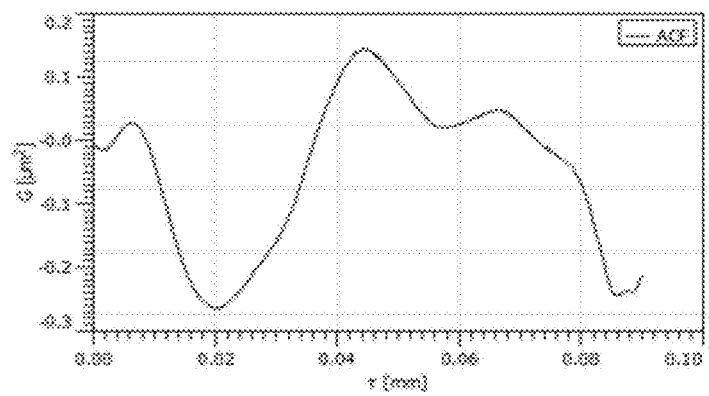
Figure 29B:
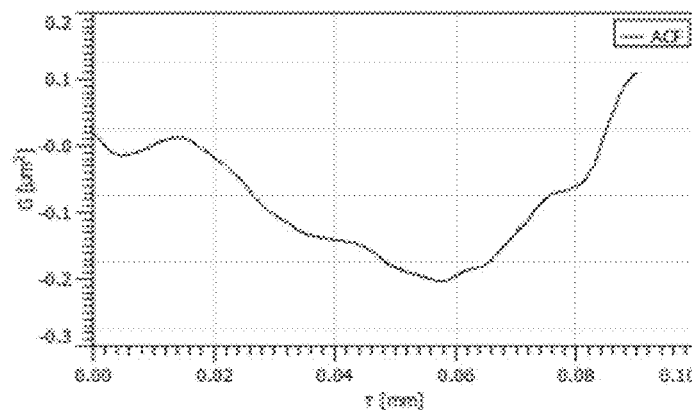
Figure 30A:
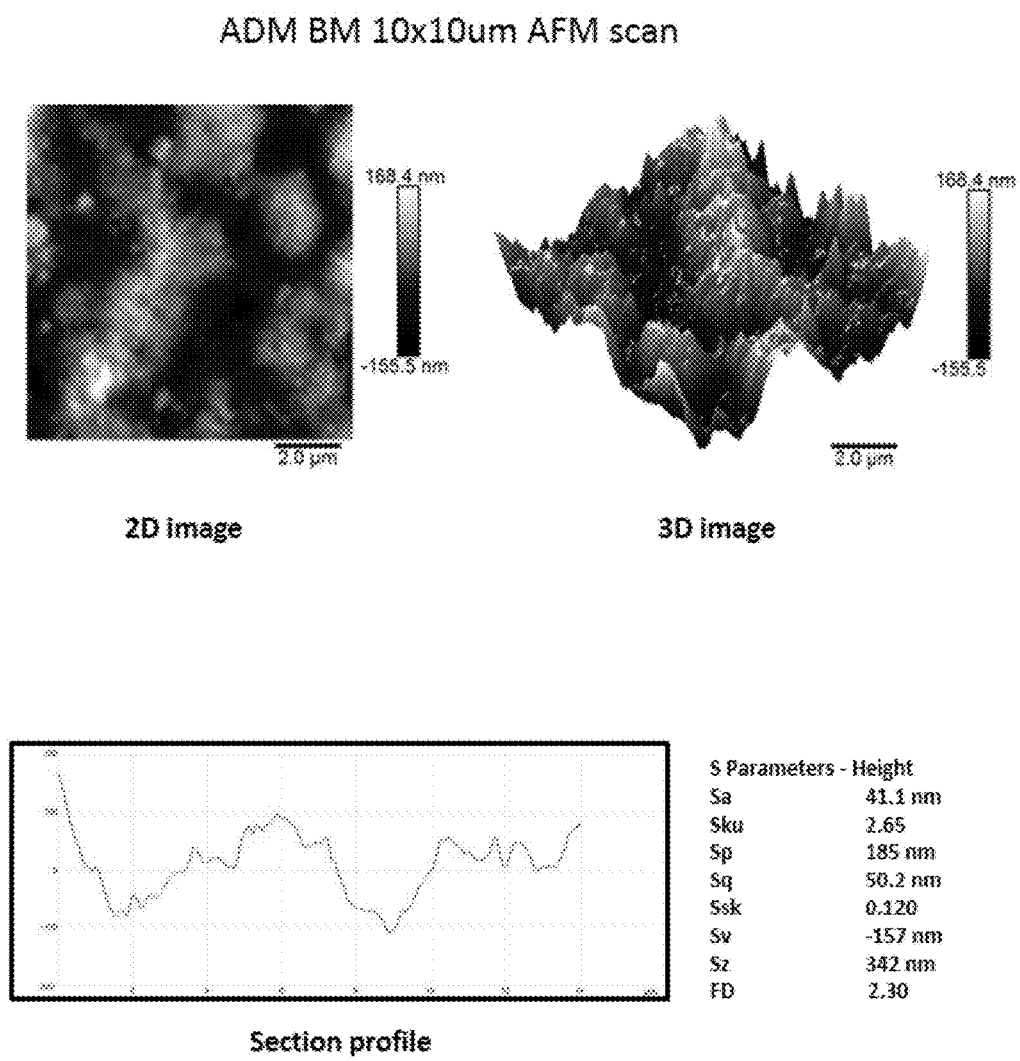
FIGS. 30A-30B show a comparison of native ADM BM (FIG. 30A) to ADM BM PDMS F (FIG. 30B) at 10×10 µm.
Figure 30B:
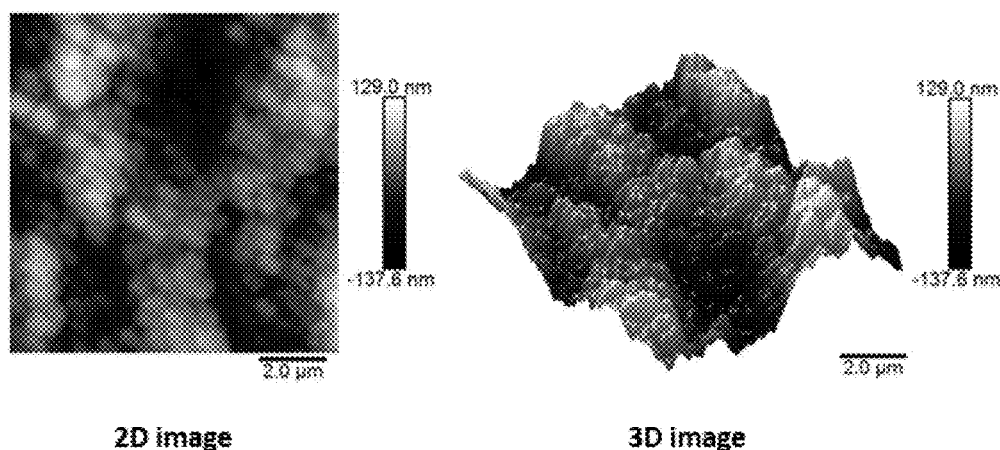
Figure 30B:
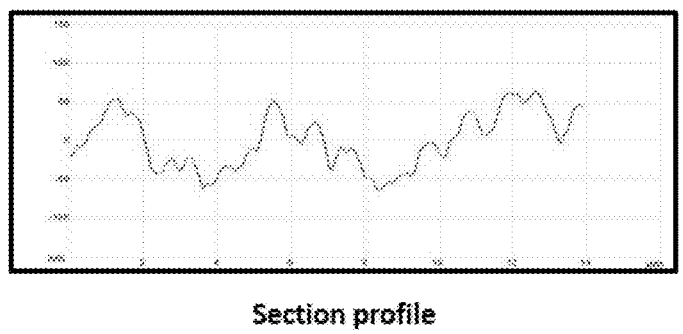
Figure 31:
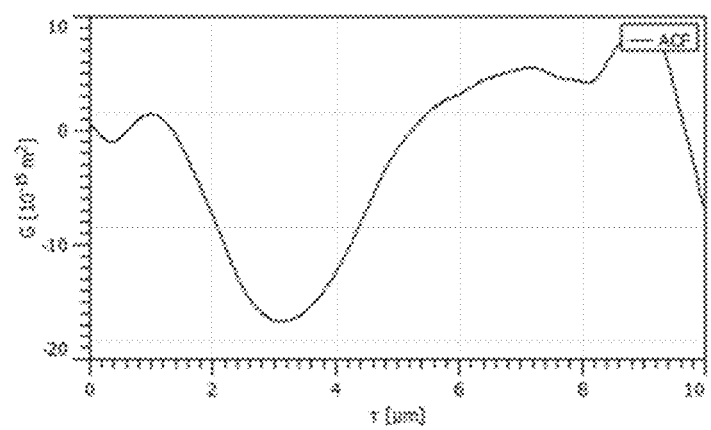
FIG. 31 shows ADM BM PDMS F at 10×10 µm—Autocorrelation lengths.
Figure 31:
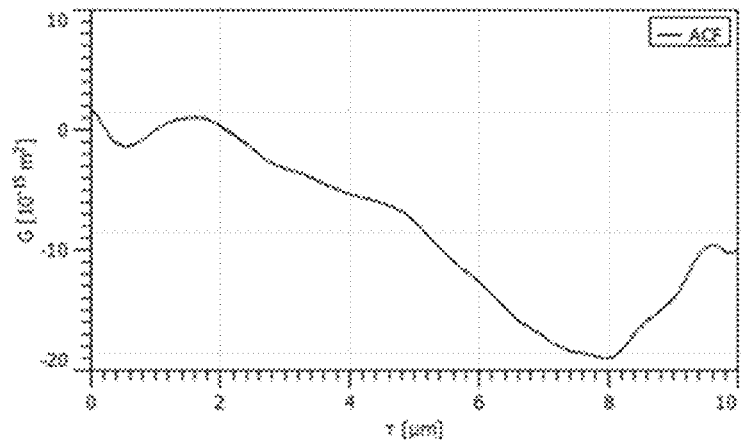
Figure 32A:
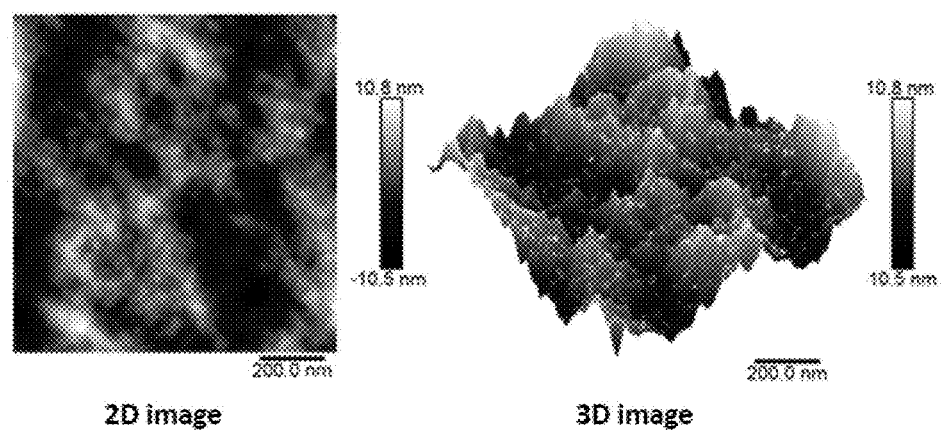
FIGS. 32A-32B show a comparison of native ADM BM (FIG. 32A) to ADM BM PDMS F (FIG. 32B) at 1×1 µm.
Figure 32A:
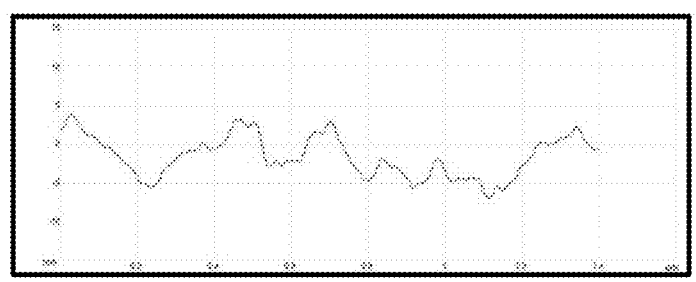
Figure 32B:
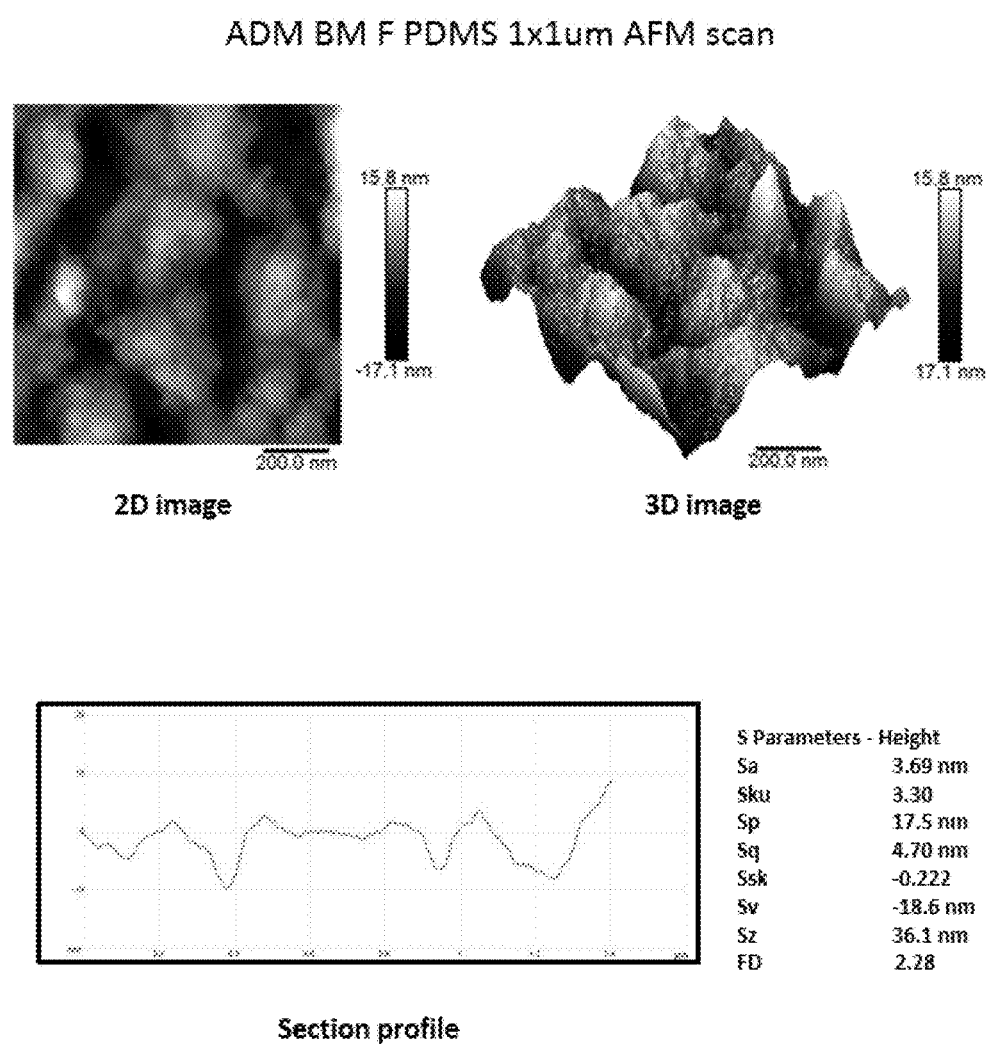
Figure 33A:
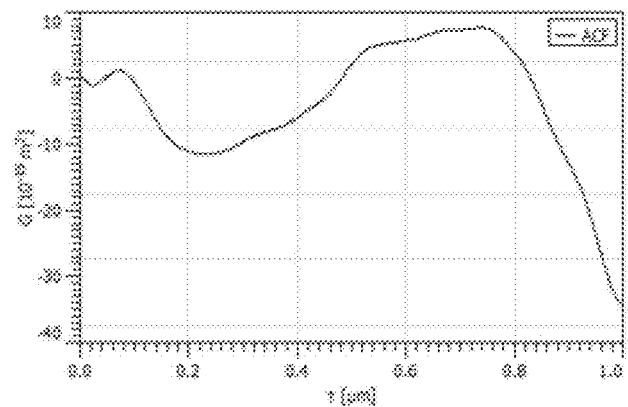
FIGS. 33A-33B show a comparison of native ADM BM (FIG. 33A) to ADM BM PDMS F (FIG. 33B) at 1×1 µm—Autocorrelation lengths.
Figure 33A:
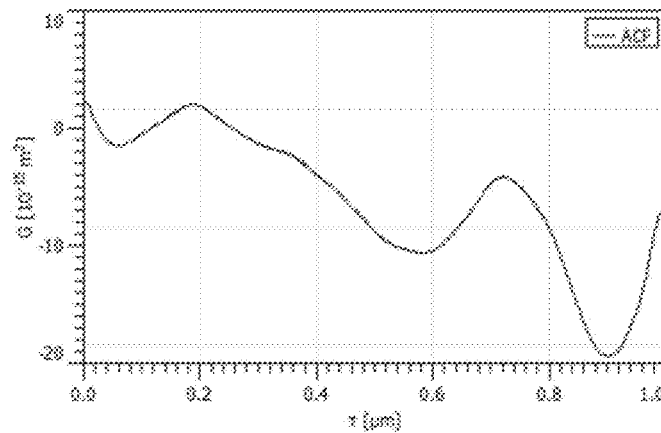
Figure 33B:
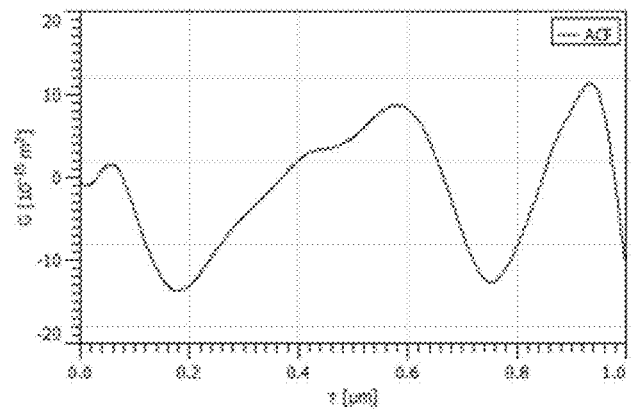
Figure 33B:
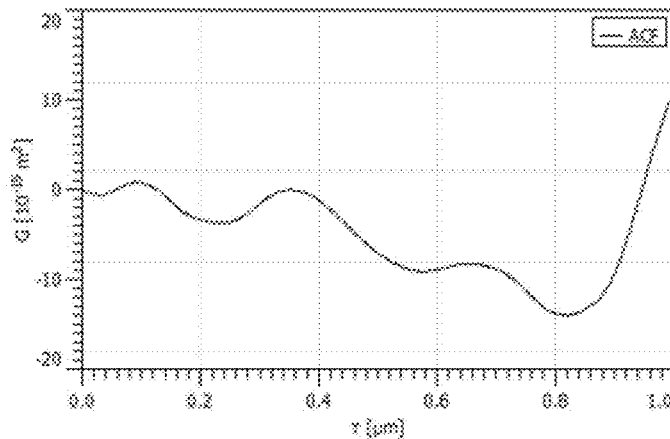
Figure 34A:
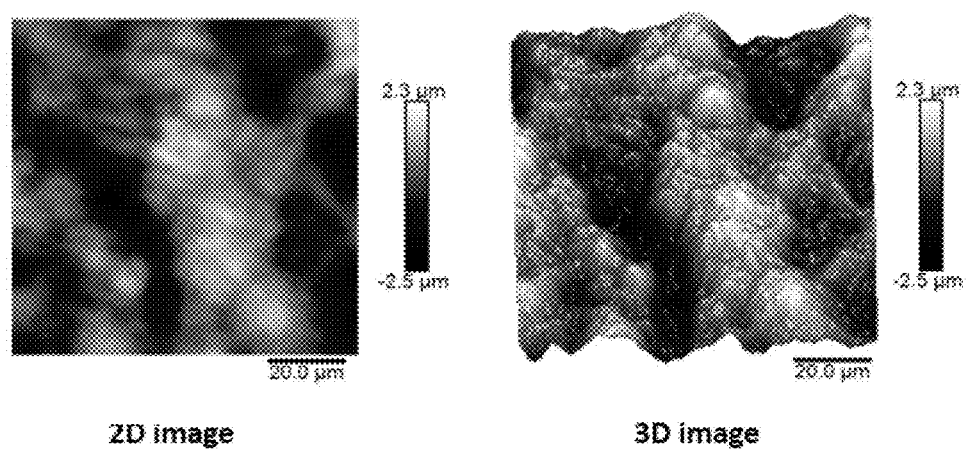
FIGS. 34A-34B show a comparison of native ADM BM (FIG. 34A) to ADM BM PDMS C (FIG. 34B) at 90×90 µm.
Figure 34A:
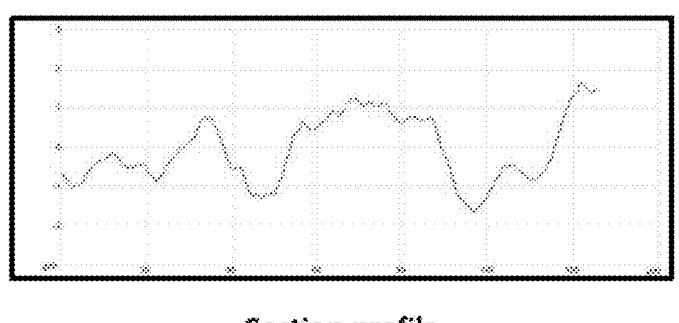
Figure 34B:
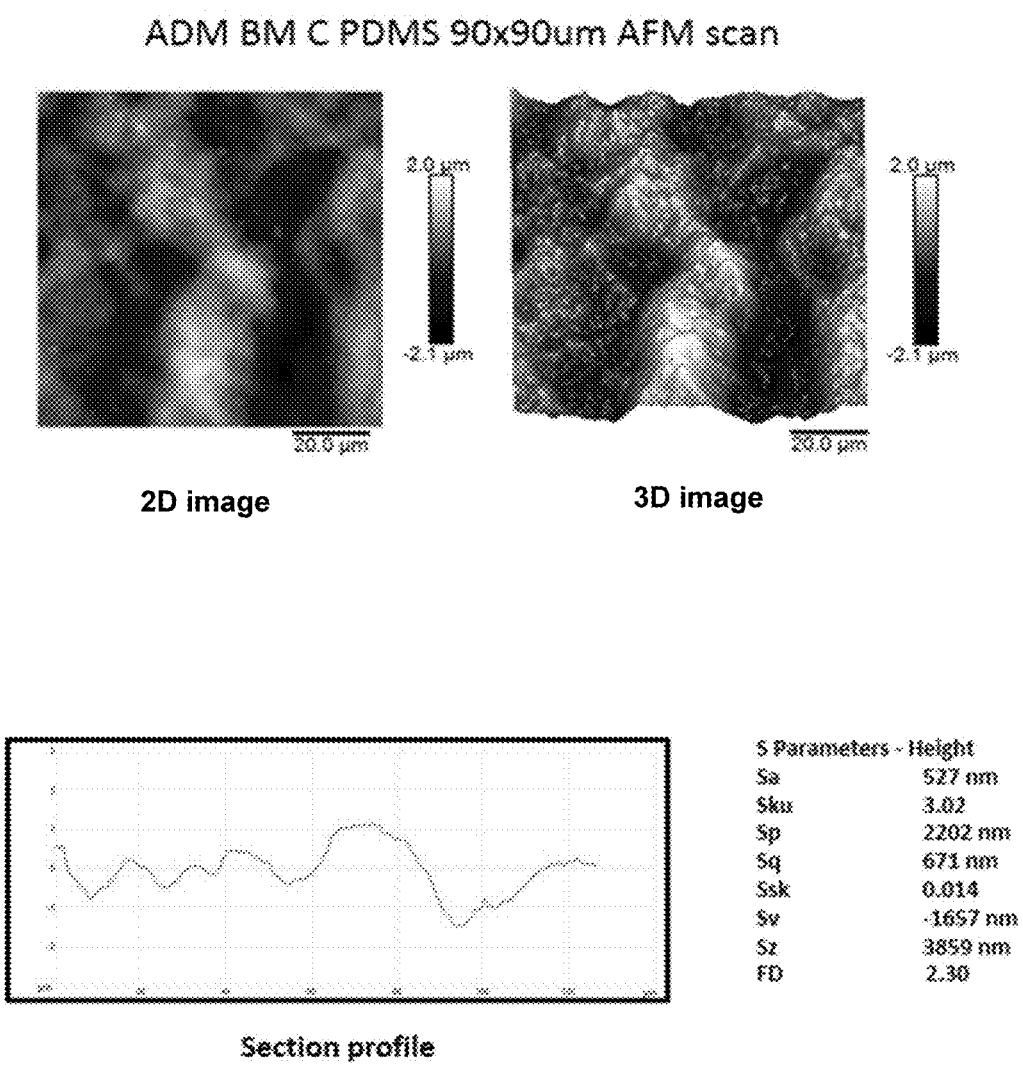
Figure 35A:
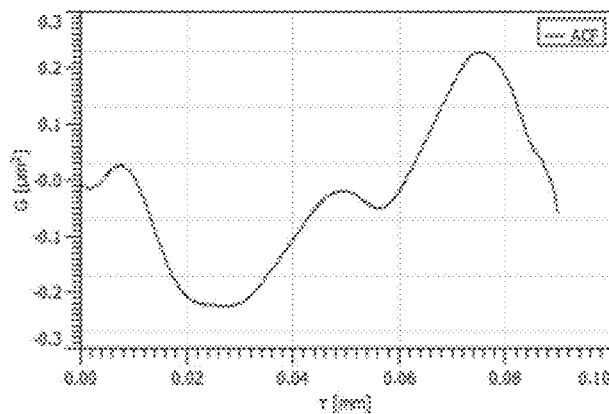
FIGS. 35A-35B show a comparison of native ADM BM (FIG. 35A) to ADM BM PDMS C (FIG. 35B) at 90×90 µm—Autocorrelation lengths.
Figure 35A:
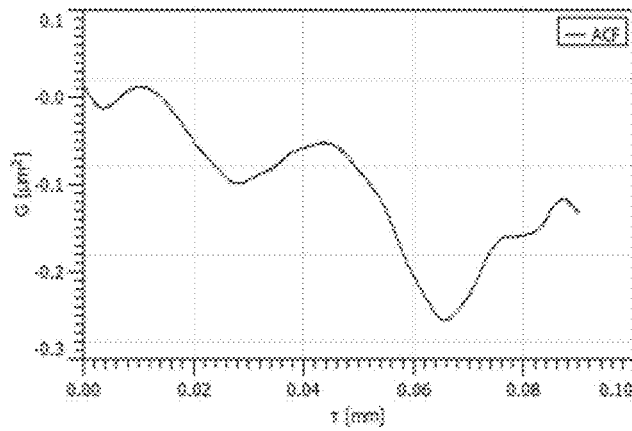
Figure 35B:
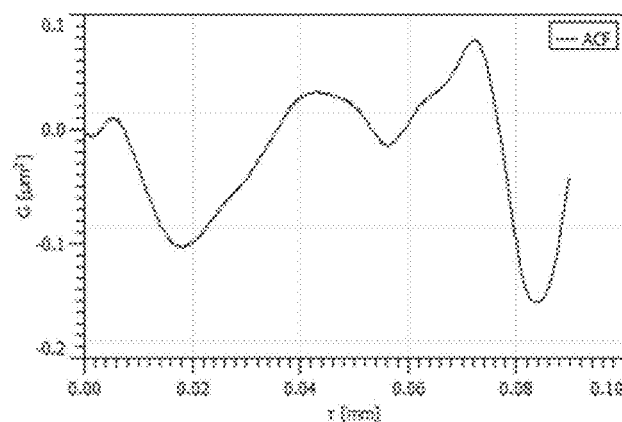
Figure 35B:
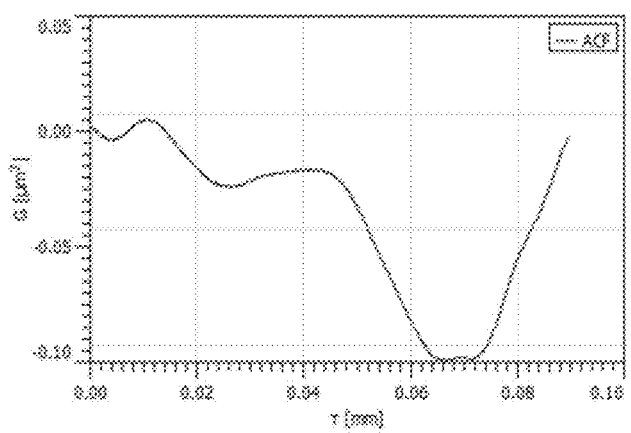
Figure 36A:
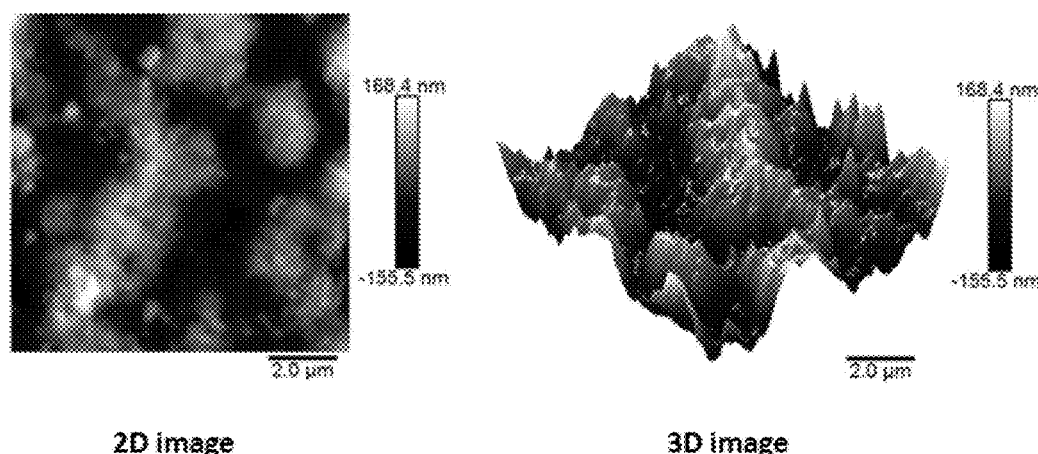
FIGS. 36A-36B show a comparison of native ADM BM (FIG. 36A) to ADM BM PDMS C (FIG. 36B) at 10×10 µm.
Figure 36A:
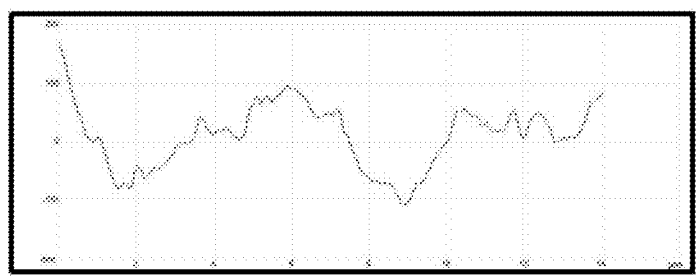
Figure 36B:
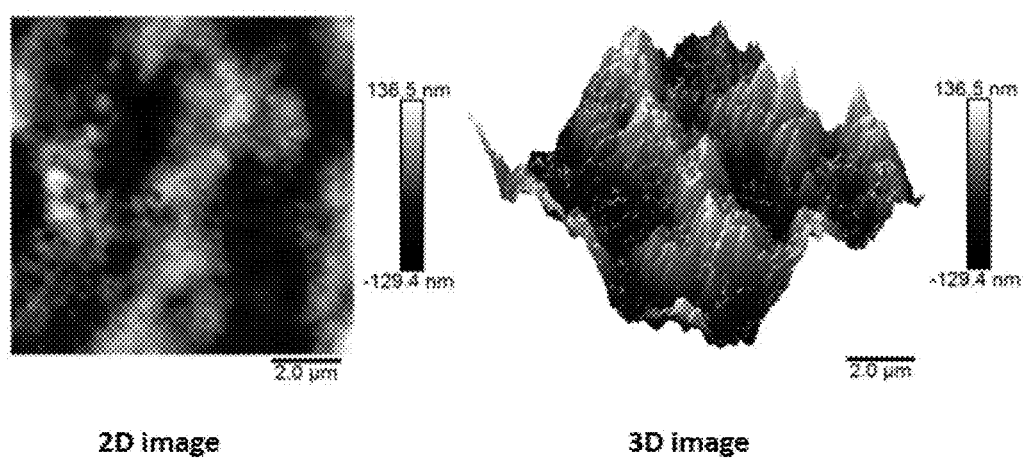
Figure 36B:
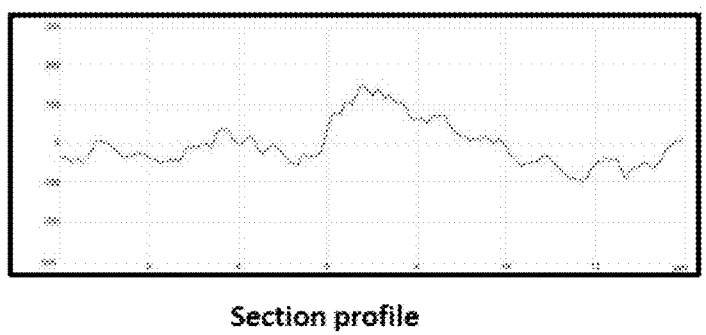
Figure 37A:
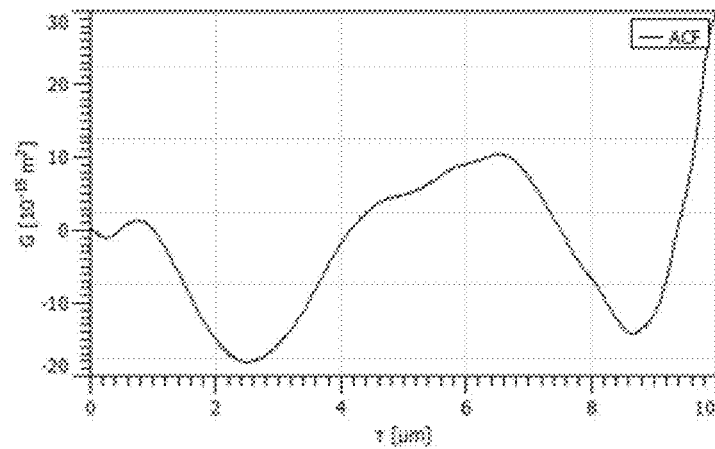
FIGS. 37A-37B show a comparison of native ADM BM (FIG. 37A) to ADM BM PDMS C (FIG. 37B) at 10×10 µm—Autocorrelation lengths.
Figure 37A:
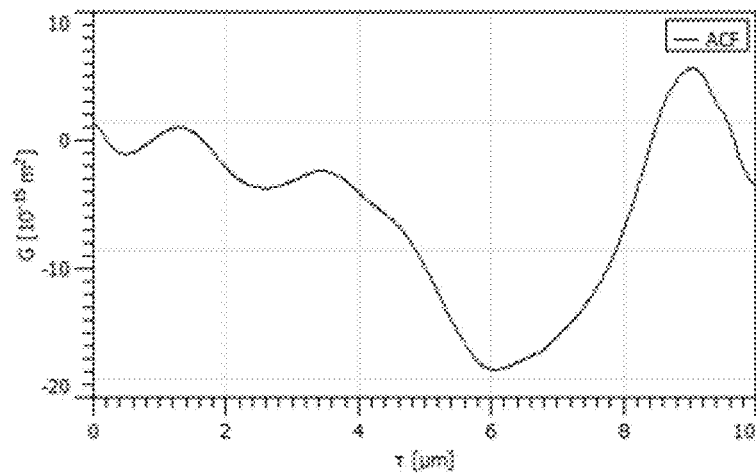
Figure 37B:
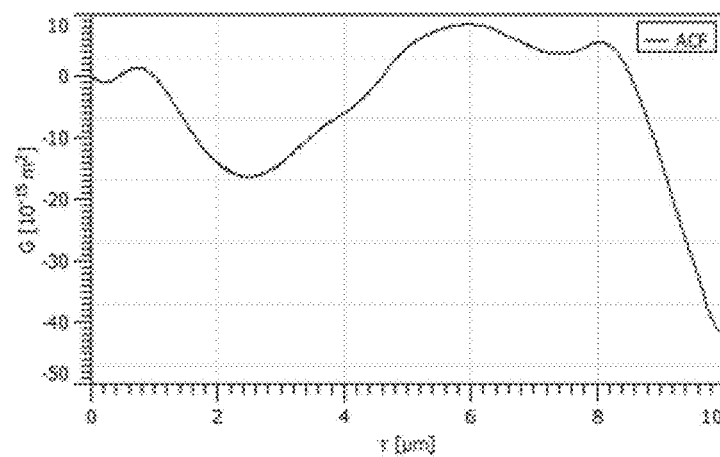
Figure 37B:
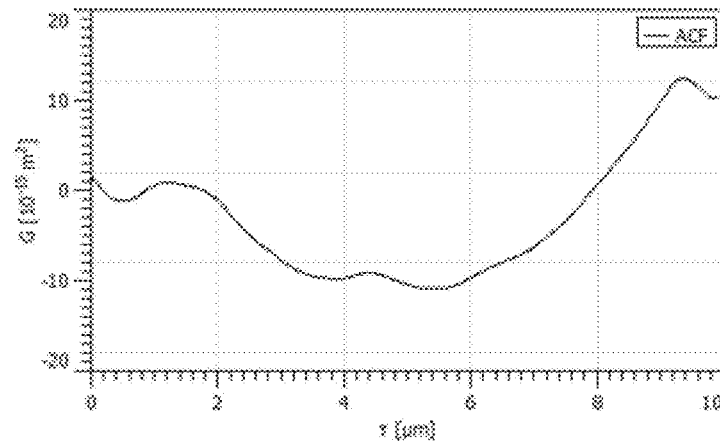
Figure 38A:
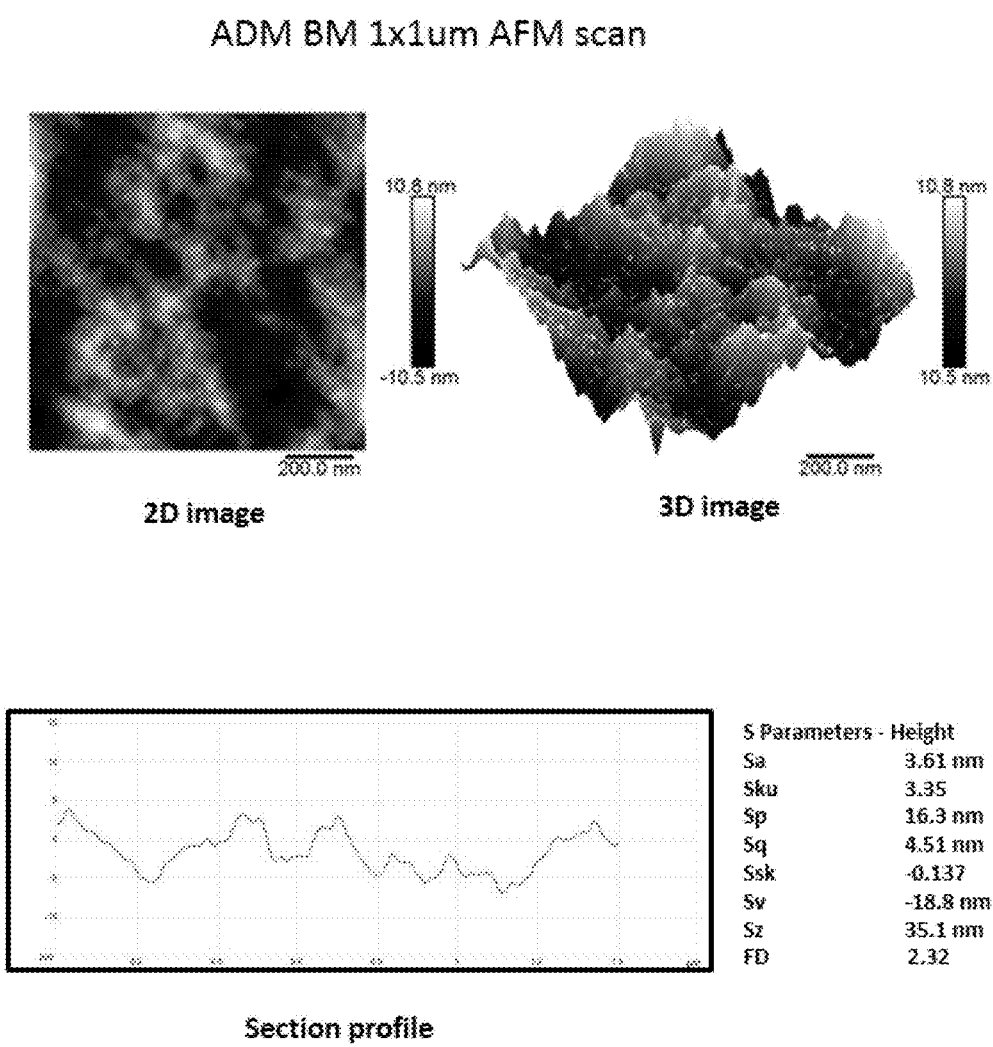
FIGS. 38A-38B show a comparison of native ADM BM (FIG. 38A) to ADM BM PDMS C (FIG. 38B) at 1×1 µm.
Figure 38B:
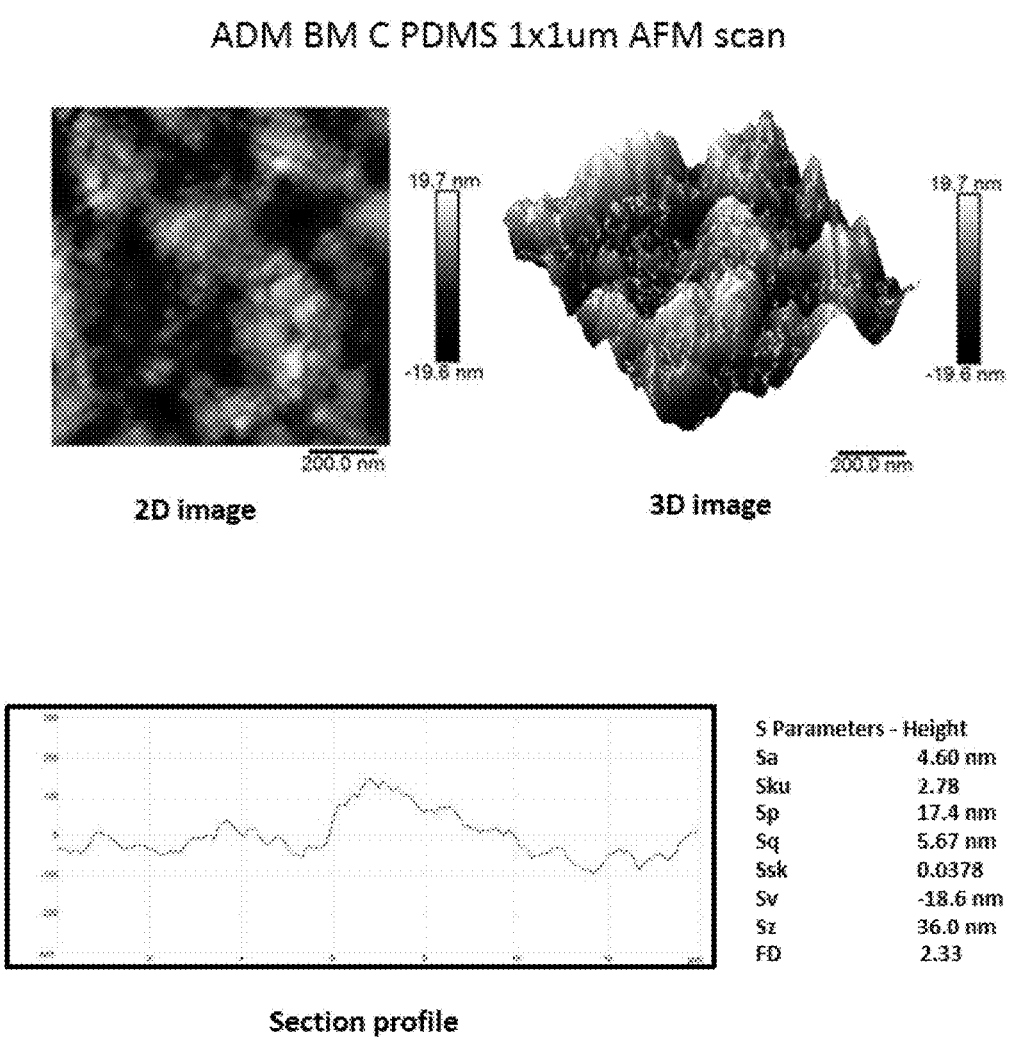
Figure 39A:
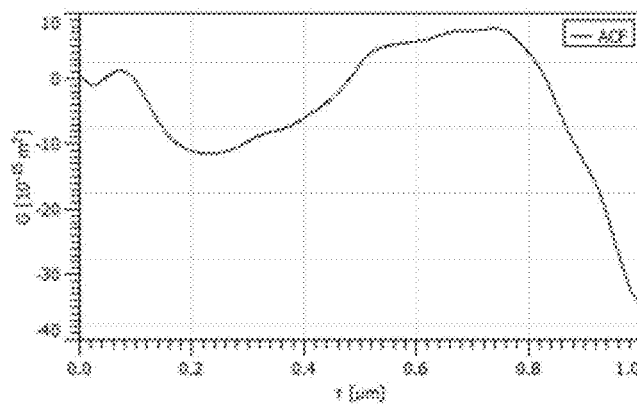
FIGS. 39A-39B show a comparison of native ADM BM (FIG. 39A) to ADM BM PDMS C (FIG. 39B) at 1×1 µm—Autocorrelation lengths.
Figure 39A:
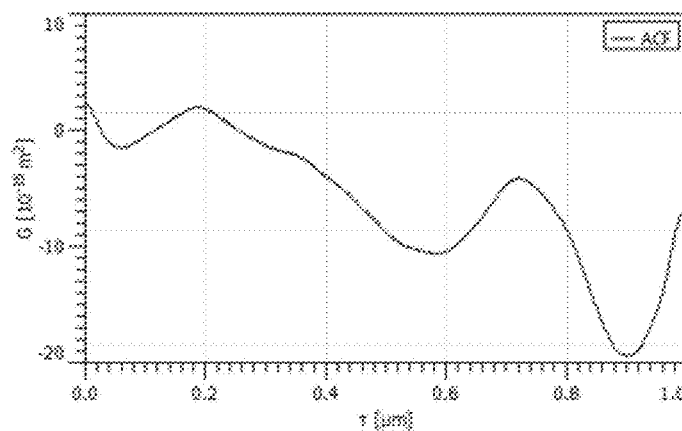
Figure 39B:
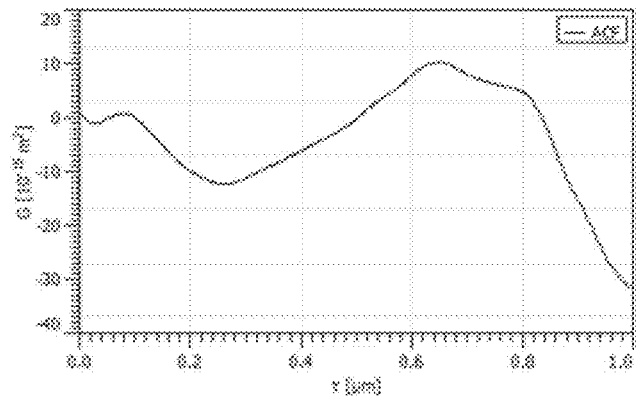
Figure 39B:
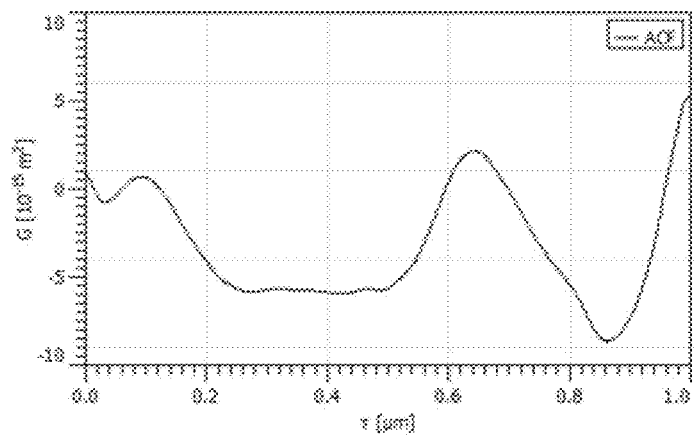
Figure 40:
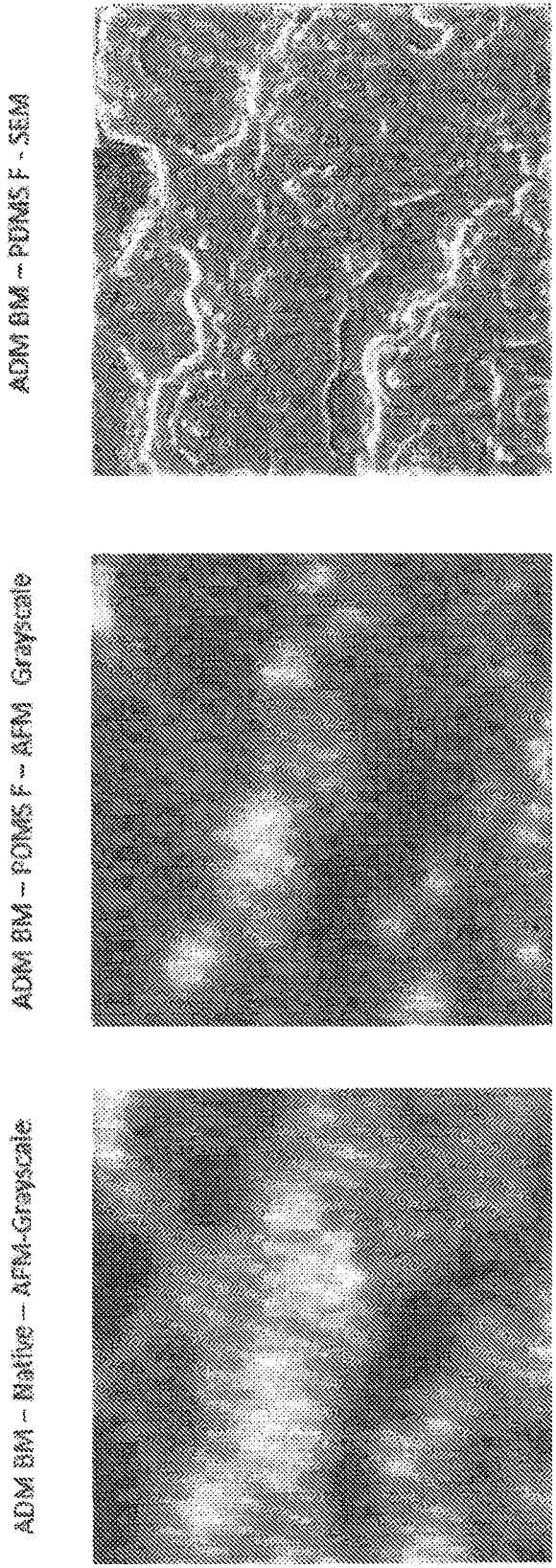
FIG. 40 shows a comparison of native ADM BM to ADM BM PDMS F AFM and SEM images at 90×90 um.
Figure 41:
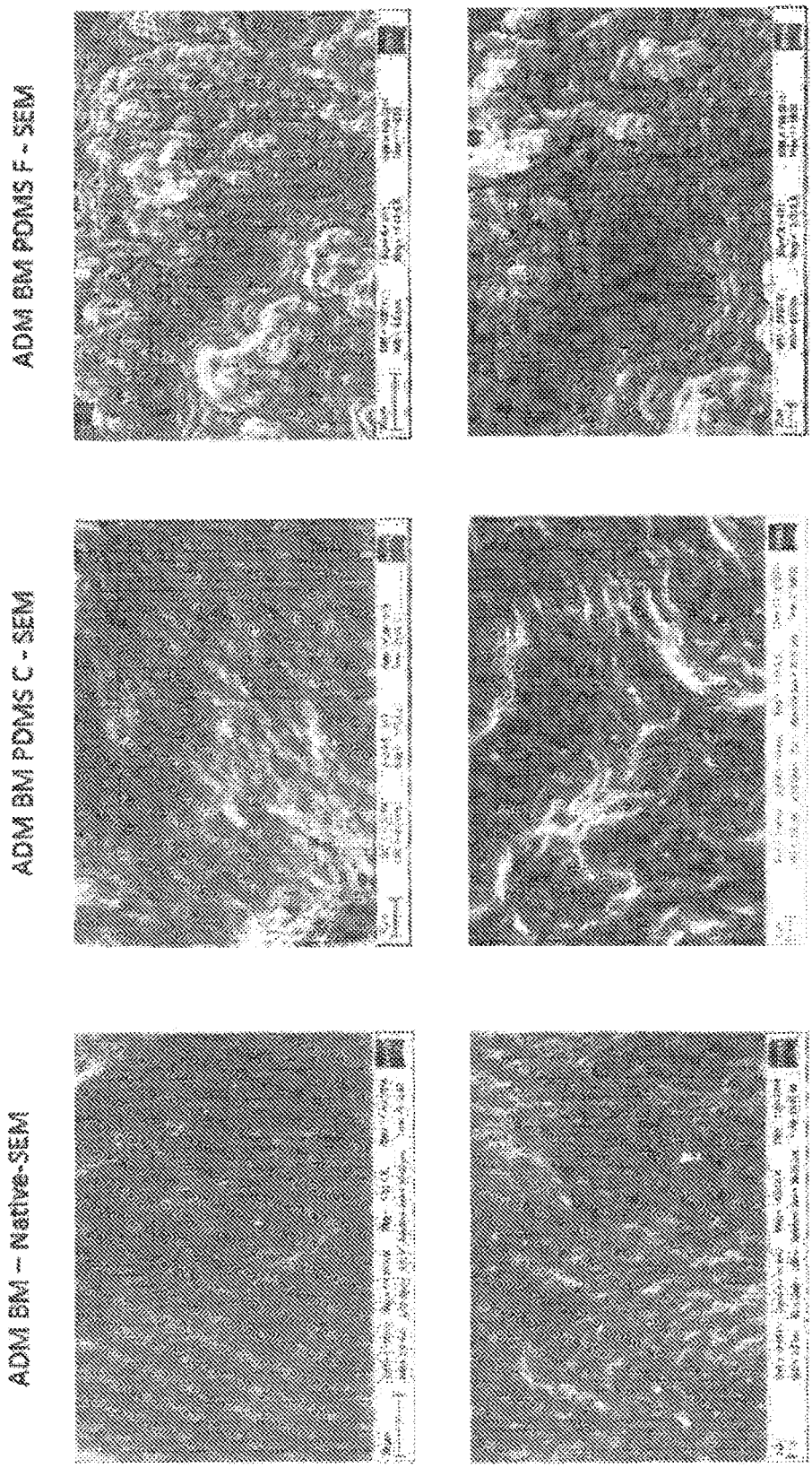
FIG. 41 shows SEM images of native ADM BM, ADM BM PDMS C and ADM BM PDMS F at different magnifications.
Figure 42:
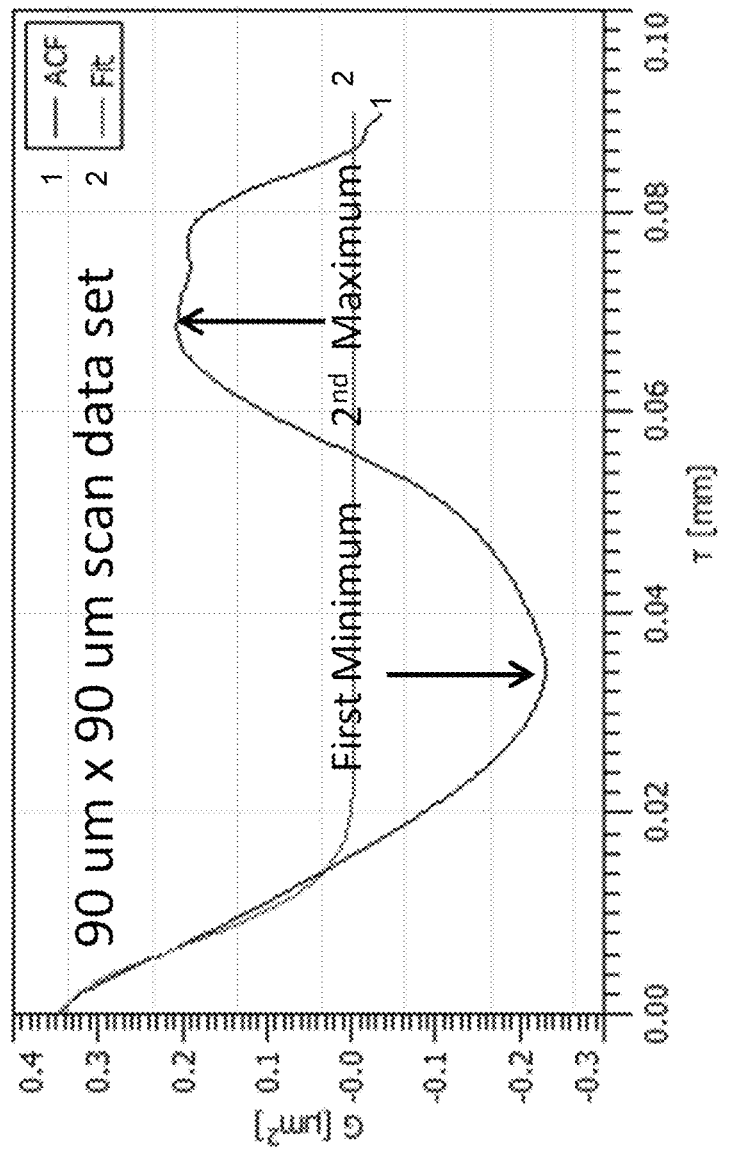
FIG. 42 depicts a horizontal ACF function with Gaussian fit. The first minimum and second minimum are indicated on the ACF data line.

The main benefit of the casting method is that it allows for more precise replication of the topographical features of ADM BM. In addition, the casting method allows replication of the full range of features of the ADM BM topography from macro to nano scale (see FIGS. 26A-26C for a comparison of natural ADM BM tissue surface and ADM BM C as cast according to the method above showing a close reproduction of the natural features in the cast implant surface).

In contrast, the fabrication method as described above is limited by the relevant range on the AFM scanner and/or the lithography technique used. Thus, lower resolution images were produced compared to the casting method but the method is more versatile and adaptation of the digital X,Y,Z information can provide a variety of surface topographies. FIG. 25 shows that the features of natural ADM BM are recreated fairly accurately using the grayscale fabrication method, although not at the same level of accuracy as the casting method. Use of Electron Beam (E-beam) Lithography to create the pattern should however allow the reproduction of features that are <50 nm in lateral resolution.

Characterisation of Implant Surfaces (Topography and Roughness)

Characterization and Quantification of Topographical Features BM/PD in Acellular Dermal Matrix (ADM) and Commercially Available Implants Preparing ADM for Characterisation The ADM was removed from storage in −20° C. freezer and allowed to thaw. Three different samples of ADM were used for analysis. Tissue was removed from foil packaging and taken out of gauze. Samples were cut into 2 cm×2 cm sections and washed in sterile PBS×3 to remove any freeze protectants. Basement membrane (BM) side of ADM is distinguished from dermal side through visually checking the tissue for roughness and a buff-colour. Further, BM characteristically repels water and the contact angle of the water is higher than on BM side than PD side. The samples were then placed BM side up onto microscope slides and allowed to slowly air dry at 4° C. for 24 hours. Samples were not fixed or critical point dried. Samples were then ready for measurement with optical microscopy, atomic force microscopy (AFM), environmental scanning electron microscopy (ESEM), Optical 3D profiler, White Light Interferometry (WLI) and profilometry.

Preparation of Comparative Examples

Commercially available implants used for comparison were Mentor Smooth and Mentor Siltex (Mentor Corporation, Santa Barbara, Calif.). Square samples of 1 cm×1 cm were cut out from implants. 3 different samples were cut from each implant and 3 different implants were used, for a total of 9 samples per implant type. Samples were sonicated in a detergent for 10 mins followed by DI water for 10 mins prior to being air dried overnight. Mentor Siltex implants were too rough for measurement with AFM and therefore Optical 3D profiling, White Light Interferometry and 3D laser scanning were used.

Characterisation of Surface Topographies

A) Characterisation of Surfaces of the Invention

ADM BM surfaces according to the invention were measured using Bruker Icon Dimension Atomic Force Microsope for scan sizes 90×90 um, 10×10 um and 1×1 um. Samples were imaged using ScanAsyst Air probes (nominal k=0.4 N/m). Imaging was conducted using ScanAsyst. PFT amplitude was 150-100 nm, and PFT frequency was 1 kHz. Scan rate was 0.5 Hz. Images were analysed using NanoScope Analysis software. A plane fit (0-2 orders) was applied prior to analysis.

AFM scans were performed at 3 different sizes. Ten images for each scan size were obtained at 90 um×90 um, 10×10 um and 1 um×1 um.

1 mm×1 mm scans of ADM BM were performed with a Bruker 3D Optical Profiler and White Light Interferometer as the AFM could not perform scans at that size.

ISO 25178 (Surface texture: areal) roughness analysis of each image was performed (using Bruker's NanoScope Analysis Software) and exported to a Microsoft Excel spread sheet for calculation of mean roughness values and standard deviation. For calculating fractal dimension and autocorrelation lengths open source online scanning probe microscopy analysis software Gwyddion was used. Matlab and Gwyddion were used for obtaining auto correlation functions of implant surfaces.

B) Comparative smooth implants (Mentor Smooth): all characterisation for these implant surfaces were measured in the same way as for ADM BM surfaces of the invention described above. Reference to smooth implants in the biological methods below refers to comparative Mentor smooth implant surfaces.

C) Comparative textured implants (Mentor Siltex): All measurements were performed with a Bruker 3D Optical Profiler, White Light Interferometer and 3D laser scanner, as the surface roughness of these implants is outside the Z range of the AFM. Reference to textured comparative surfaces in the biological methods below refers to comparative Mentor Siltex implants.

ISO 25178 (Surface texture: areal) roughness analysis of each image was performed and exported to a Microsoft Excel spread sheet for calculation of mean roughness values and standard deviation. For calculating fractal dimension and autocorrelation lengths, open source online scanning probe microscopy analysis software Gwyddion (discussed above) was used.

Data showing the ISO 25178 (Surface texture: areal) roughness values as calculated above are depicted in FIGS. 24A-24B.

Comparison of Surface Characterisation Data

The surface microstructure of ADM BM and commercially available smooth and textured implants were comprehensively characterised using optical microscopy, AFM, SEM, 3D profiling, WLI and profilometry. Roughness measurements and topographical data were gathered using a variety of experimental techniques. All surfaces were measured on at least four different length scales to ensure complete capture of roughness and topographical data and to allow comparison between them.

3D imaging and surface analysis reveal large differences in topography and roughness between ADM BM and commercially available implants. Textured implants (Mentor Siltex, Sa=8.24 µm) were more than 20 times rougher than ADM BM (Sa=0.48 µm) and around 400 times rougher than smooth implants (Mentor Smooth, Sa=0.022 µm) at similar length scales The Sa (arithmetic mean of values) of ADM BM varied at different image sizes and ranged from 6.7 µm at 1 mm×1 mm scans down to 5.84 nm for a 1 µm×1 µm scan. The Sa of smooth implants ranges from 82.65 nm at 1 mm×1 mm to 4.36 nm at 1 µm×1 µm scans while textured implants range from 41.73 µm at 1cm×1cm to 8.24 at 100 µm×100 uµm. ADM BM surface topography according to the invention is therefore considerably rougher than smooth implants while significantly less rough than textured implants.

The Sz (Maximum height of the surface (Distance between maximum valley depth and maximum peak height) of ADM BM ranges from 43 µm for 1 mm×1 mm scans to 46.9 nm for 1 µm×1 µm scans. This is in comparison to textured implants where the Sz ranged from 273 µm for 1 cm×1 cm scans to 40 µm for 100 µm×100 µm scans. Further, smooth implants Sz ranged from 1.2 µm for 1 mm×1 mm scans to 46.64 nm for 1×1 µm scans. The maximum feature heights on textured implants are therefore considerably larger than on ADM BM surfaces of the invention and comparative smooth implants while ADM BM contains maximum feature heights that are larger than those on smooth implants at every length scale.

Ssk (Skewness) describes the degree of symmetry of surface heights about the mean, i.e. whether a surface possess a predominance of either peaks or valleys. A negative Ssk indicates a predominance of valleys and a positive Ssk indicating a predominance of peaks. Measured ADM BM surface Ssk (skewness) was found to be approximately 0 at all length scales ranging from 0.14 at 1 mm×1 mm scans to −0.04 at 1 μm×1 μm scans. The Ssk values are all very close to 0 indicating neither a predominance of peaks nor valleys but an equal contribution of both. This is in contrast to the varying Ssk value for textured implants (Mentor Siltex) of 0.57 for 1 cm×1 cm scans to −0.02 for 100 μm×100 μm scans indicating variation in peak to valley ratio at different length scales, but with a predominance of peaks at increased length scales. Comparative smooth implants (Mentor Smooth) had a positive skewness at length scales ranging from 3.58 for 1 mm×1 mm scans to 0.11 to 1 μm×1 μm indicating a predominance of peaks at all length scales.

Sku (kurtosis) describes the likelihood of a surface having a feature which is significantly deviated from the mean. Excess Sku values will be used to describe Sku values throughout these results. It is calculated by Sku−3. A surface which contains features that significantly and abruptly deviate from the mean will have a positive Sku (Sku>0) where as a surface which is gradually varying will have a negative Sku (Sku<0). A surface which contains a bell-shaped curve of normal distribution has a Sku of 0. A surface having a Sku of 3 shows a Gaussian distribution. Thus, a surface having an excess kurtosis (Sku−3) of zero shows Gaussian distribution.

ADM BM according to the invention possesses excess kurtosis (Sku) values of close to 0 at all length scales indicating that surface features of ADM BM are normally distributing. ADM BM possess an exess Sku of −0.15 for 1 mm×1 mm scans down to −0.1 for 1 μm×1 μm scans. This is in contrast to the positive Sku values of smooth implants at all lengths, ranging from 26.7 for 1 mm×1 mm scans to 0.93 for 1 μm×1 μm scans. This indicates that smooth implants (Mentor Smooth) are predominantly flat but contain repeating and random small peaks on the surface. The negative Sku values of textured implants (Mentor Siltex), ranging from −1.88 for 1 cm×1 cm scans to −3.21 for 100 μm×100 um scans indicate a more gradually varying surface with predictable variations from the mean.

Considering Ssk and Sku values together it may be said that the ADM BM surface measured is a self-similar surface with similar Ssk and Sku values at all length scales. It has a roughly equal distribution of peaks and valleys that are gradually varying. The surfaces fit a normal distribution and the graph would be shaped like the "bell curve". Textured implants can be described as a being macroscopically rough with repetitive and repeatable features with a slight predominance of peaks which are gradually varying and predictable. Smooth implants are macroscopically smooth surfaces which contain features which are predominantly peaks which abruptly deviate from the mean and are random.

The fractal dimension (FD) of ADM BM at all size scans is approximately 2.3, ranging from 2.37 for 1 mm×1 mm scans to 2.29 for 1 um×1 um scans. A fractal dimension of a plane is 2 and a cube is 3 therefore the fractal dimension of ADM BM indicates a planar surface with 3D features on it. As the FD is consistent across all scan sizes it suggests that the same surface topography is present but at different scales; macro, micro and nano-scale topographies. This is classical self-similarity commonly found in nature.

The FD of textured implants varies with scan size. It ranges from 2.81 for 1 cm×1 cm scans to 2.05 for 100 um×100 um scans. This indicates that it goes from being a 3D surface to one that can nearly be considered planar. This is because the topography and roughness of textured implants vary greatly depending on the area over which they are measured; containing distant macroscopic features but is mostly smooth at the micron and nano-scale level.

The FD of smooth implants also varies with scan size. It ranges from 2.07 for 1 mm×1 mm scans to 2.36 at 1×1 um scans (and 2.59 at 10×10 um scans). This indicates that smooth implants are practically planar and flat when measured over a large area and becomes gradually rougher on the micron and nanoscale at smaller scan sizes. It can be described as macroscopically and microscopically smooth at large scan sizes and nanoscopically rough at very small scan sizes.

Production of Surfaces Having Variations of the Values Measured

Modification of autocorrelation functions derived from these measurements could be used to filter the Gaussian distribution of features to create a model surface of ADM BM with a fractional dimension of 2.3.

General Biological Methods

Isolation of Breast Derived Fibroblasts (BDF's) from Breast Tissue and Cell Culture Breast derived fibroblasts (BDF's) were used for all studies to represent the cells which will encounter the implants if they were inserted into breasts in vivo. Informed consent was taken from each patient undergoing surgery and written ethical approval was gained from local Ethical Committee. It has been shown that the site of tissue harvest contains fibroblasts, which are site specific. Fibroblasts from different body sites have different genotypic and cytokine profiles so it was important to use breast derived fibroblasts to most accurately re-create the in vivo environment in vitro and also allow stronger conclusions to be made as to how the effect of the different implants on cells may be realised in vivo (clinical application).

Primary cell culture of breast gland and connective tissue, to obtain BDF's, was performed. Cells were grown in T75 tissue culture plastic (TCP) flasks (Corning Incorporated, USA) in growth media containing Dulbeccos Modified Eagle Medium (DMEM) (Sigma Aldrich, Aldrich, UK) supplemented with 10% FBS (PAA, Austria) Penicillin (100 units/ml), streptomycin (100 units/ml) and L-Glutamine (2 mM, PAA Austria). They are incubated at 37° C. in humidified in 5% $CO_2$ air. Growth media is changed every 48 hours and cells passaged at 70-90% confluence. All BDf's used in the following experiments are of passage 3 in an effort to retain the cells innate genotypic and phenotypic characteristics before they're removed with excessive passaging.

Cell Attachment and Cell Proliferation (MTT Assays)

For cell attachment and proliferation rate studies, 10,000 cells per well (24 well plate) were seeded. Each experiment was performed three times, in triplicates. MTT assays were performed on ADM BM F according to the invention (prepared by the grayscale fabrication method described above), ADM BM C according to the invention (prepared by the casting method described above), comparative smooth implants, comparative textured implants, comparative tissue culture plastic (TCP) and comparative collagen.

Cell attachment experiments were performed using an MTT assay (Cell proliferation Kit 1 (MTT), Roche, Mannheim, Germany), as per manufacturer instructions. It is a colorimetric assay in which the tetrazolium salt MTT gets cleaved intracellularly within viable cells, which after the cells have been solubilized, produces a purple formazan dye. This can be measured using a microplate reader at a wavelength of between 570-650 nm and after background has been removed an absorbance (optical density) value can be obtained.

Cell Survival (LDH Assay)

Cell survival was determined using the lactose dehydrogenase (LDH) enzyme, which is released by damaged cells into the growth media. The levels of LDH released by damaged cells into the growth medium can be measured as per manufacture instructions, using a micro-plate reader and measured between a wavelength of 490-660 nm (Cytotoxicity Detection Kit, Roche Mannheim, Germany).

RNA Extraction, cDNA Synthesis and Quantitative Real Time Polymerase Chain Reaction (QRT-PCR)

Following BDF culture on different surfaces, cells were collected in TRIzol buffer (Invitrogen, UK). RNA extraction, cDNA synthesis and QRT-PCR were carried out to manufacturers instructions, using standard protocol in our laboratory and as described previously [Shih 2012] & [Shih 2010]. RNA concentration and purity were analysed on NanoDrop 2000c (Thermo Scientfic, Rockford, Ill.). RNA concentration was normalized prior to cDNA synthesis. cDNA synthesis was carried out using qScripts cDNA synthesis kit (Quanta Biosceinces, Gaithersburg, Md.). QRT-PCR was performed on LightCycler 480 machine (Roche Diagnostics, Germany), as described previously [Shih 2010] & [Syed 2011]. Primers and probes used for QRT-PCR are shown in table below. Delta CT values were calculated by subtracting averaged RPL32 (reference gene) CT values from averaged CT values of target gene. Relative gene expression levels were calculated by using $2^{-\Delta\Delta C_T}$ method.

wrapped in foil. Surfaces were visualised on an upright immunofluorescence microscope and images recorded. (BX51, Olympus UK Ltd)

SEM

BDF's that had been cultured on different surfaces were fixed in 10% Neutral buffered formalin (NBF) for 1 hour. They were then dehydrated in graded, increasing alcohol concentrations of 50%, 60%, 70%, 80%, 95% and 100%×2, for 10 mins each. Surfaces were dried, sputtered with gold and then immediately imaged using FEI SEM+ESEM.

Statistical Analysis

All experiments were performed three times, in triplicates. All statistical tests were performed using Prism 6 software. Relative absorbance (OD) values of the colorimetric MTT/LDH assays were used for cell attachment, cell proliferation and cell survival comparisons. Two-way ANOVA followed by Turkey post-hoc multi-comparison analysis was performed on cell attachment, proliferation rate and cell survival data. To determine the difference in gene expression between BDF's on different surfaces the relative threshold cycle ($C_T$) was used, obtained from PCR. Relative gene expression was calculated using the $2^{-\Delta\Delta C_T}$ method and used for comparison. One way ANOVA followed by Turkey post-hoc multi-comparison analysis was performed on QRT-PCR data. A p value of less than 0.05 was considered as statistically significant in all experiments.

TABLE 1 genes and primers used for QRT-PCR

| Target gene | Primer Sequence | Universal Prober Number |
| --- | --- | --- |
| Proliferating cell nuclear antigen (PCNA) | Left: tggagaacttggaaatggaaa<br>Right: gaactggttcattcatctctatgg | #69 |
| Vinculin (VCL) | Left: ctgaaccaggccaaaggtt<br>Right: gatctgtctgatggcctgct | #89 |
| Interleukin 8 (IL8) | Left: agacagcagagcacacaagc<br>Right: atggttccttccggtggt | #72 |
| Tumour necrosis factor alpha (TNF-α) | Left: agcccatgttgtagcaaacc<br>Right: tctcagctccacgccatt | #79 |

Immunocytochemistry

Immunocytochemistry was performed on BDF's for vinculin, F-Actin and DAPI. BDF's cultured on different surfaces were fixed in 10% Neutral buffered formalin (NBF) for 1 hour, washed in PBS and permeabilised in 0.5% Triton-X 100 for 25 minutes. Cells were washed again with PBS and blocked in blocking solution (1% BSA) for 1 hour at room temperature on a shaker at 55 RPM. After washing, cells were incubated overnight at 4° C. with Mouse-Monoclonal Anti-vinculin primary antibody (SPM227, ab18058, Abcam, UK), at a dilution of 1:50 in PBS. The following steps are performed in the dark. Cells are washed with PBST (0.1% tween in PBS) and then incubated with the secondary antibody Anti-rabbit Alexa Fluor-488 dye (Invitrogen, UK) in a 1:200 dilution on a shaker at 55 RPM for 1 hour at room temperature, wrapped in foil. After washing in PBST, cells were incubated with Rhodamine phalloidin stain (1:200) (Sigma-Aldrich, UK) for 45 mins at room temperature. Cells are again washed with PBST before incubate with DAPI (1:500) (Invitrogen, UK) for 15 minutes at room temperature. Surfaces were washed with PBST, mounted with Prolong gold (Invitrogen, UK) and stored in cold room, Cellular Response Data In vitro evaluations of Breast Derived Fibroblast (BDF) cell attachment, proliferation, survival, genotype and phenotype on ADM BM F (fabricated according to example 1) and ADM BM C (cast according to example 2) PDMS implants according to the invention were performed. These data were compared against data for conventional smooth and textured implants inter alia and showed improved properties in all tested areas as mentioned below.

1) Cell Attachment

Figure 2:
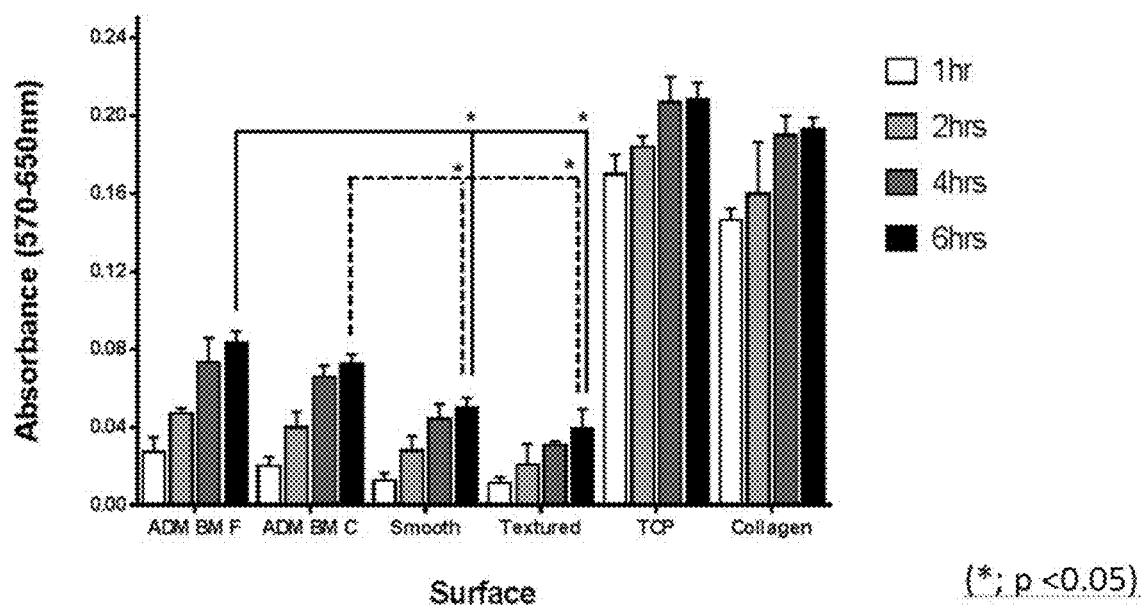
FIG. 2 depicts breast derived fibroblast (BDF) cellular attachment data over 1 to 6 h on ADM BM C and ADM BM F surfaces according to the invention (as prepared according to the casting and fabrication methods of the invention respectively—see examples 1 and 2) as compared to growth on comparative smooth and textured implants, TCP and collagen.

As seen in FIG. 2, cell attachment of BDF's was significantly greater after 2 hours on both ADM C and ADM F surfaces according to the invention as compared to smooth and textured implants, which persisted up to the 6 hour time point. During the first 1 hr of cell culture there was no observed difference in cell attachment between implant surfaces. However, by 2 hrs, significantly more BDF's had attached to ADM surfaces of the invention in comparison to smooth and textured implants. This effect was observed through 4 and 6 hours, with most significant differences observed after 6 hours. After 6 hours, cell attachment of BDF's on both ADM BM F and ADM BM C surfaces of the invention was significantly greater than on smooth (ADM BM F p<0.0001; ADM BM C p=0.042) and textured (ADM BM F p<0.0001; ADM BM C p<0.0001) implants. Further, there was no significant difference between cell attachment on smooth or textured implants after 6 hours, and no significant difference between ADM BM C and ADM BM F.

Figure 3:
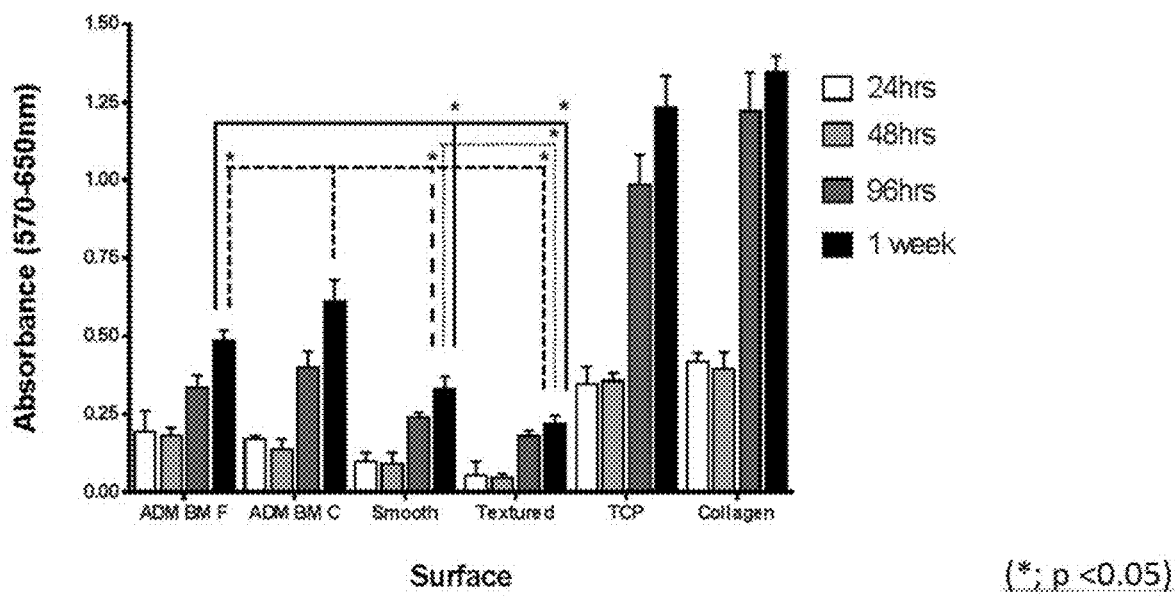
FIG. 3 depicts breast derived fibroblast (BDF) cellular proliferation data for up to 1 week on ADM BM C and ADM BM F surfaces according to the invention (as prepared according to the casting and fabrication methods of the invention respectively—see examples 1 and 2) as compared to growth on comparative smooth and textured implants, TCP and collagen.

2) Proliferation Rate (MTT Assay)—Proliferation of BDF's on ADM C and ADM F was Significantly Greater than on Smooth and Textured Implants After 24 Hours which Progressively Increased and Continued up to 1 Week As seen in FIG. 3, after 24 hours significantly increased cell proliferation was observed on ADM surfaces according to the invention in comparison to smooth (ADM BM F p=0.034; ADM BM C p=0.045) and textured implants (ADM BM F p=0.0034; ADM BM C p=0.0049), which although plateauing, was still significant at 48 hours. By 96 hours there was a clear increase in proliferation of BDF's on ADM surfaces in comparison to smooth and textured which became most significant after 1 week (after 1 week, ADM BM F vs. smooth p0.015; vs. textured <0.0001; ADM BM C vs. smooth p<0.0001; vs. textured p<0.0001). After 1 week, there was significantly increased BDF proliferation on smooth implants in comparison to textured (p0.0363). Further, after 1 week there was significantly increased proliferation of BDF's on the ADM BM C surface in comparison to the ADM BM F surface (p0.0017). These data indicate by comparison of the ADM BM F and ADM BM C the improved effect on cellular proliferation achieved by the novel sub-micro and nano-scale roughness features present in the ADM BM C surfaces (included in the ADM BM C surfaces as a result of the increased resolution of the casting method over the fabrication method of the invention described herein).

Figure 4:
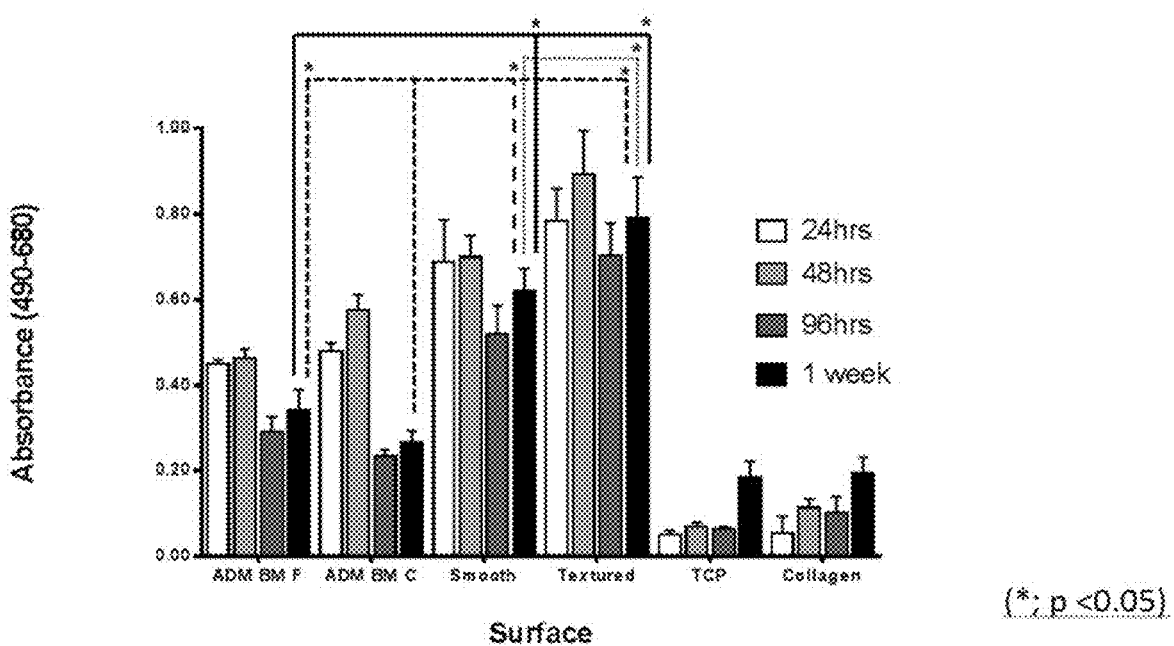
FIG. 4 depicts breast derived fibroblast (BDF) cell survival data for up to 1 week on ADM BM C and ADM BM F surfaces according to the invention (as prepared according to the casting and fabrication methods of the invention respectively—see examples 1 and 2) as compared to growth on comparative smooth and textured implants, TCP and collagen.

3) Cell Survival (LDH Assay)—BDF's on ADM Surfaces Showed Less Apoptosis (Increased Cell Survival) at Every Time Point As seen in FIG. 4, LDH assay revealed improved BDF survival on ADM surfaces according to the present invention at every time point in comparison to conventional smooth and textured implants. This was most significant after 96 hours and continued up to 1 week (at 1 week, ADM BM F vs. smooth <0.0001; vs. textured <0.0001; ADM BM C vs. smooth p<0.0001; vs. textured p<0.0001). In addition, increased cell death was observed in BDF's cultured on textured implants in comparison to smooth implants after 1 week (p0.0023). Further, at 1 week there was significantly increased cell survival of BDF's on ADM BM C surface in comparison to ADM BM F surface (p0.043). These data again indicate by comparison of the ADM BM C and ADM BM F data the improved effect on cellular proliferation of the sub-micro and nano-scale surface roughness features present in the ADM BM C surfaces as a result of the increased resolution of the casting method over the fabrication method of the invention described herein.

4) QRT-PCR—Changes in Gene Expression of BDF's Cultured on Different Implant Surfaces for 96 Hours a) PCNA PCNA (proliferating cell nuclear antigen) is a gene, which becomes highly expressed during DNA synthesis and DNA repair. Cells which are proliferating (Undergoing mitosis) are constantly synthesizing new DNA prior to replication. Therefore, PCNA is a measure of cell proliferation levels.

Figure 5:
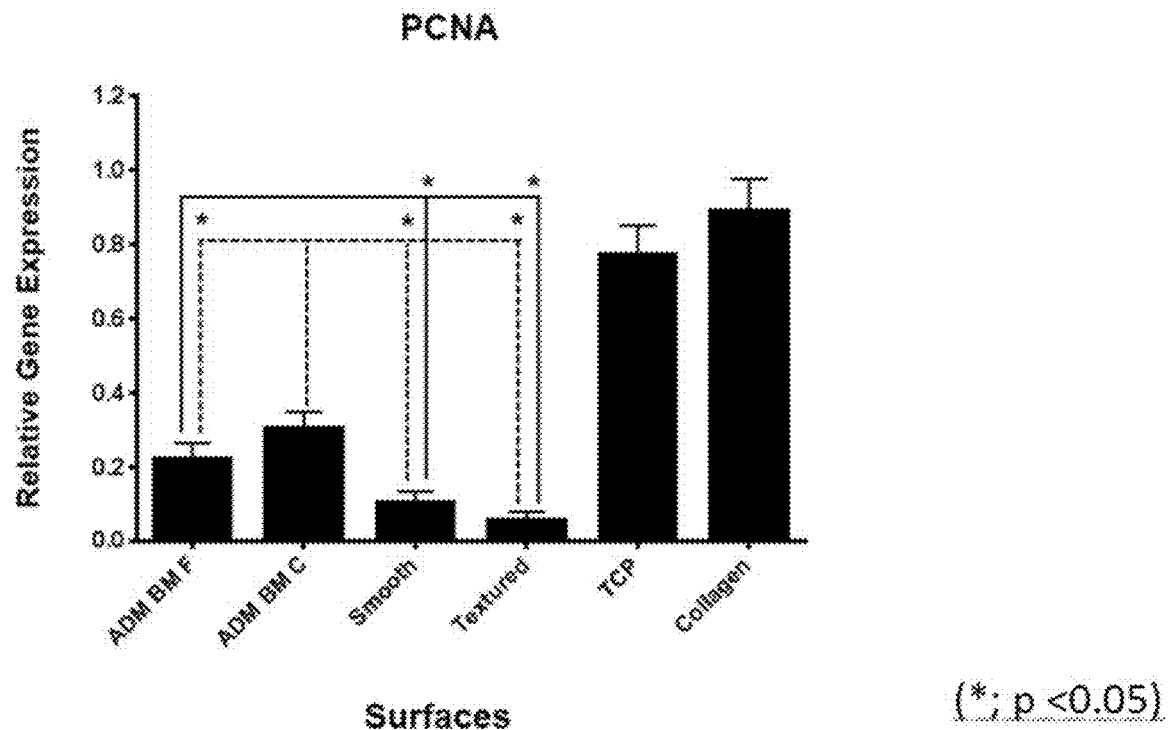
FIG. 5 depicts QRT-PCR data showing changes in PCNA (proliferating cell nuclear antigen) gene expression of breast derived fibroblast (BDF's) grown on ADM BM C and ADM BM F surfaces according to the invention (as prepared according to the casting and fabrication methods of the invention respectively—see examples 1 and 2) as compared to growth on comparative smooth and textured implants, TCP and collagen for 96 h.

As seen in FIG. 5, PCNA was significantly up-regulated on ADM surfaces according to the present invention in comparison to smooth and textured implants (ADM BM F vs. smooth 0.034; vs. textured 0.0014; ADM BM C vs. smooth p<0.0001; vs. textured p<0.0001). Further, PCNA was significantly up-regulated in BDF's cultured on ADM BM C in comparison to ADM BM F (p0.0069). In addition, there was significant difference in PCNA expression of BDF's on smooth and textured implants.

This PCNA data correlates well with the cell proliferation data gathered from MTT experiments, e.g. reinforcing the improved proliferation data for ADM BM C material observed over ADM BM F.

b) Vinculin

Vinculin is a membrane-cytoskeletal protein that plays an essential part in the focal adhesions formed between cells and there environment. Firm focal adhesion formation is important for cell attachment and subsequent cell spreading, migration and proliferation. Further, mechano-transduction (the method by which cells are able to convert mechanical stimulus from their environment e.g. implant surface or ECM and turn into chemical activity, such as a change in secretion of a cytokine) is crucial to cell function and response to environment.

Figure 6:
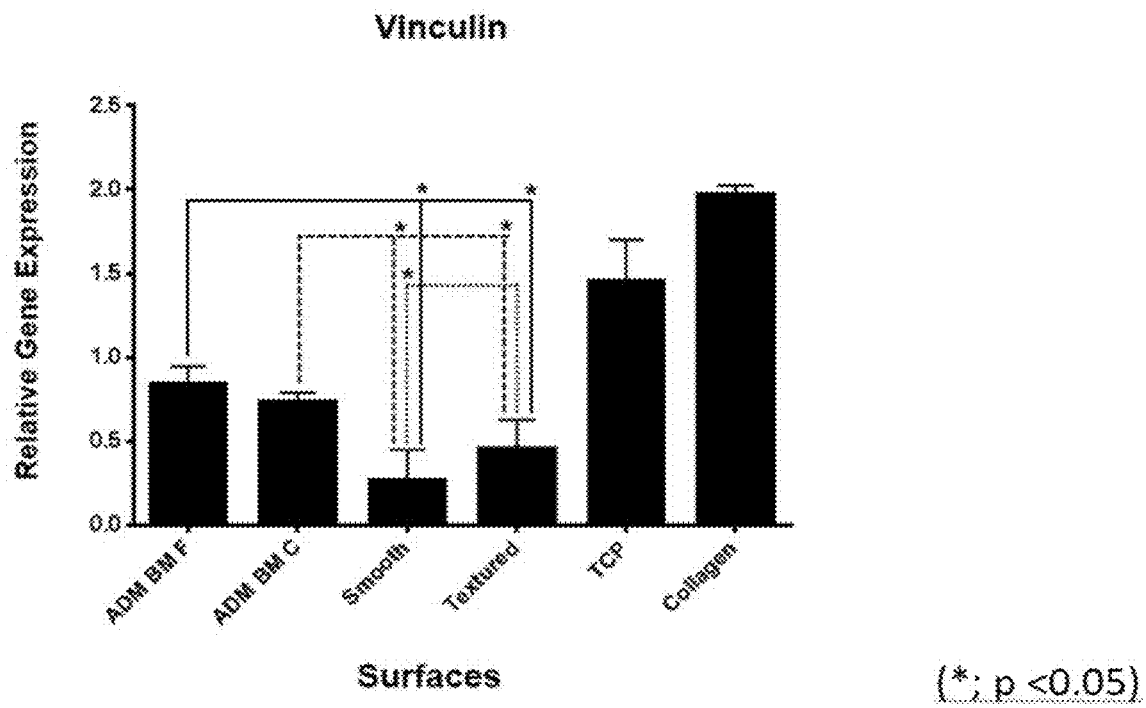
FIG. 6 depicts QRT-PCR data showing changes in vinculin gene expression of breast derived fibroblast (BDF's) grown on ADM BM C and ADM BM F surfaces according to the invention (as prepared according to the casting and fabrication methods of the invention respectively) as compared to growth on comparative smooth and textured implants, TCP and collagen for 96 h.

As seen in FIG. 6, vinculin was significantly up-regulated on ADM surfaces according to the invention in comparison to smooth and textured implants (ADM BM F vs. smooth 0.0092; vs. textured 0.0008; ADM BM C vs. smooth p<0.03; vs. textured p<0.01). Further there was no significant difference between BDF's cultured on ADM BM F in comparison to ADM BM C (p0.19).

Up-regulation of the vinculin gene in BDF's cultured on ADM BM surfaces correlates with cell attachment experiments above.

c) IL8

IL8 (Interleukin 8) is an acute inflammatory chemokine and plays a key role in recruiting neutrophils to the wound after injury. It is associated with many inflammatory conditions such as rheumatoid arthritis and psoriasis. It also plays a role in angiogenesis, and is associated with a number of fibrotic conditions such as cystic and pulmonary fibrosis. It has previously been found to be up-regulated in contracted breast capsules [Kyle 2013].

Figure 7:
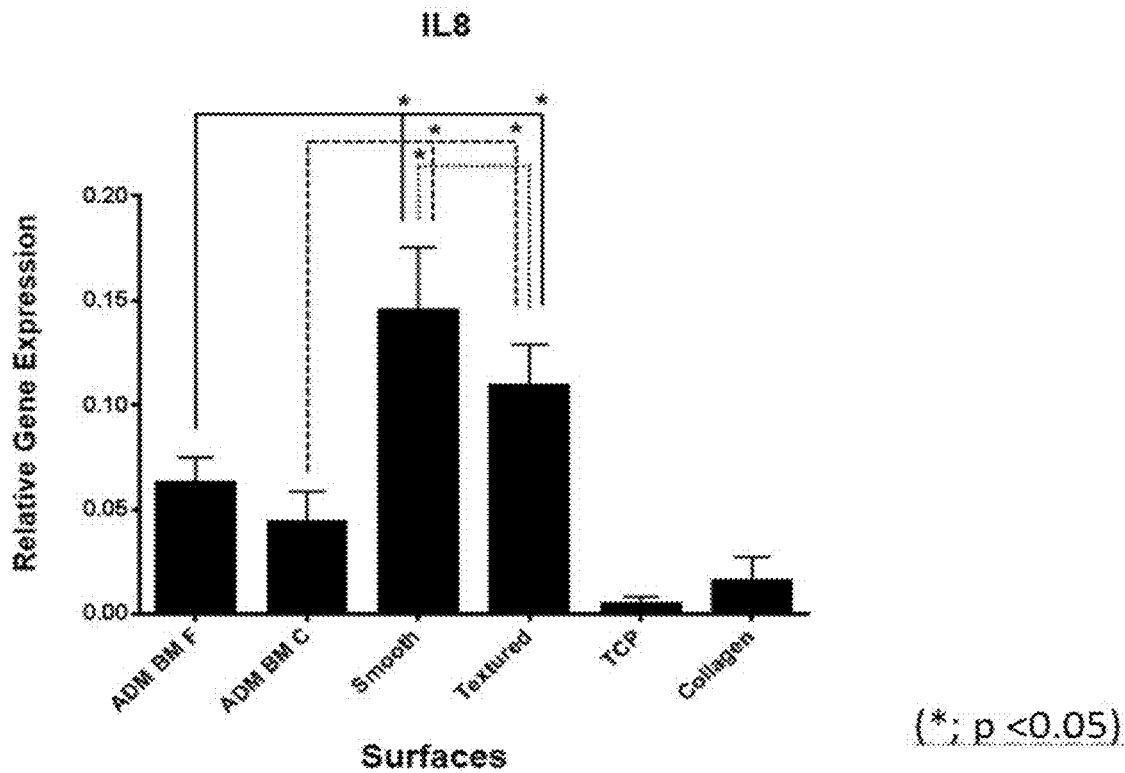
FIG. 7 depicts QRT-PCR data showing changes in IL8 (Interleukin 8) gene expression of breast-derived fibroblast (BDF's) grown on ADM BM C and ADM BM F surfaces according to the invention (as prepared according to the casting and fabrication methods of the invention respectively—see examples 1 and 2) as compared to growth on comparative smooth and textured implants, TCP and collagen for 96 h.

As seen in FIG. 7, IL8 was significantly down-regulated on ADM implant surfaces of the invention in comparison to smooth and textured implants (ADM BM F vs. smooth p<0.0001; vs. textured p<0.0037; ADM BM C vs. smooth p<0.0001; vs. textured p<0.0001). There was no significant difference IL8 expression between BDF's cultured on ADM BM F in comparison to ADM BM C (p0.45). Lastly, there was a significant down-regulation of IL8 in BDF's cultured on textured implants in comparison to BDF's on smooth implants (p0.0043).

d) TNF Alpha

TNF-alpha (Tumour necrosis factor alpha) has been shown to be a pro-inflammatory cytokine that stimulates the acute phase reaction. TNF alpha has been shown to be associated with capsular contracture formation in a number of studies, see e.g. [Tan 2010] & [D'Andrea 2007].

Figure 8:
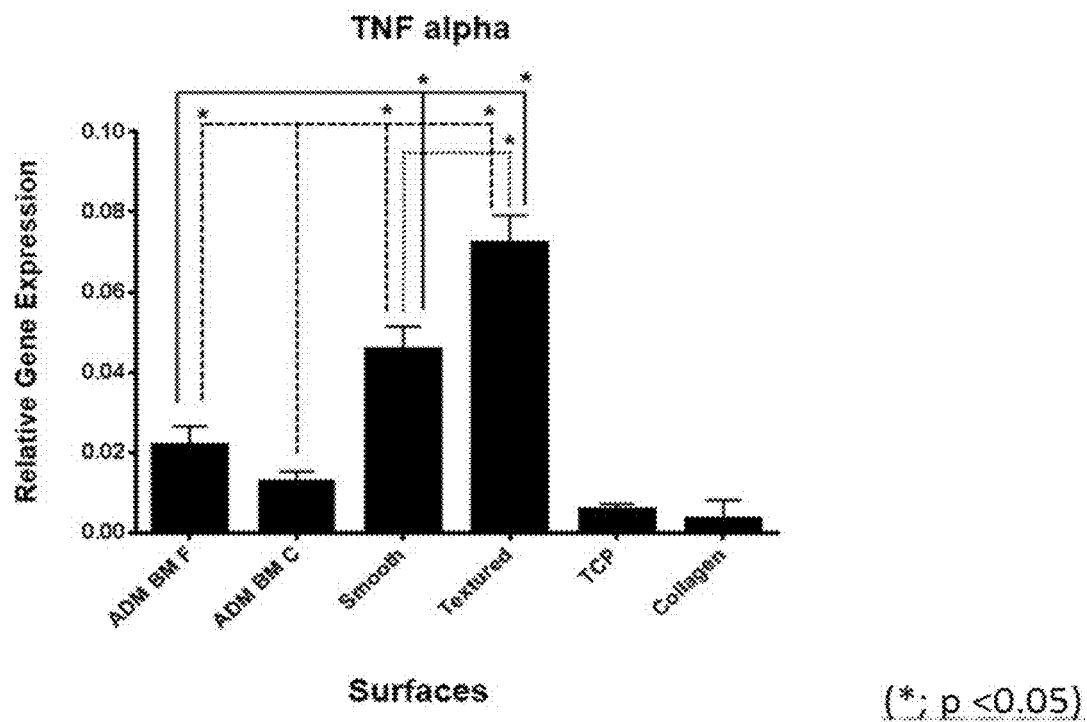
FIG. 8 depicts Quantitative Real Time Polymerase Chain Reaction (QRT-PCR) data showing changes in TNF-alpha (Tumour necrosis factor alpha) gene expression of breast derived fibroblast (BDF's) grown on ADM BM C and ADM BM F surfaces according to the invention (as prepared according to the casting and fabrication methods of the invention respectively—see examples 1 and 2) as compared to growth on comparative smooth and textured implants, TCP and collagen for 96 h.

As seen in FIG. 8, TNF alpha was significantly down-regulated on implant surfaces of the invention in comparison to smooth and textured implants (ADM BM F vs. smooth p<0.0001; vs. textured p<0.0001; ADM BM C vs. smooth p<0.0001; vs. textured p<0.0001). Further, TNF alpha was significantly down regulated in BDF's cultured on ADM BM C in comparison to ADM BM F (p0.023). Lastly, there was a significant down-regulation of IL8 in BDF's cultured on smooth implants in comparison to BDF's on textured implants (p<0.0001).

5) Immunofluorescence—Cell Morphology and Phenotype

Figure 9A:
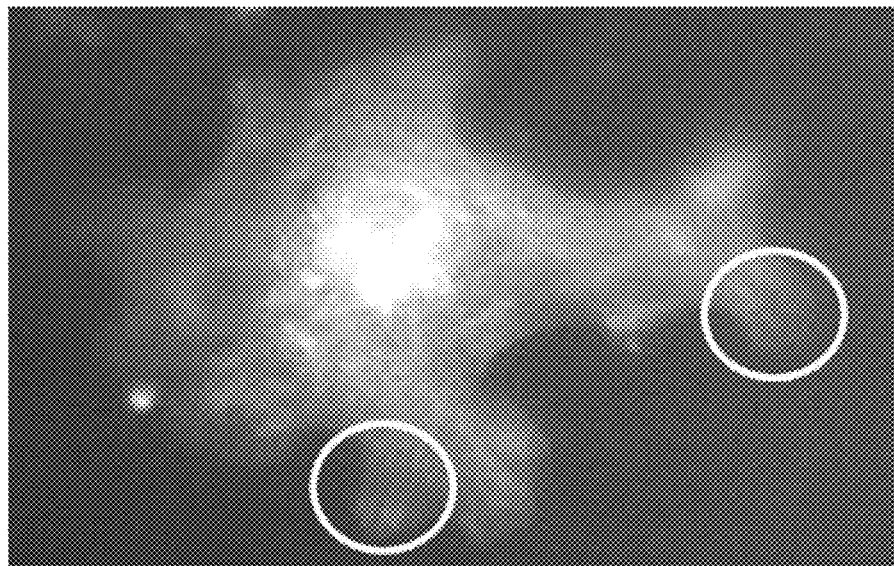
FIGS. 9A-9B depict immunofluorescence cell morphology and phenotype data for BDF's grown on ADM BM C (90×90 μm) according to the invention (as prepared according to the casting method of the invention). The images show staining of F-Actin (red in original colour images), vinculin (green in original colour images) and Dapi (blue in original colour images). White circles highlight vinculin staining and focal adhesion formation.
Figure 9B:
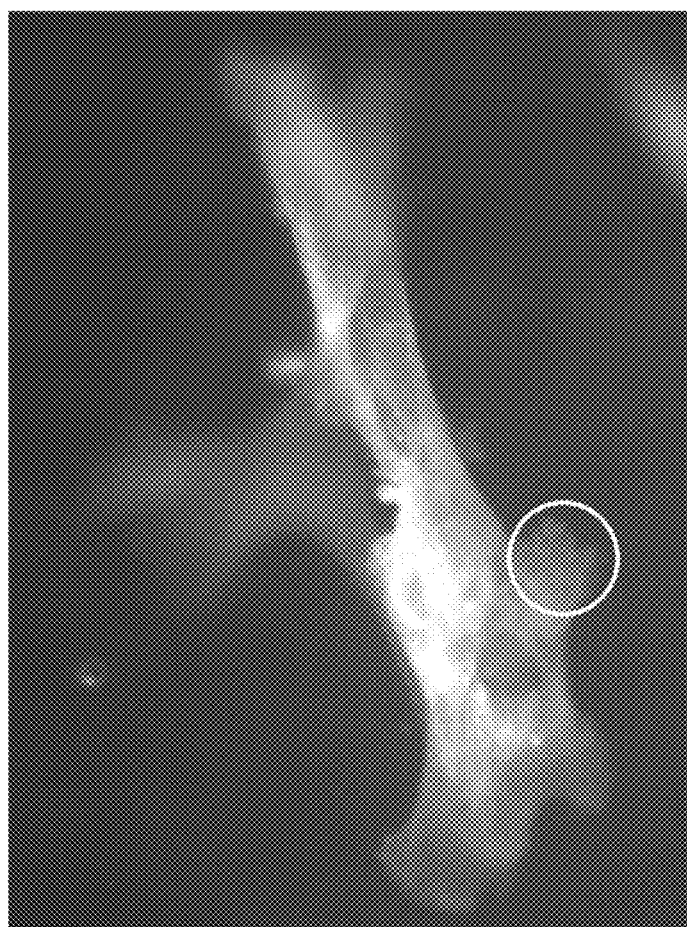

Example: BDF's on ADM BM C (in the initial colour images, Red=F-Actin, Green=vinculin and Blue=Dapi. White circles highlight vinculin staining and focal adhesion formation As seen in FIGS. 9A-9B, immunofluorescence images revealed specific focal staining of vinculin in BDF's on ADM BM surfaces. The focal adhesion has the characteristic shape of the focal adhesions of fibroblasts, with localised and defined staining of vinculin (as identified by white circles). The raw colour data show many green "streaks" which are each a focal adhesion point where the BDF has attached to a feature on the ADM BM surface. These images reveal that BDF's on ADM BM surfaces have attached well, and have subsequently spread to develop typical fibroblast morphology.

Comparative Example: BDF's on Mentor Smooth Implants (in the Initial Coloured Images: Red=F-Actin, Green=Vinculin and Blue=Dapi)

Figure 10A:
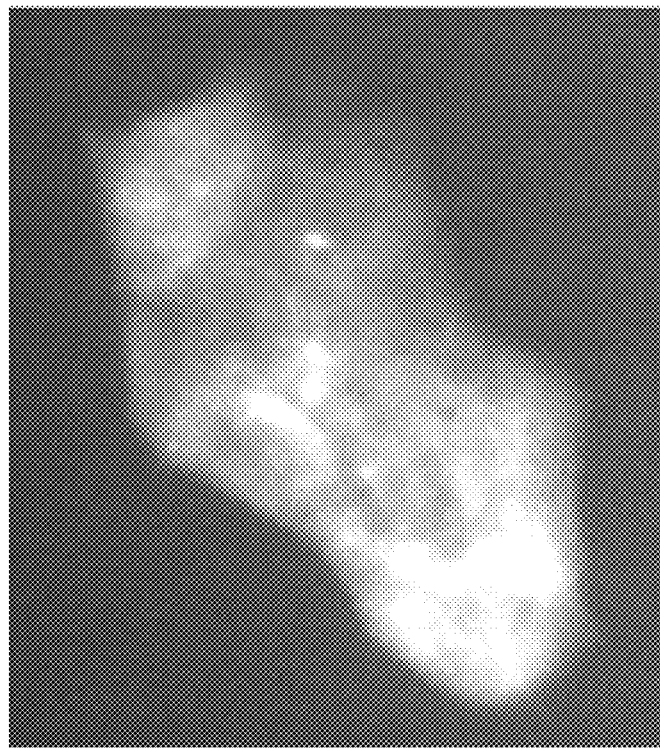
FIGS. 10A-10B depict immunofluorescence cell morphology and phenotype data for BDF's grown on comparative smooth implants (Mentor smooth). The images show staining of F-Actin (red in original colour images), vinculin (green in original colour images) and Dapi (blue in original colour images).
Figure 10B:
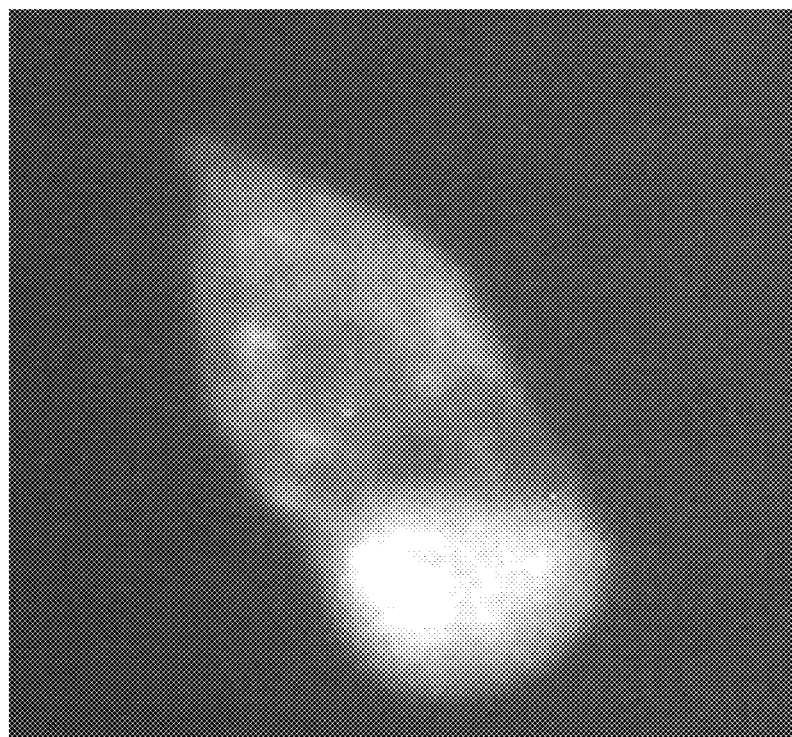

As seen in FIGS. 10A-10B, immunofluorescence images of BDF's on smooth implants revealed diffuse and non-specific staining of vinculin in focal adhesions. The focal adhesions are poorly formed and can't be clearly demarcated. The cells have aggregated on the surface of the smooth implant and have preferentially bound to each other (through cadherins) instead of forming focal adhesions with the implant beneath. The cells and aggregates have a round morphology, typical of poor cell attachment. Aggregated cells can exhibit a stressed cell phenotype. These images reveal that BDF's on smooth implant surfaces have attached poorly, and subsequently are unable to spread and are therefore unable to develop typical fibroblast morphology.

Comparative Example: BDF's on Mentor Siltex Textured Implants (in the Initial Coloured Images: Red=F-Actin, Green=Vinculin and Blue=Dapi)

Figure 11:
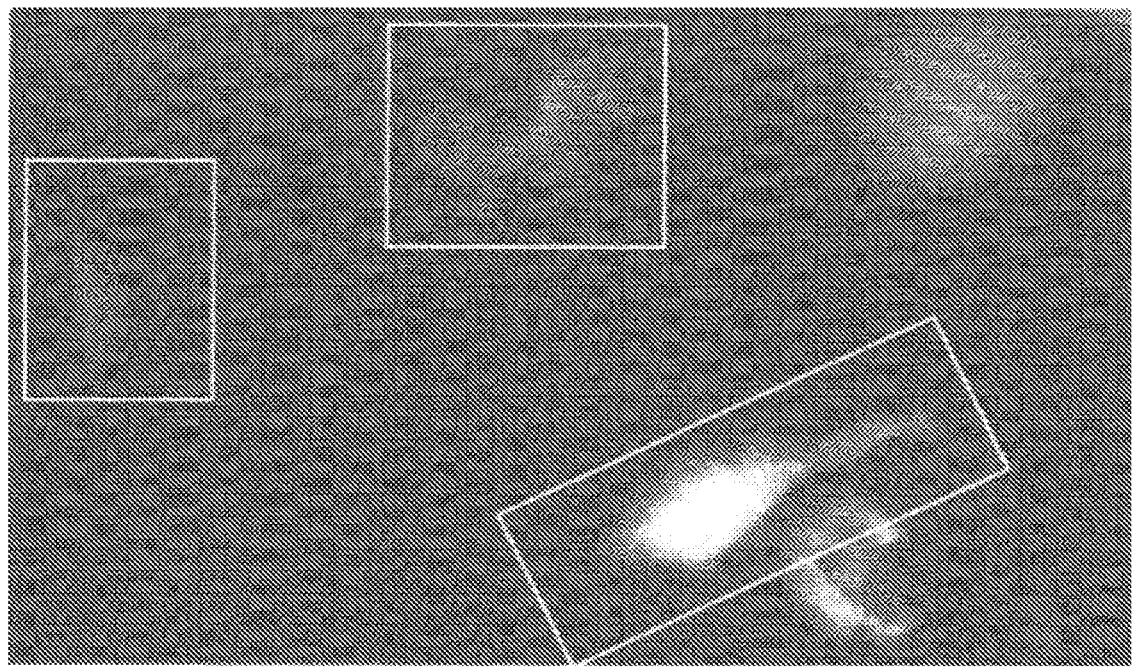
FIG. 11 depicts immunofluorescence cell morphology and phenotype data for BDF's grown on comparative textured implants (Mentor Siltex). The images show staining of F-Actin (red in original colour images), vinculin (green in original colour images) and Dapi (blue in original colour images). White boxes highlight vinculin staining and focal adhesion formation.

As seen in FIG. 11, immunofluorescence images of BDF's on textured implants again revealed mostly diffuse and non-specific staining of vinculin in focal adhesions. However, some focal adhesions can be clearly demarcated indicating some stable focal adhesion formation (identified by white rectangles in FIG. 11). The cells have been able to spread to an extent, however, as shown in the FIG. 11 image, it appears that the cells are wedged within the valleys between the steep nodules on the textured implant surface. They are therefore unable to spread, migrate or proliferative effectively and are restricted by the steep sidewalls. It is reasonable to expect that the up to 9 cells observed to be wedged within the bottom of the valleys will experience "contact inhibition". This may lead to a stressed cell phenotype. These images reveal that BDF's on textured implant surfaces have become wedged within the bottom of valleys between implant nodules, and although show some signs of focal adhesion formation and cell spreading they are restricted and inhibited from spreading and proliferating optimally.

Comparative Example: BDF's on Tissue Culture Plastic (in the Initial Coloured Images: Red=F-Actin, Green=Vinculin and Blue=Dapi). White Circles Indicate Vinculin Staining within Focal Adhesions.

Figure 12:
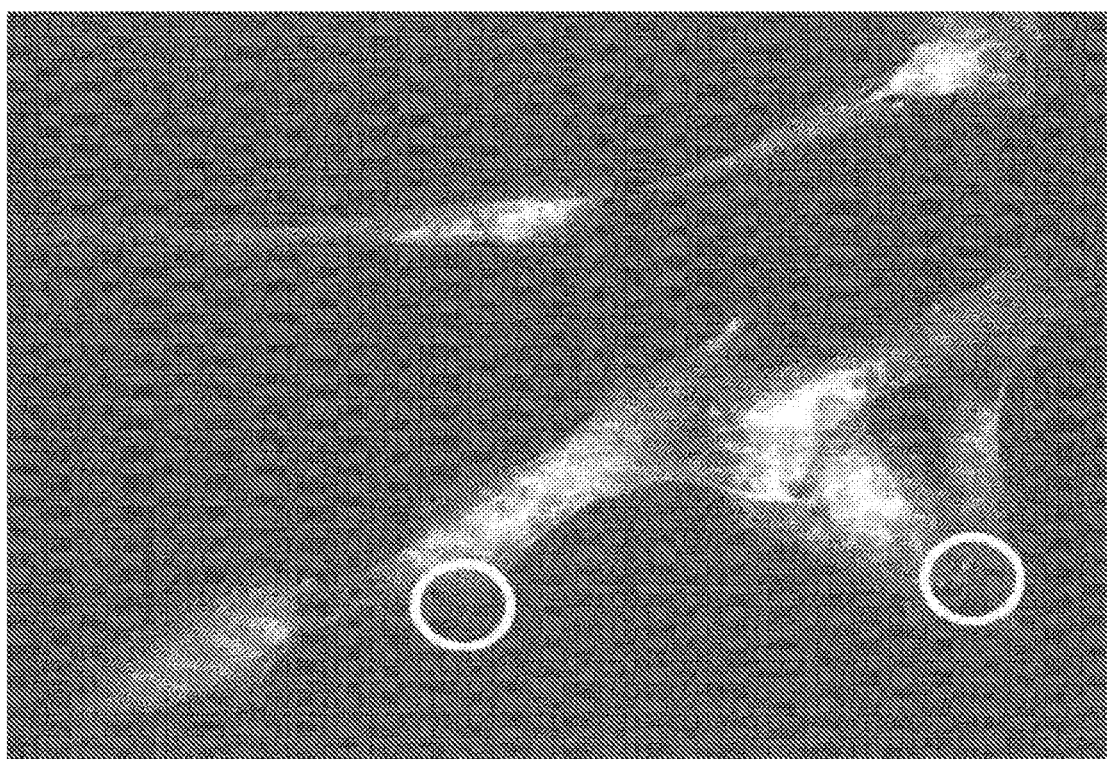
FIG. 12 depicts immunofluorescence cell morphology and phenotype data for BDF's grown on tissue culture plastic (TCP). The images show staining of F-Actin (red in original colour images), vinculin (green in original colour images) and Dapi (blue in original colour images). White circles highlight vinculin staining and focal adhesion formation.

As shown in FIG. 12, BDF's cultured on TCP show typical fibroblast phenotype in vitro. Strong staining for vinculin within local adhesions is present, which is abundant and clearly defined (identified by white circles). This indicates strong focal adhesion formation and allows the cell to spread effectively. Significant cell attachment and proliferation can be observed by number of cells present.

Comparative Example: BDF's on Collagen (in the Initial Coloured Images: Red=F-Actin, Green=Vinculin and Blue=Dapi)

Figure 13A:
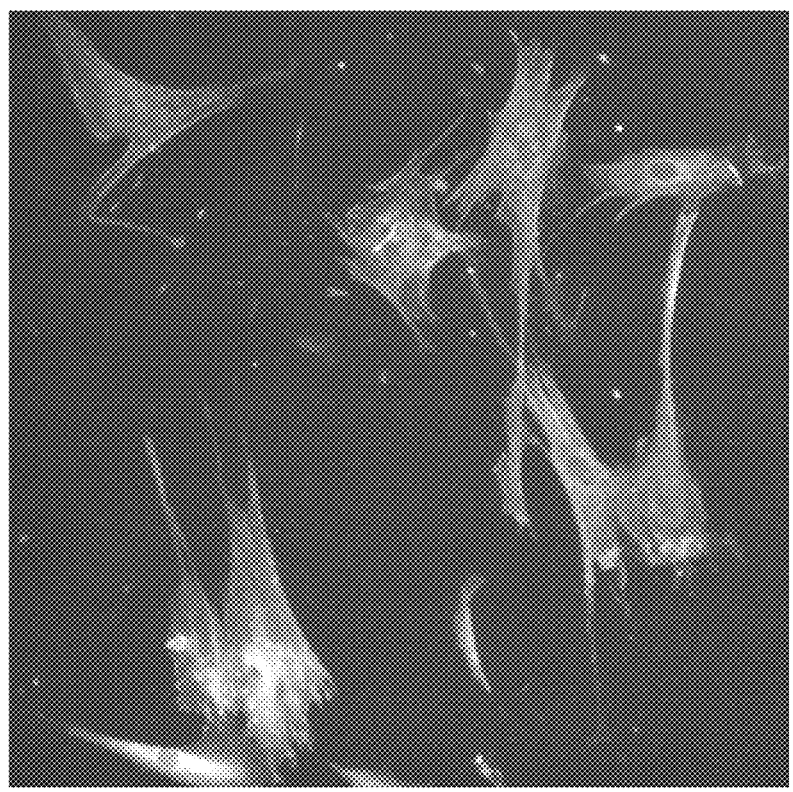
FIGS. 13A-13B depict immunofluorescence cell morphology and phenotype data for BDF's grown on collagen. The images show staining of F-Actin (red in original colour images), vinculin (green in original colour images) Dapi (blue in original colour images). White circles highlight vinculin staining and focal adhesion formation.
Figure 13B:
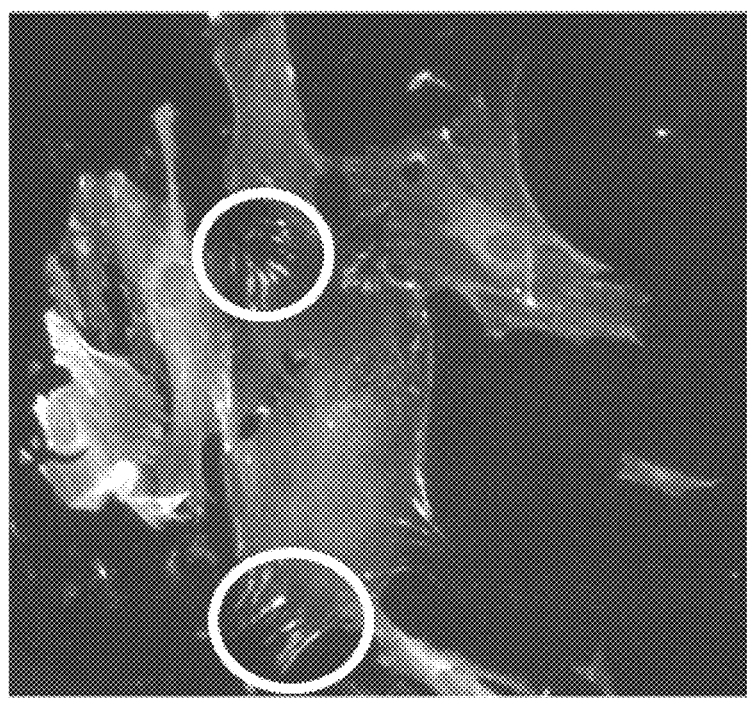

As shown in FIGS. 13A-13B, BDF's cultured on collagen show typical fibroblast phenotype in vitro. Strong staining for vinculin within local adhesions is present, which is abundant and clearly defined (indicated by white circles). Staining for vinculin is even more prominent in cells on collagen than cells on TCP. This indicates strong focal adhesion formation and allows the cell to spread effectively. Cells have spread more widely on collagen than cells on TCP. The presence of collagen appears to have promoted significant cell attachment and cell spreading, even when compared to cells on TCP.

6) SEM—Cell Morphology

Example: BDF's on ADM BM C After 6 Hours.

Figure 14:
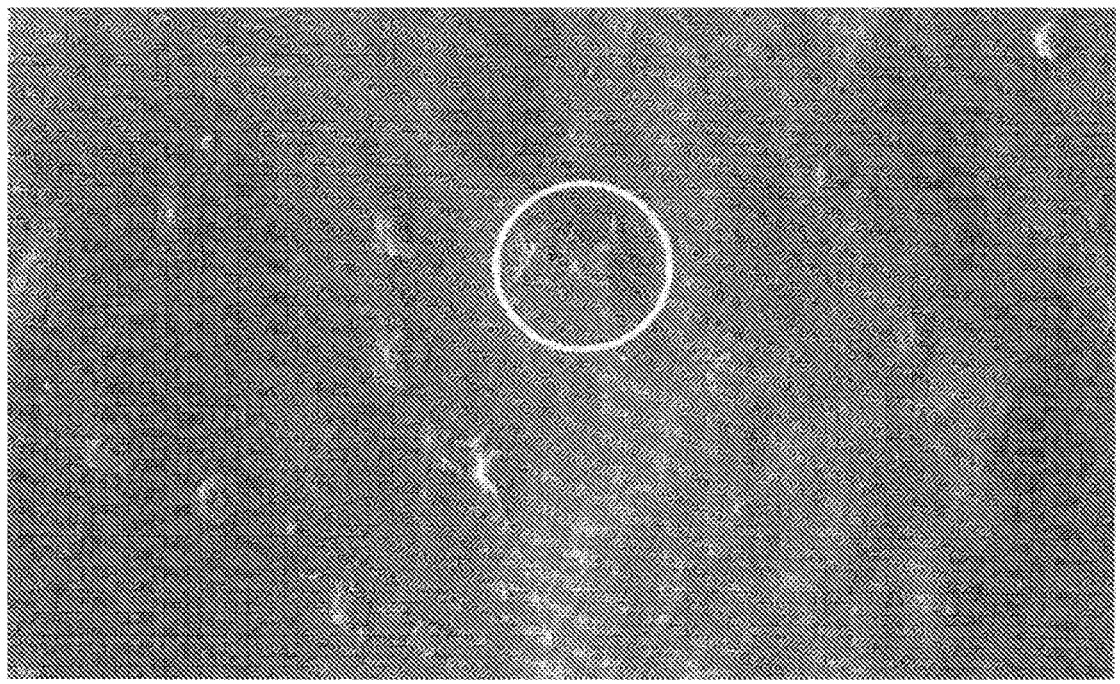
FIG. 14 depicts SEM image data showing BDF growth on ADM BM C implant surface according to the invention after 6 hours. BDF's have clearly attached and are beginning to spread on the surface (white circle indicates a BDF which is displaying typical fibroblast spread morphology).

As Seen in FIG. 14, after 6 hours BDF's on ADM BM C according to the invention have attached and are beginning to spread on the surface (white circle indicates a BDF which is displaying typical fibroblast spread morphology)

Figure 15:
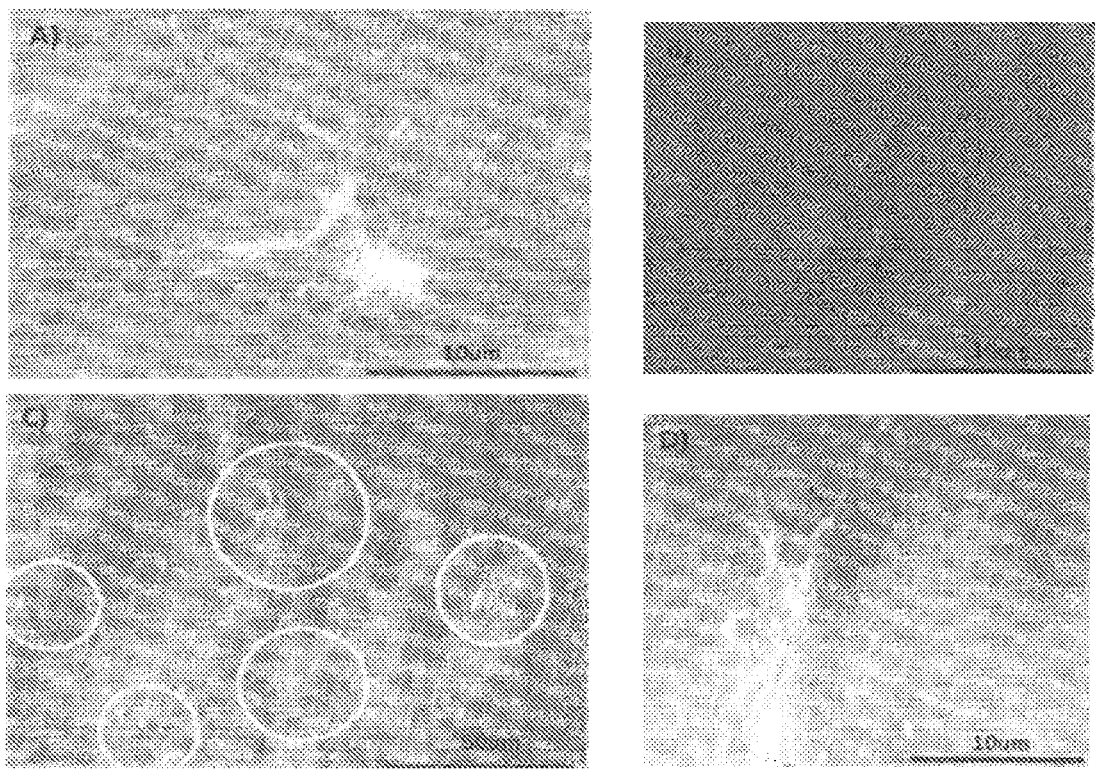
FIG. 15 depicts SEM images showing BDF growth on ADM BM C according to the invention after 24 hours (A) and 48 hours (B-D). It is clear to see the spread morphology of the cells on the ADM surface (white circle indicates a BDF which is displaying typical fibroblast spread morphology).
Figure 16A:
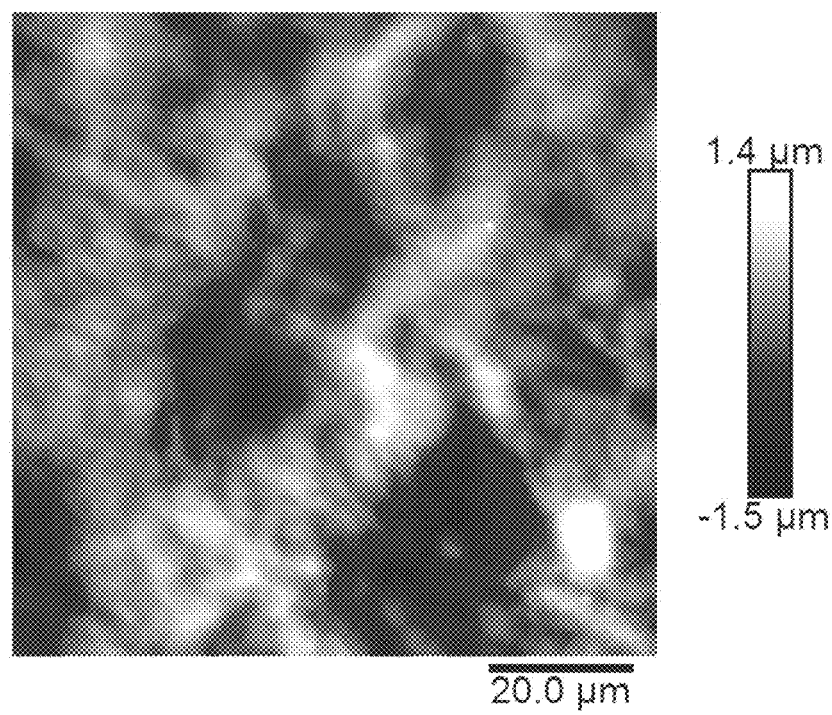
FIGS. 16A-16D depict Atomic Force Microscope (AFM) data for an image scan size of 90×90 um for ADM BM surface topography according to the invention.
Figure 16B:
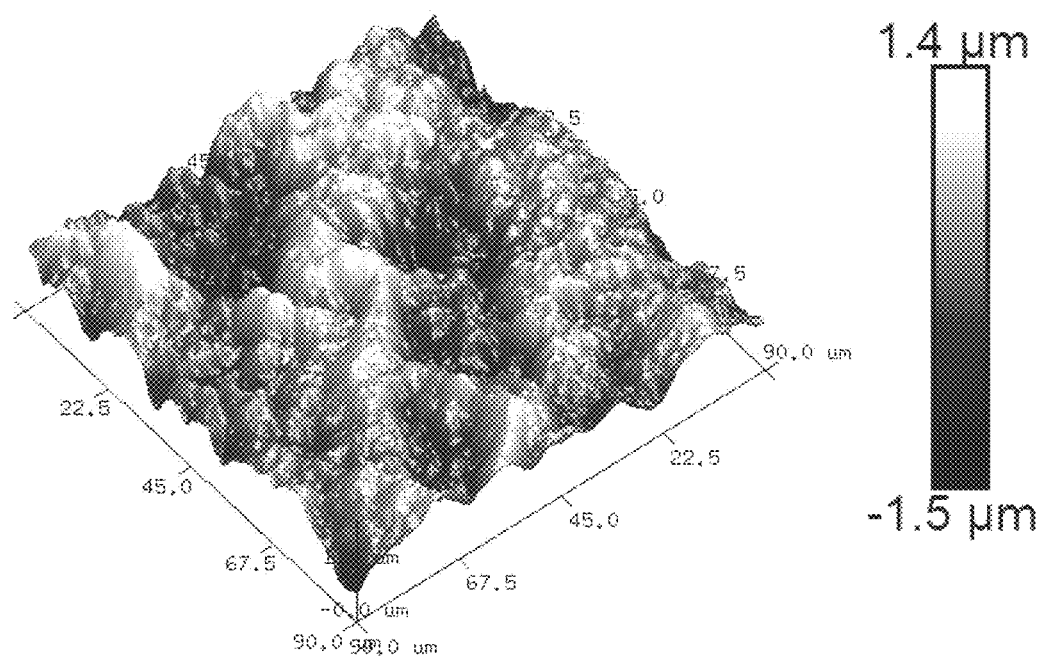
Figure 16C:
Figure 16D:
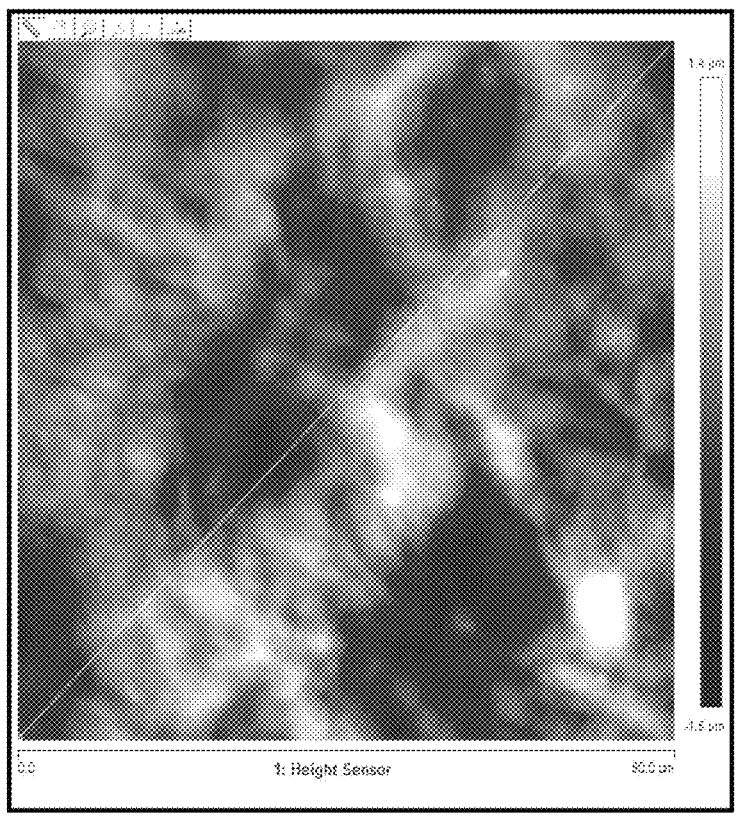
Figure 17A:
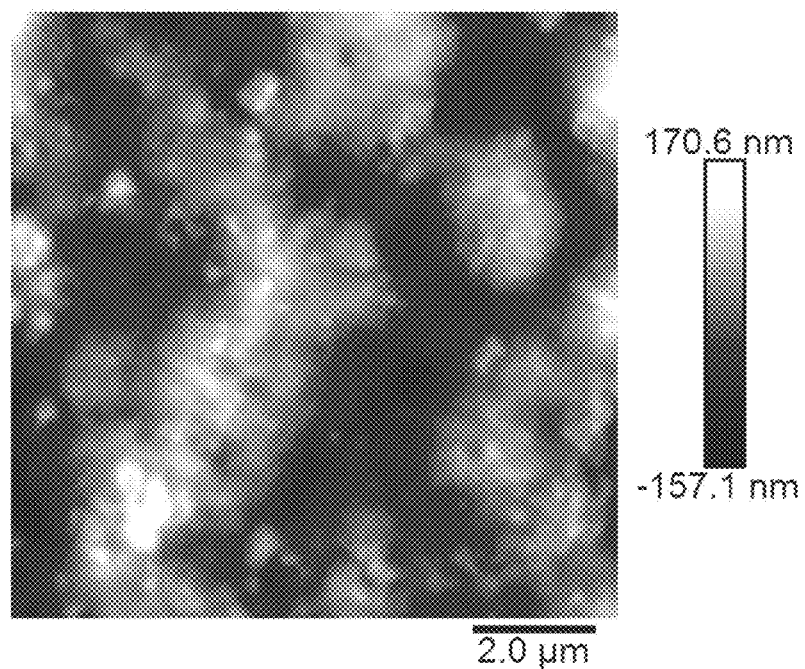
FIGS. 17A-17D depict Atomic Force Microscope (AFM) data for an image scan size of 10×10 um for ADM BM surface topography according to the invention.
Figure 17B:
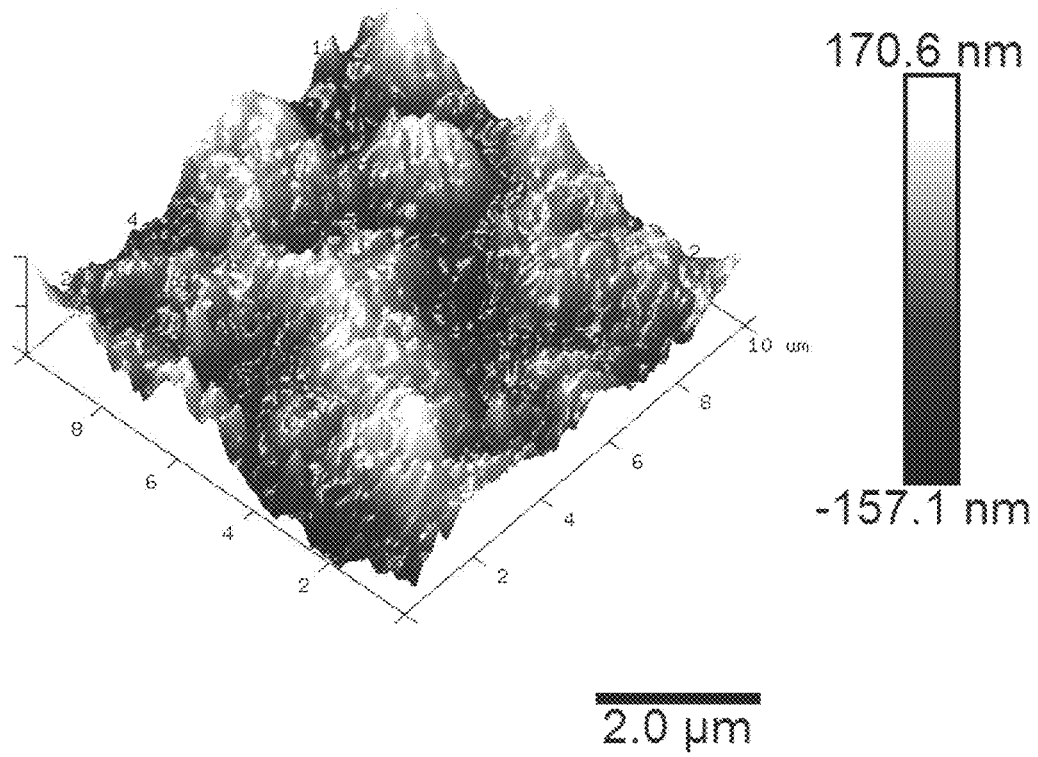
Figure 17C:
Figure 17D:
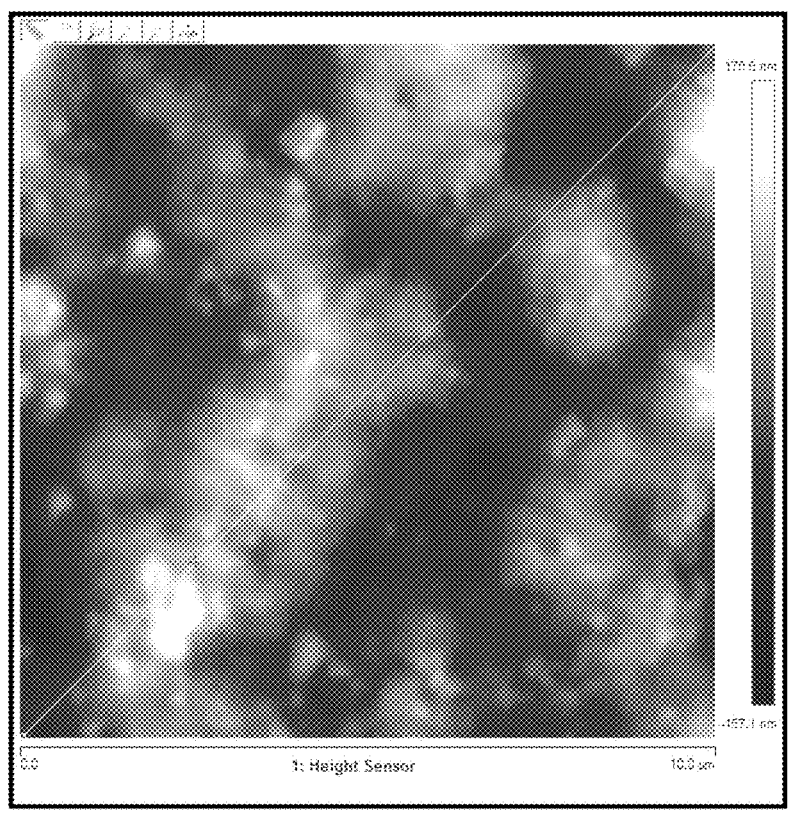
Figure 18A:
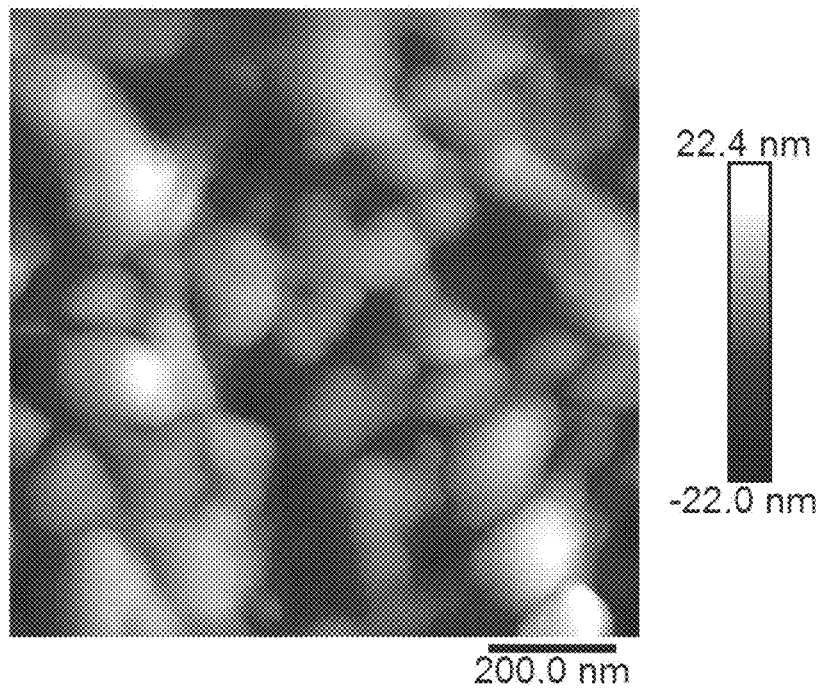
FIGS. 18A-18D depict Atomic Force Microscope (AFM) data for an image scan size of 1×1 um for an ADM BM surface topography according to the invention.
Figure 18B:
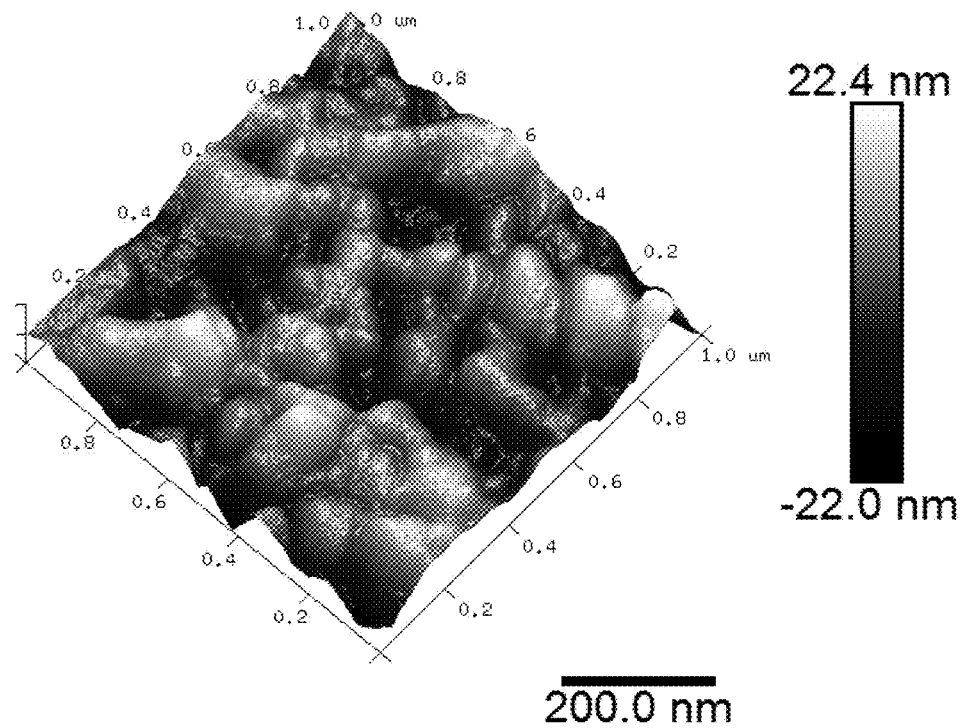
Figure 18C:
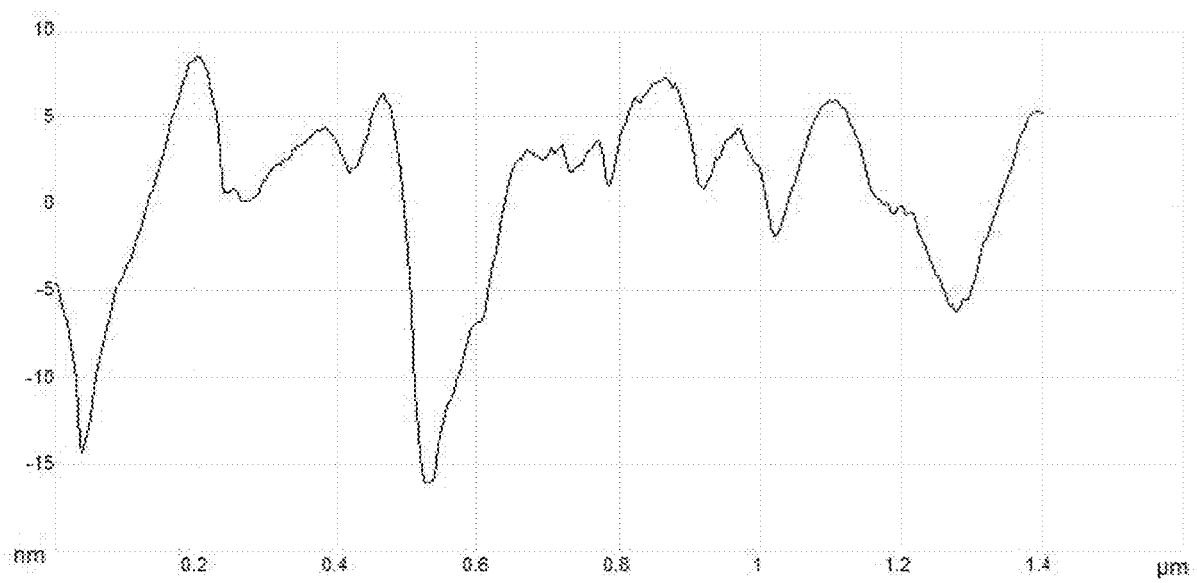
Figure 18D:
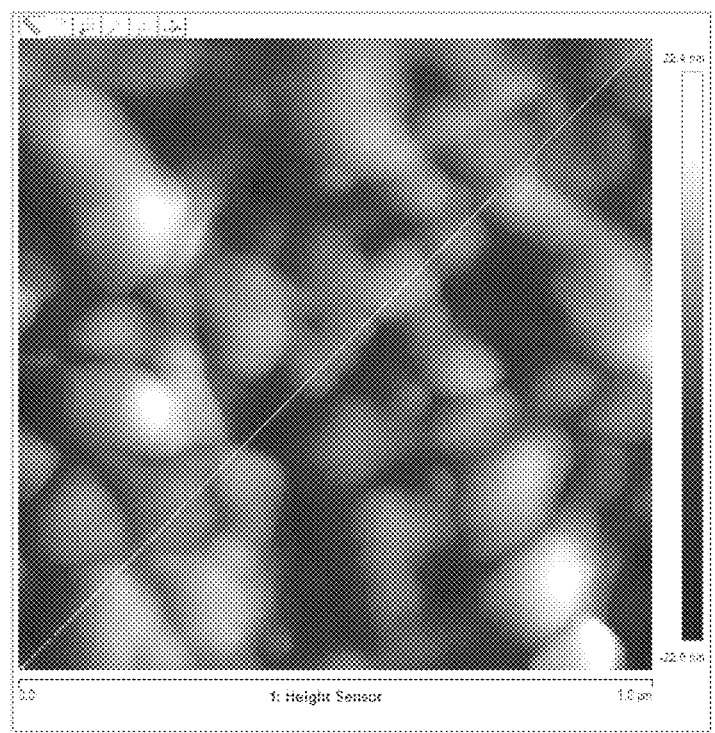
Figure 19A:
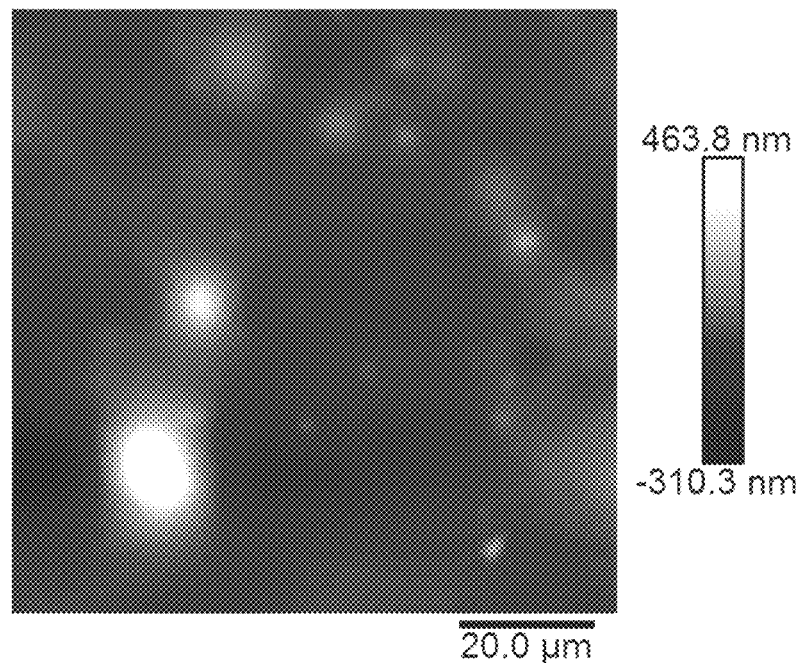
FIGS. 19A-19D depict Atomic Force Microscope (AFM) data for an image scan size of 90×90 um for comparative smooth implant surface topography (Mentor Smooth).
Figure 19B:
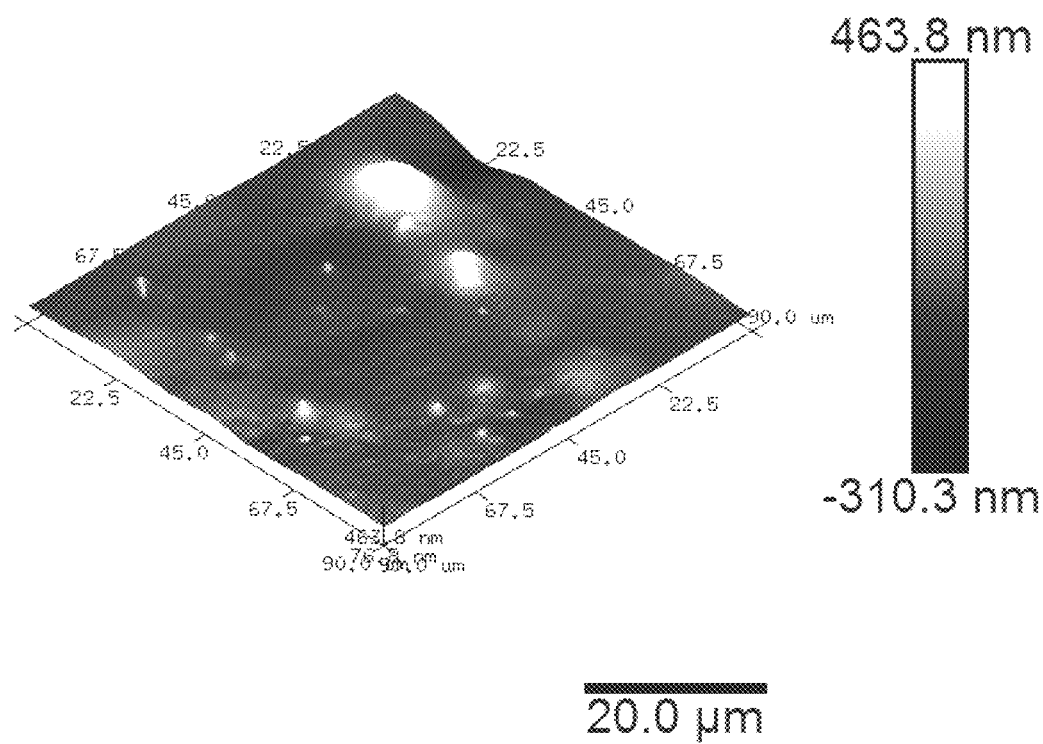
Figure 19C:
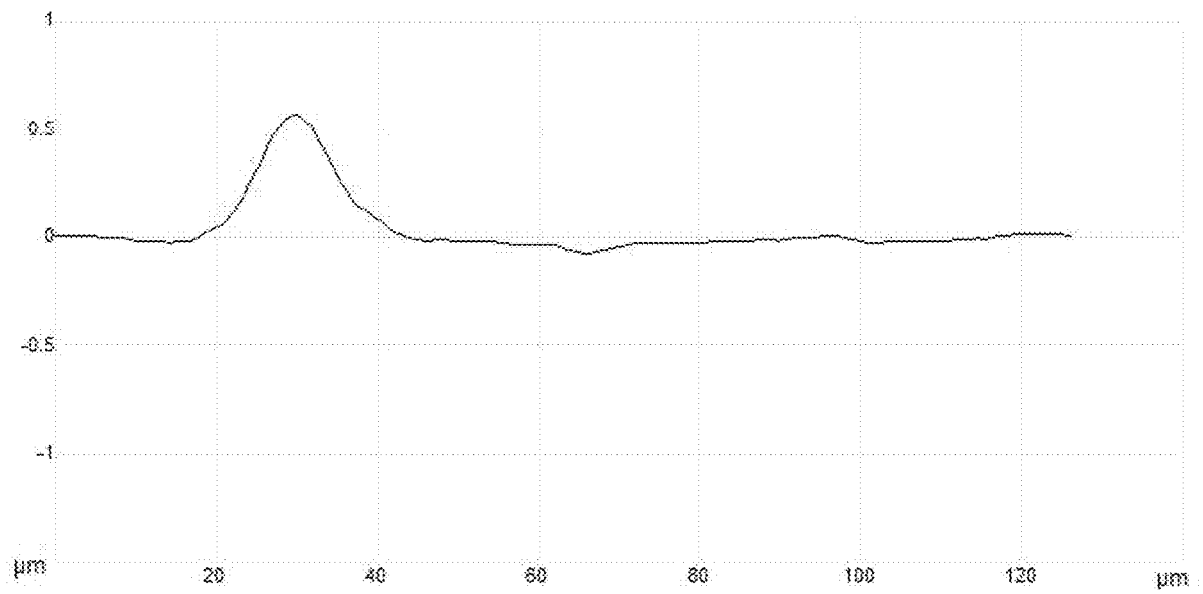
Figure 19D:
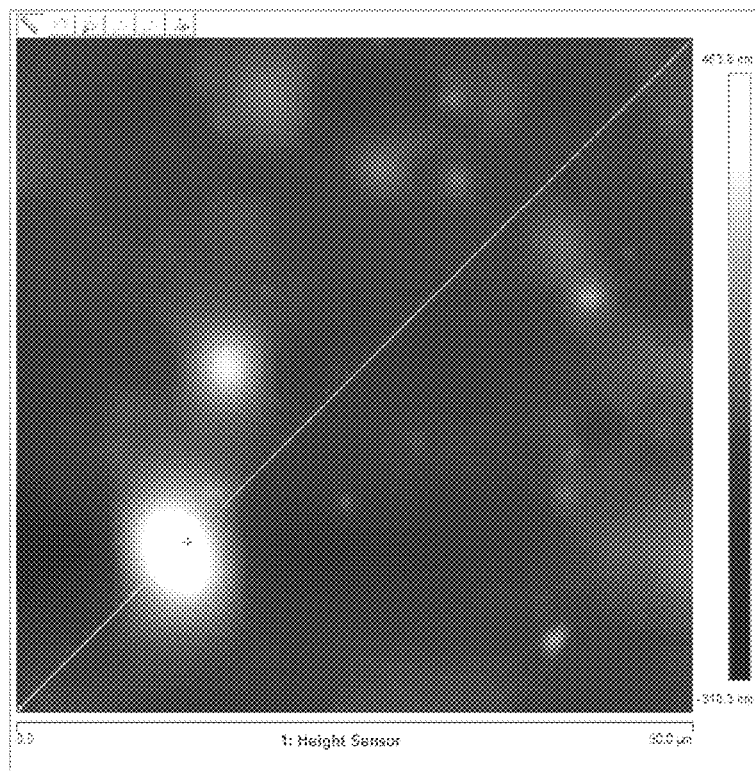
Figure 20A:
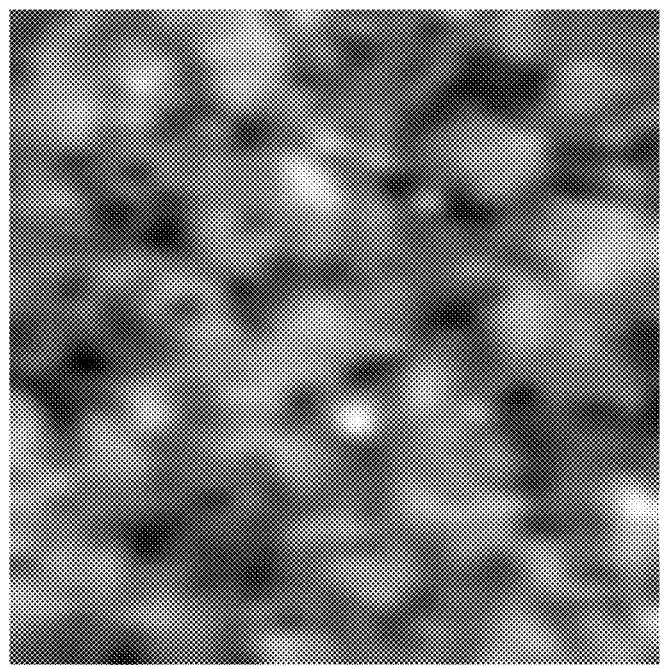
FIGS. 20A-20D depict 3D laser scanner data for an image scan size of 1 mm×1 mm for comparative textured implant surface topography (Mentor Siltex).
Figure 20B:
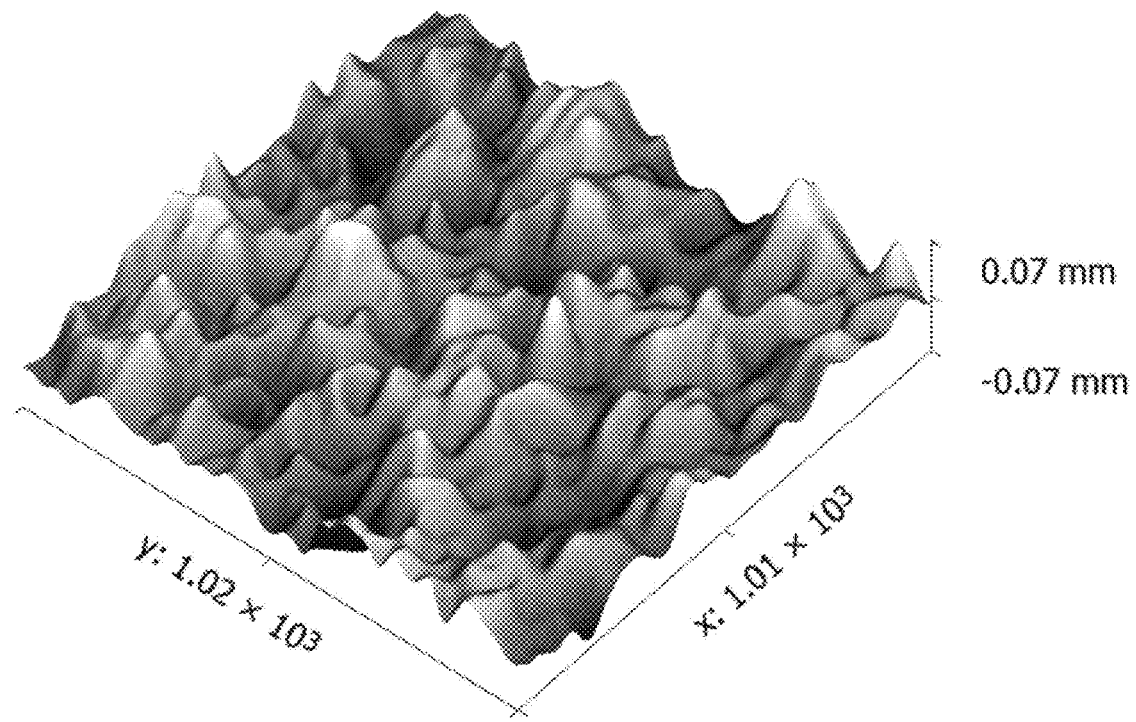
Figure 20C:
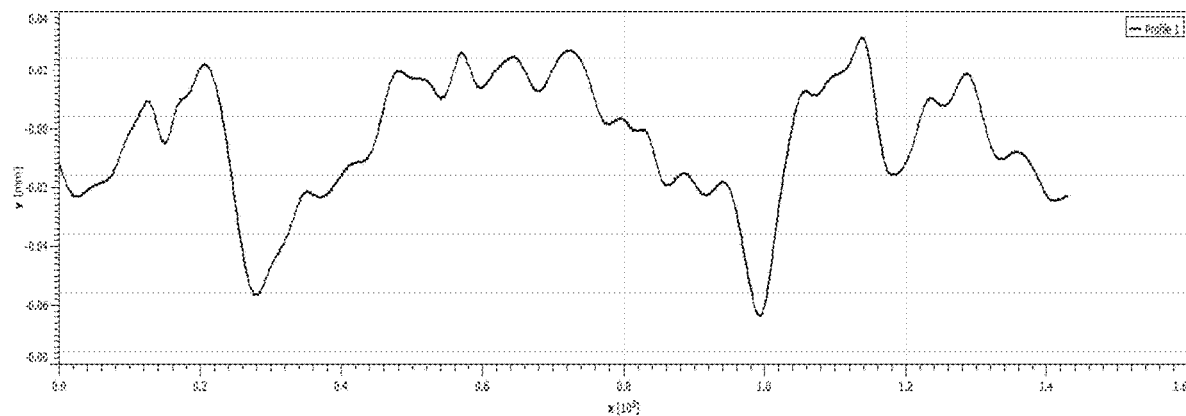
Figure 20D:
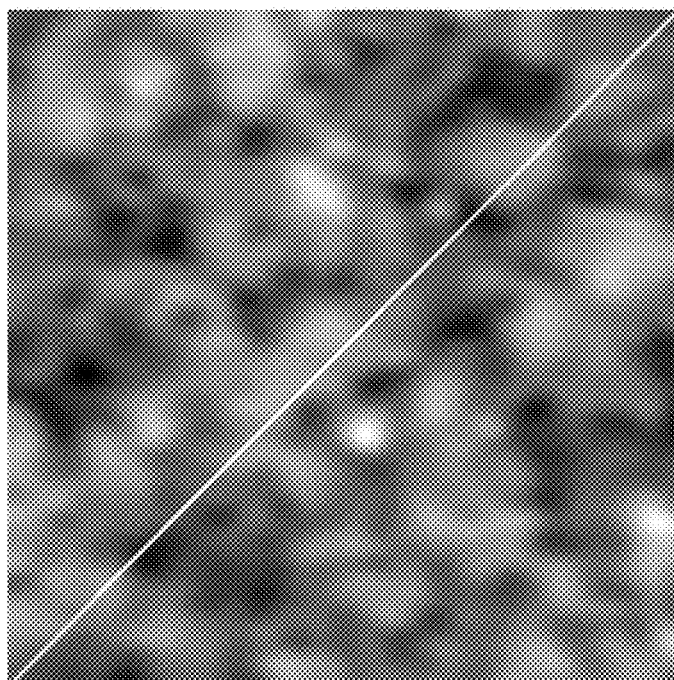
Figure 21A:
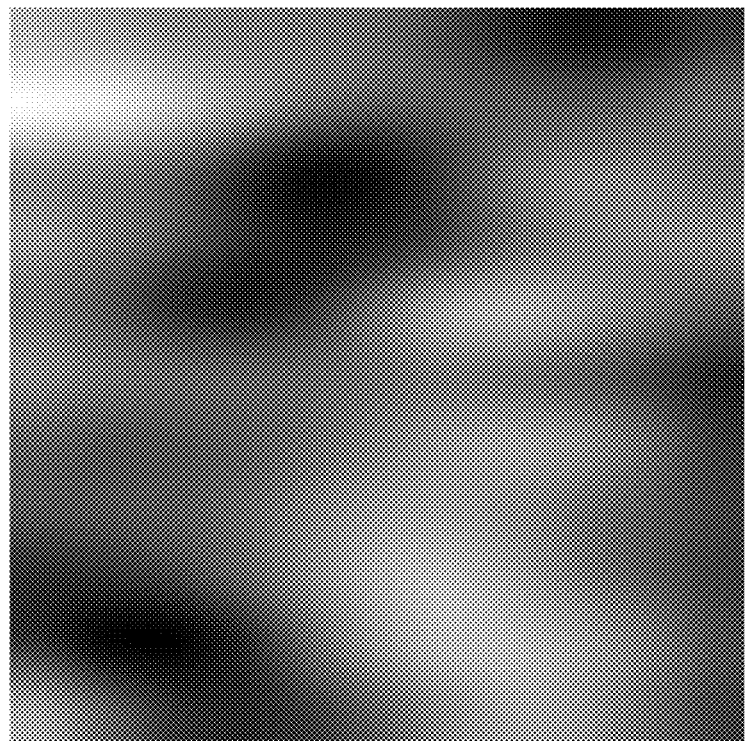
FIGS. 21A-21D depict 3D laser scanner data for an image scan size of 100 micron×100 micron for a comparative textured implant surface topography (Mentor Siltex).
Figure 21B:
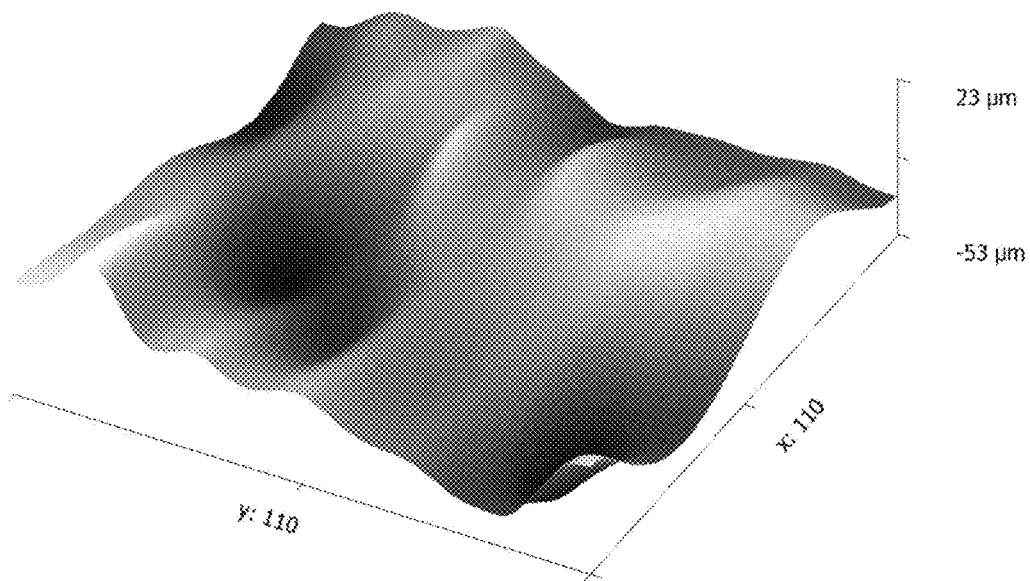
Figure 21C:
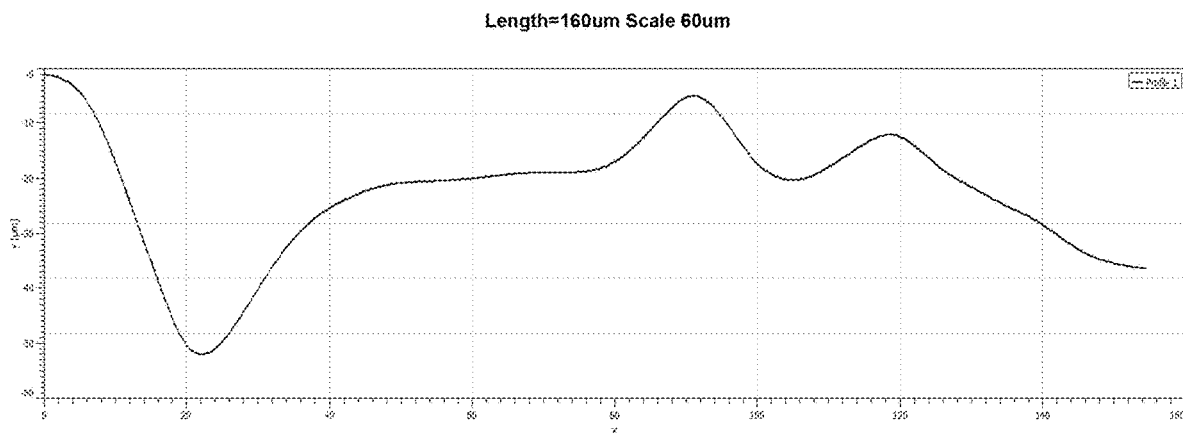
Figure 21D:
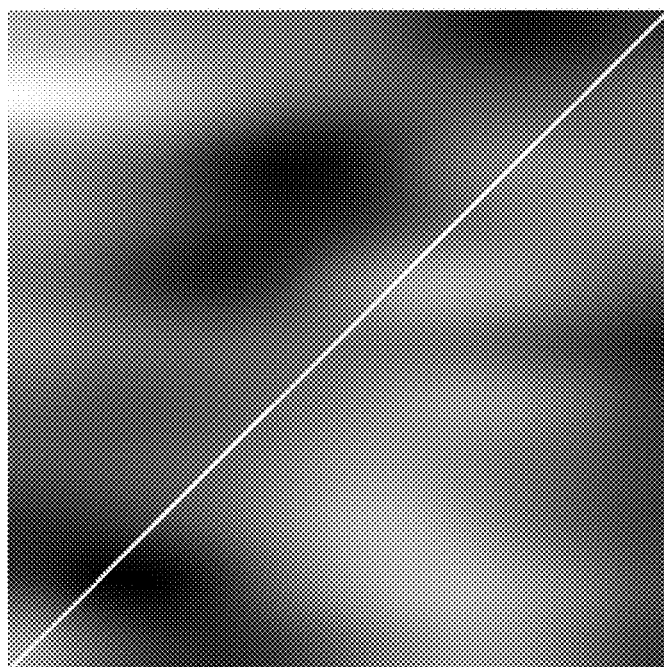
Figure 22A:
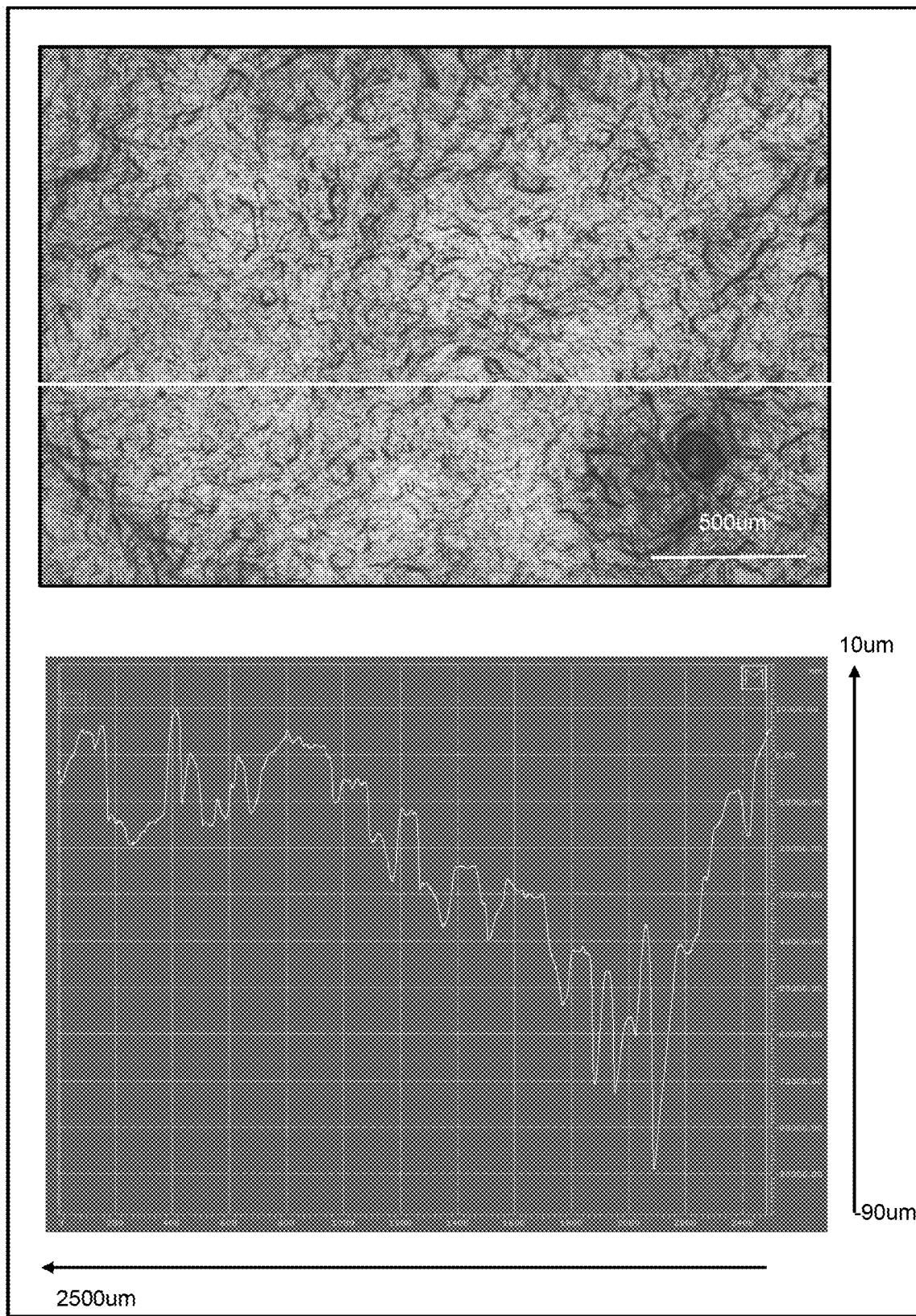
FIGS. 22A-22C depict Optical Microscopy images along with the corresponding 2D (vertical vs lateral) profile measured on a profilometer for ADM BM F surface topography fabricated according to the invention (FIG. 22A), comparative smooth implants (Mentor Smooth, FIG. 22B) and comparative textured (Mentor Siltex, FIG. 22C).
Figure 22B:
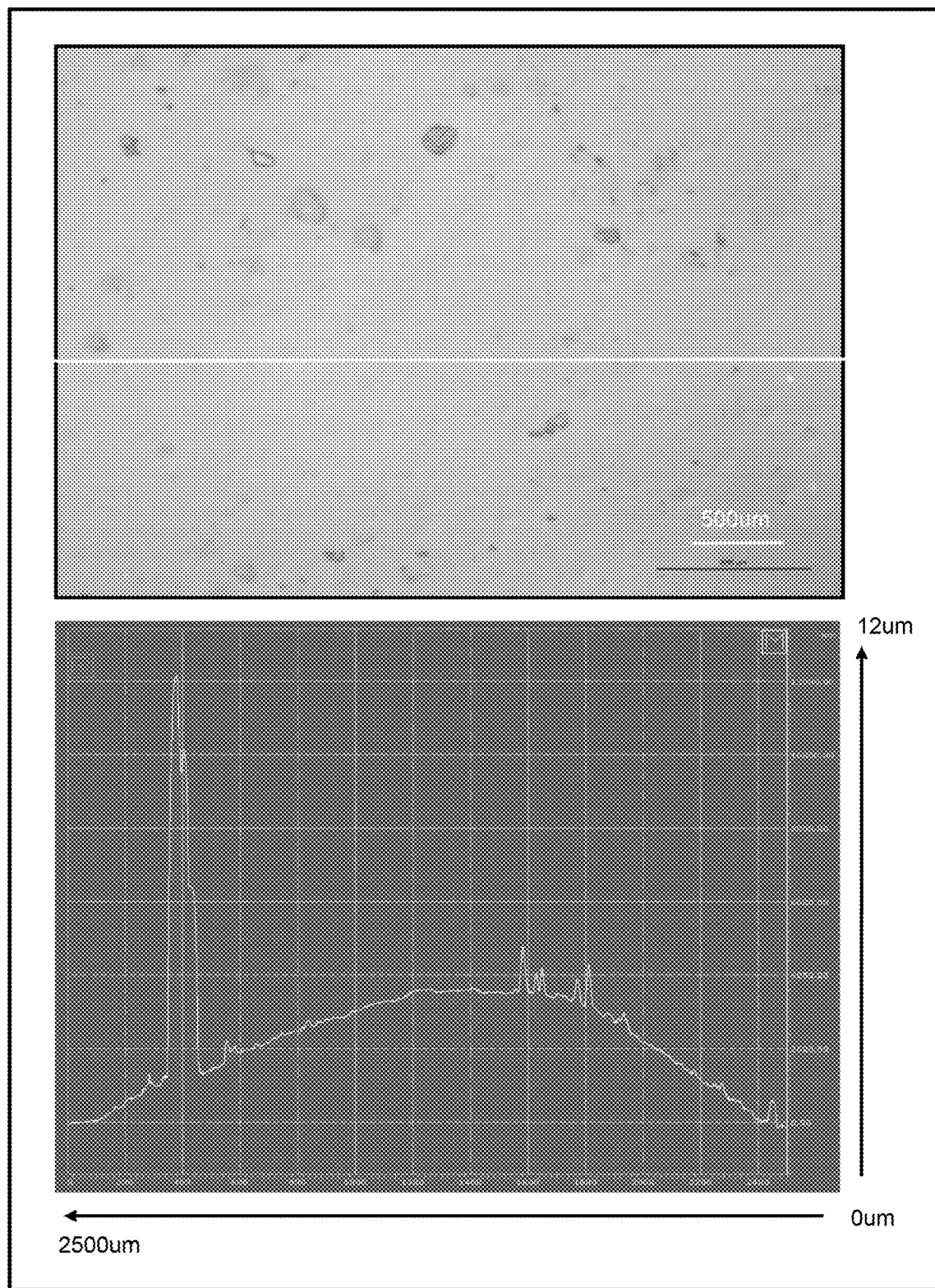
Figure 22C:
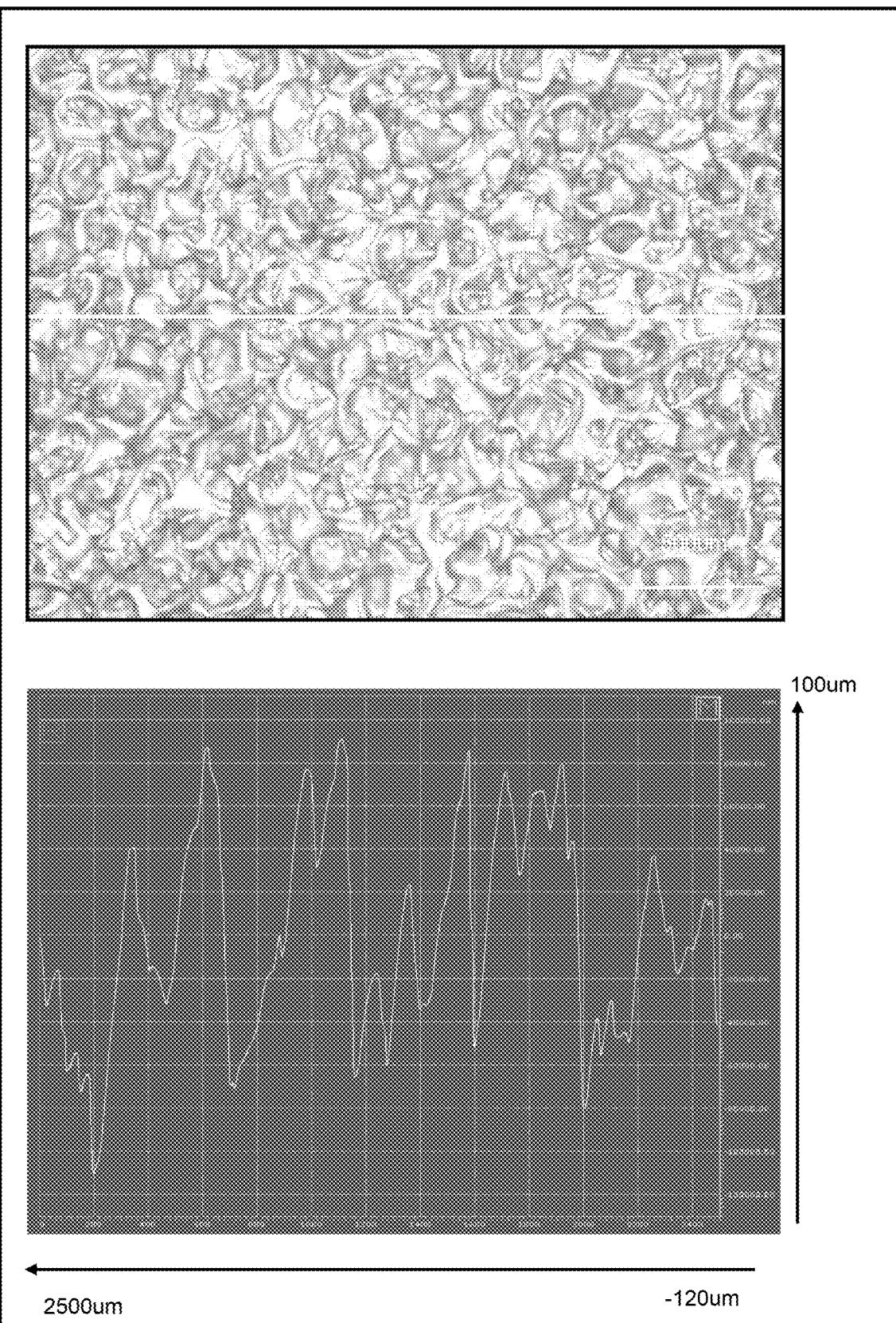
Figure 23A:
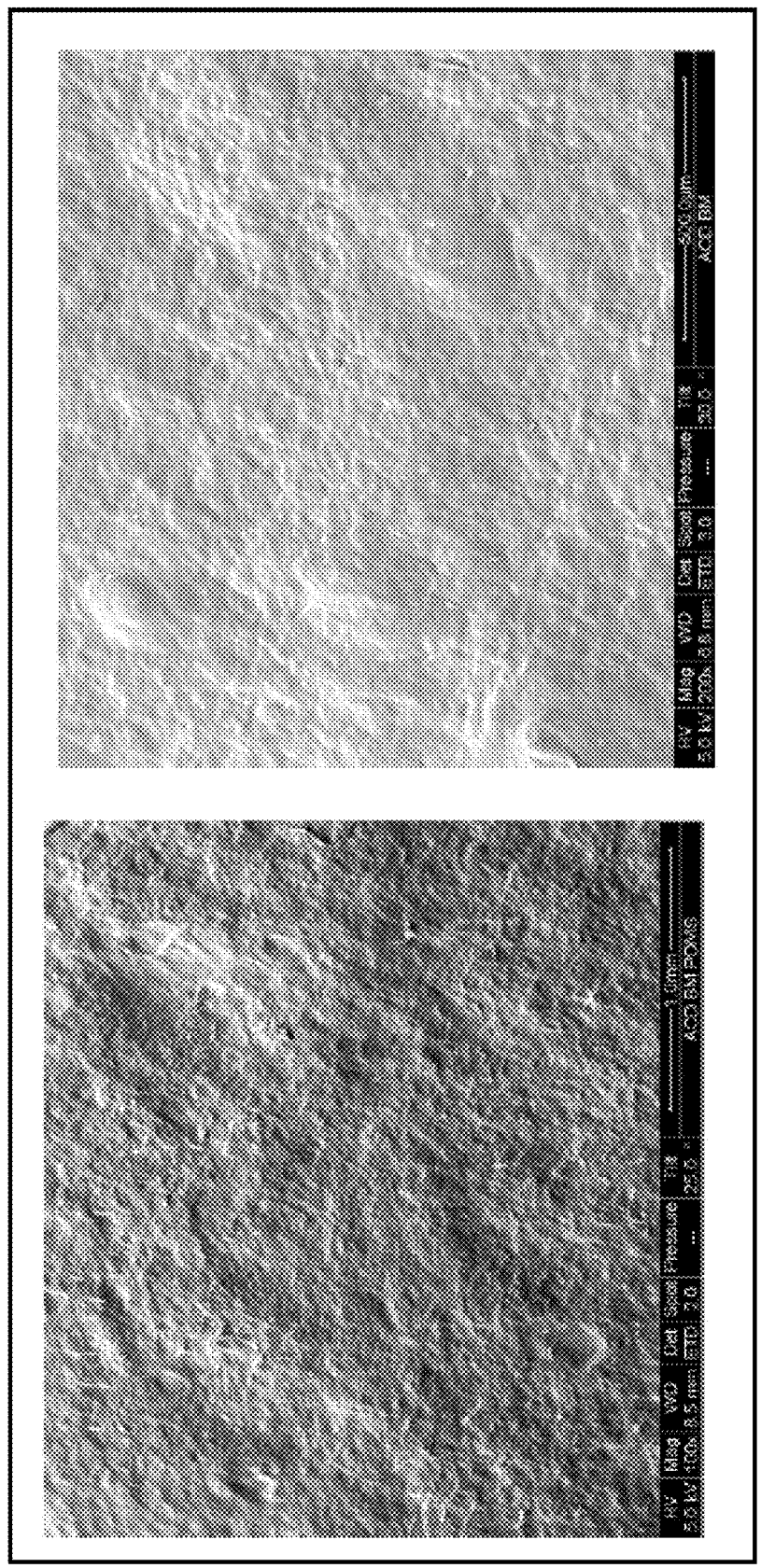
FIGS. 23A-23L depict SEM image data surface topographies at a variety of area scales for ADM BM according to the invention (FIG. 23A: 1 mm scale left, 500 μm scale right.
Figure 23B:
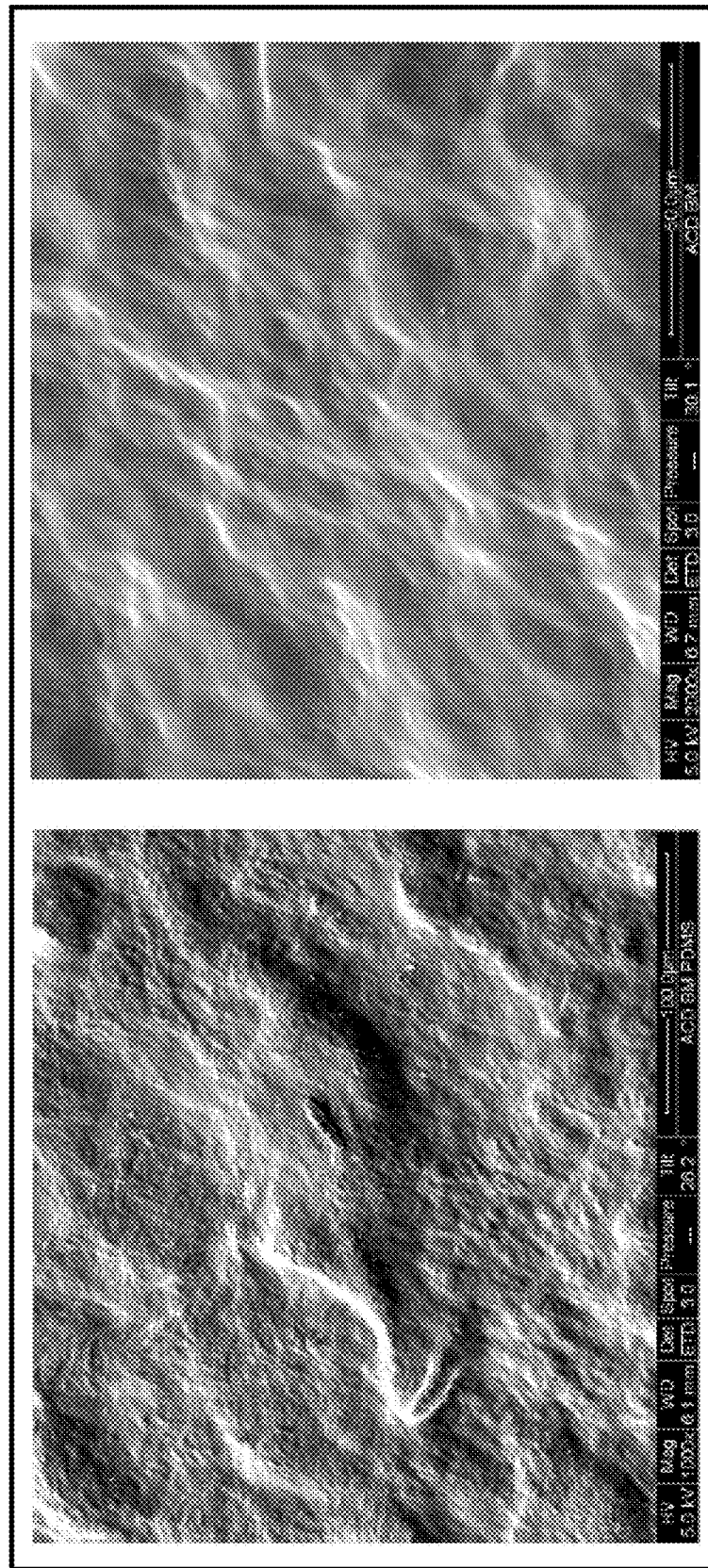
Figure 23C:
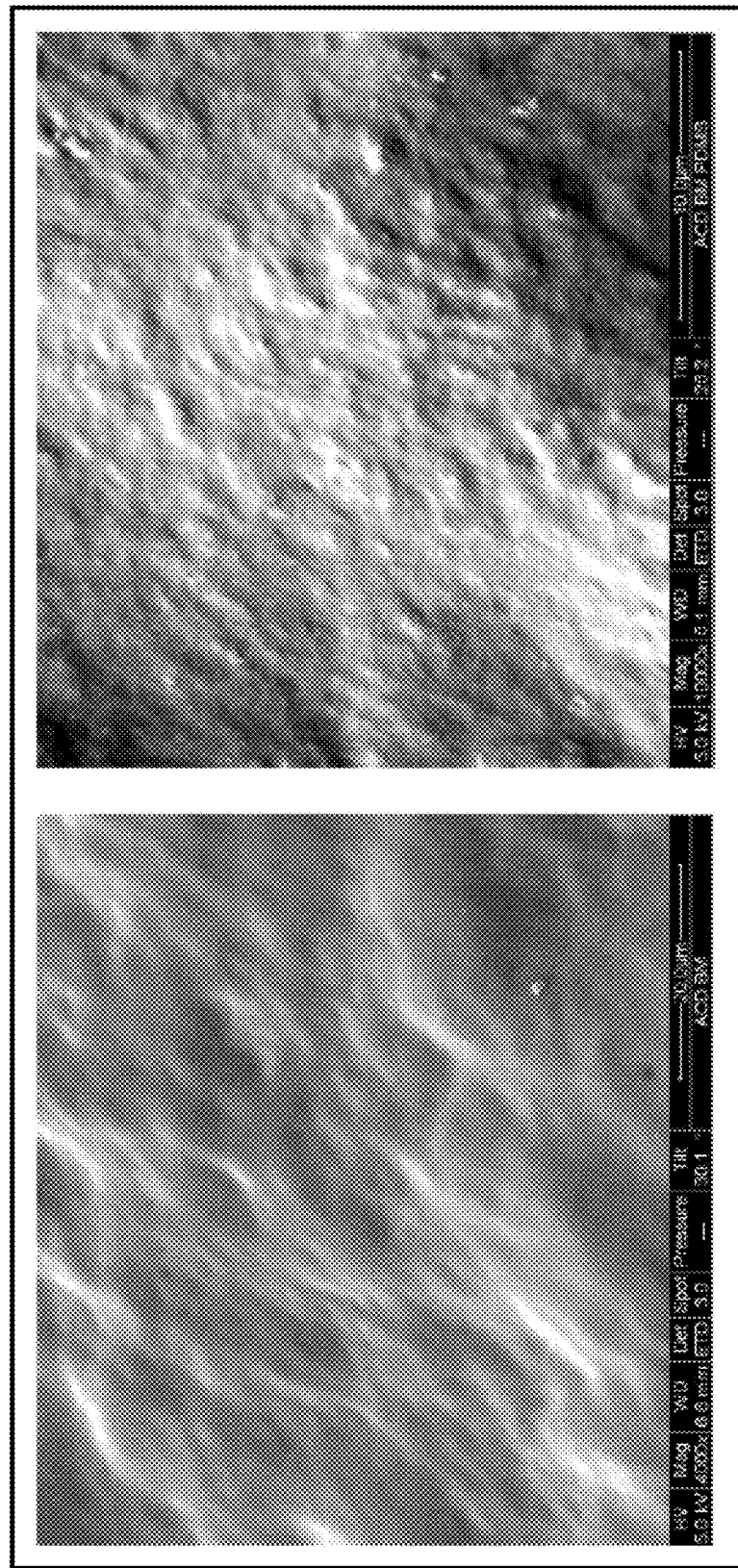
Figure 23D:
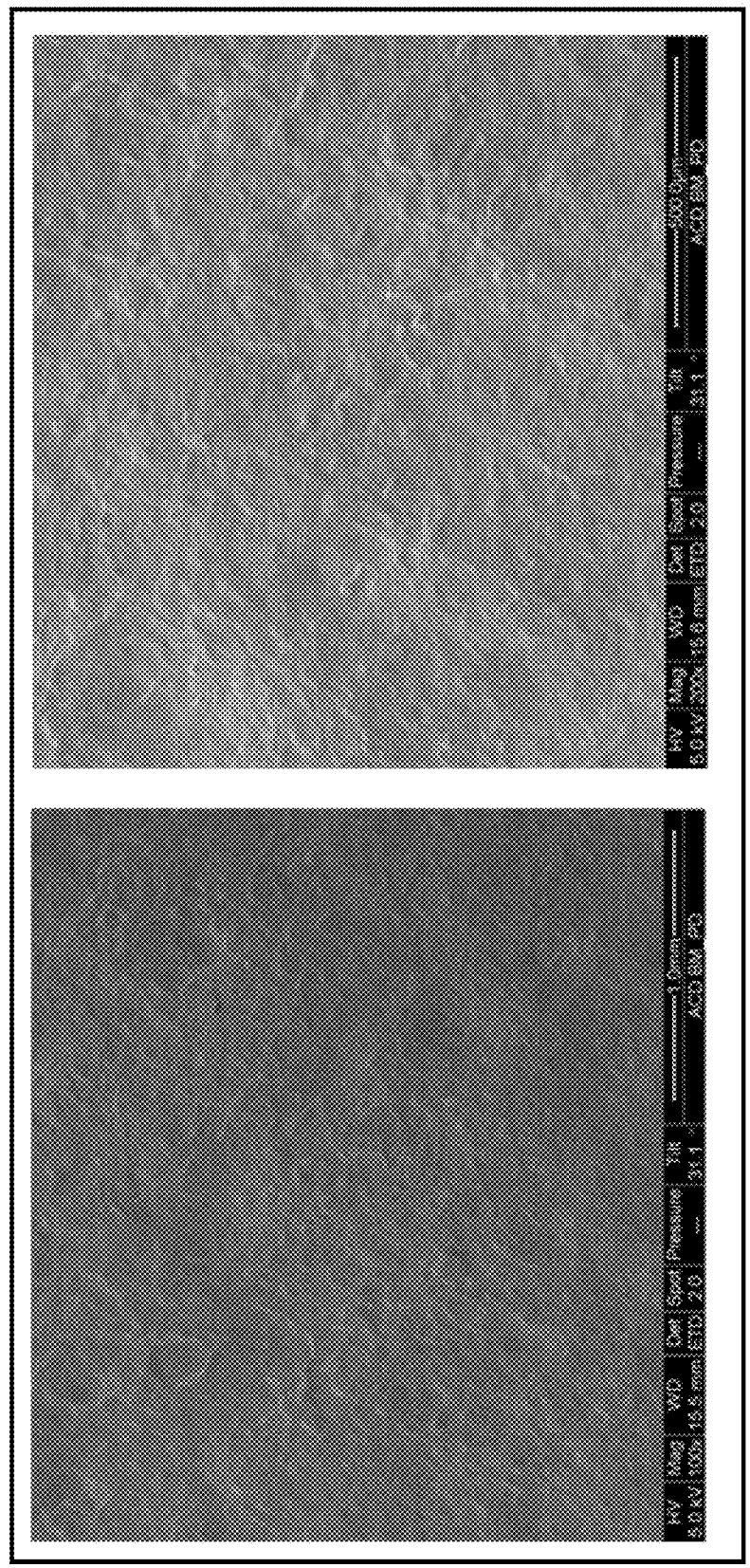
Figure 23E:
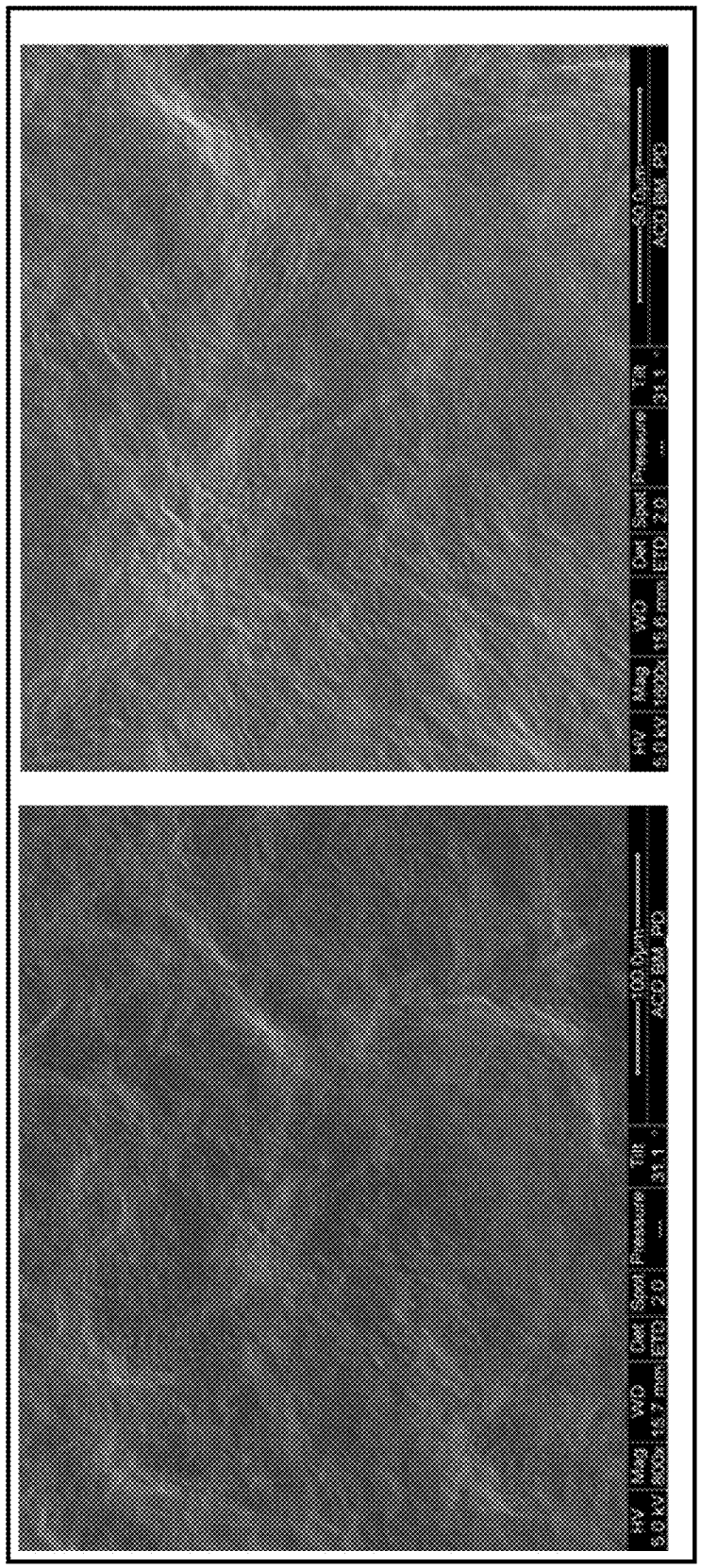
Figure 23F:
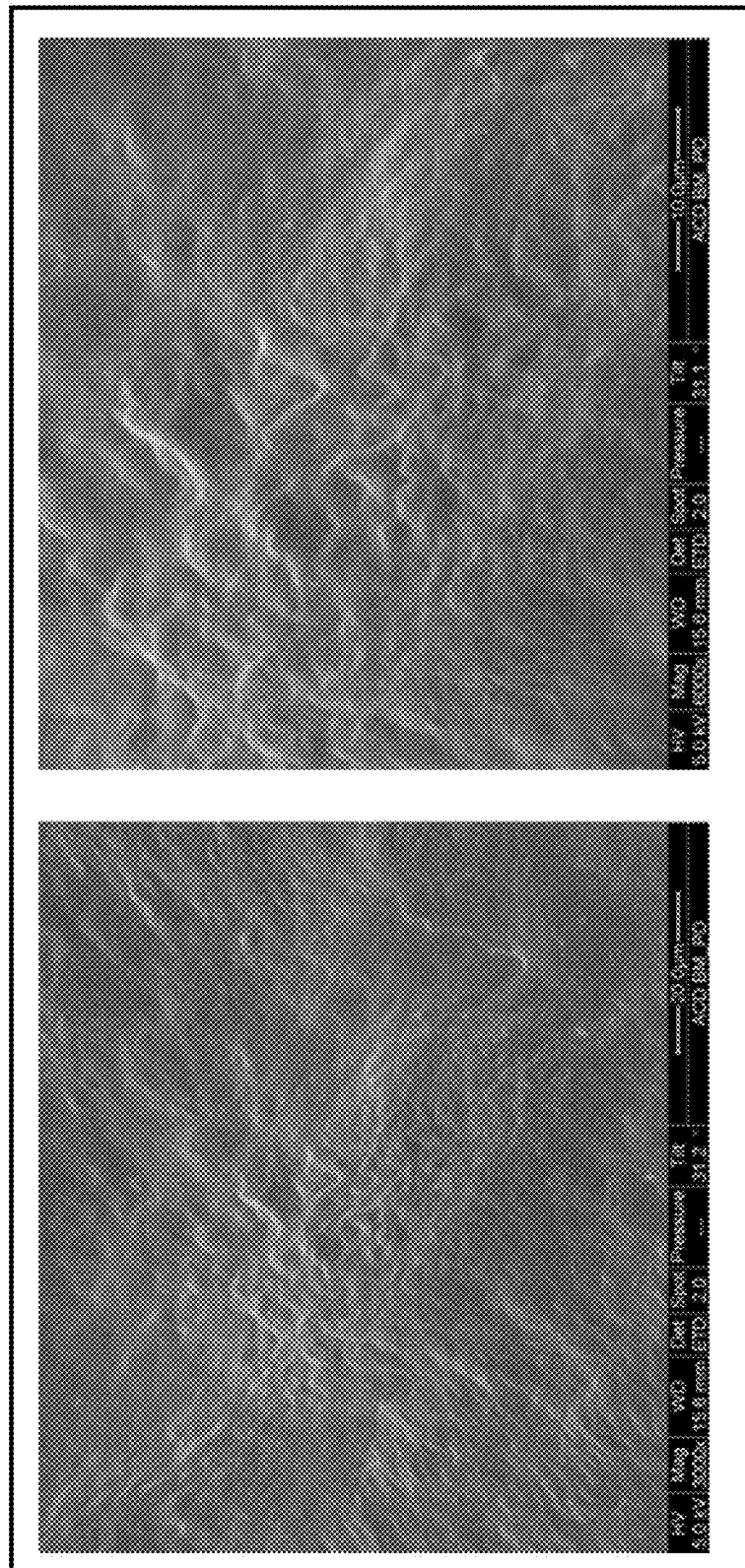
Figure 23G:
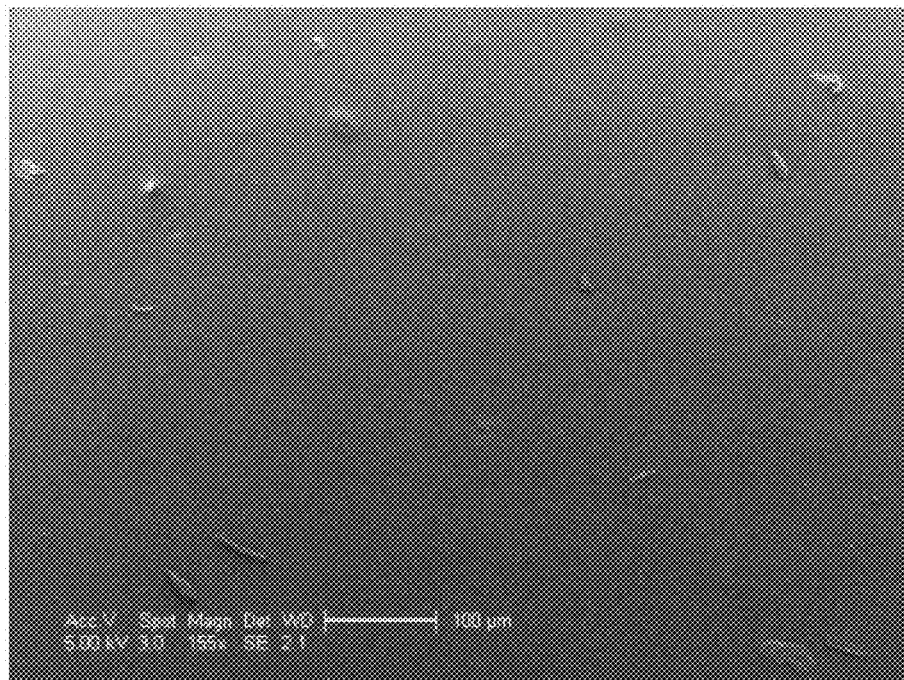
Figure 23H:
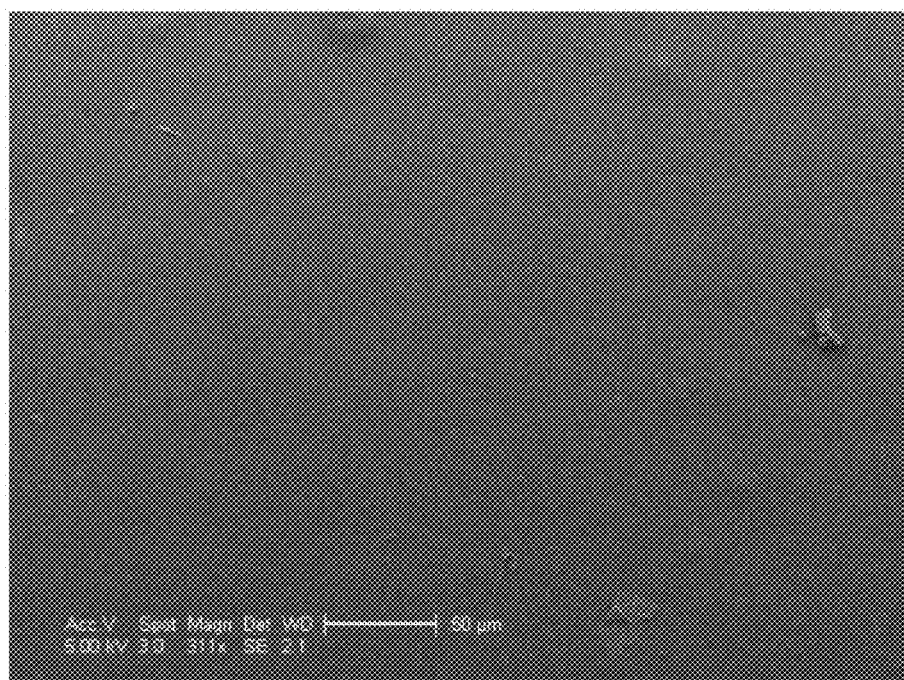
Figure 23I:
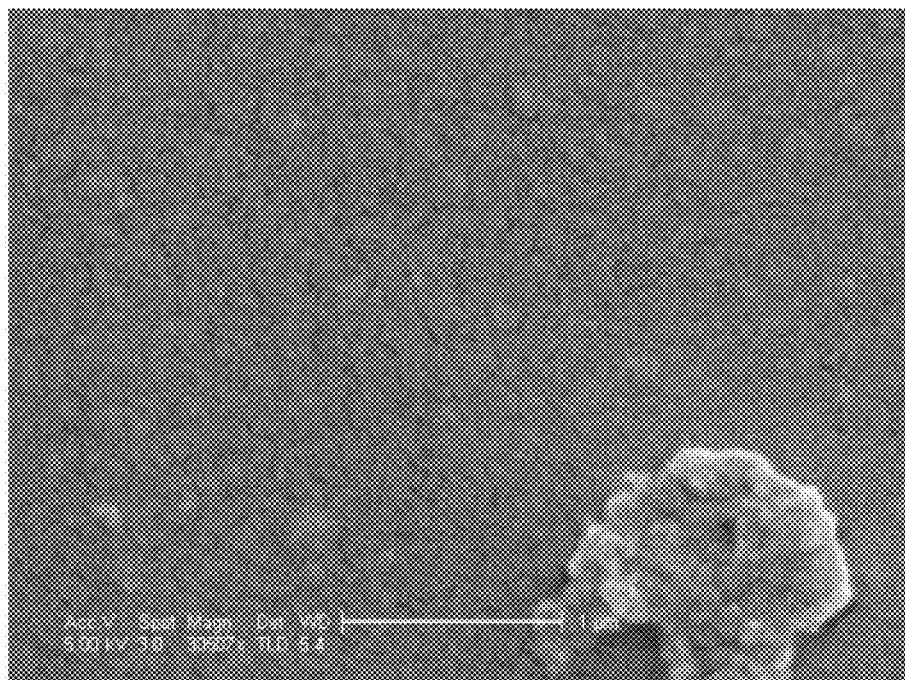
Figure 23J:
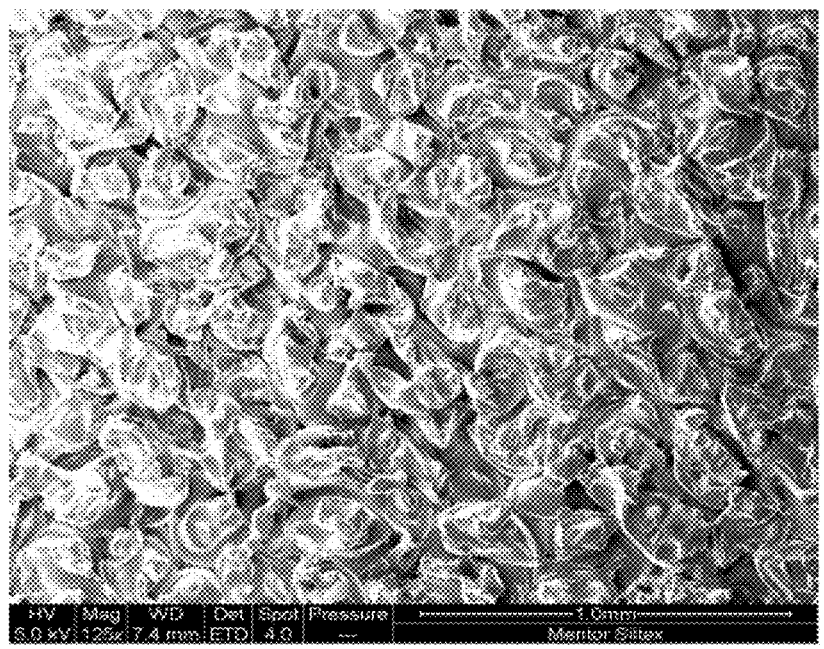
Figure 23K:
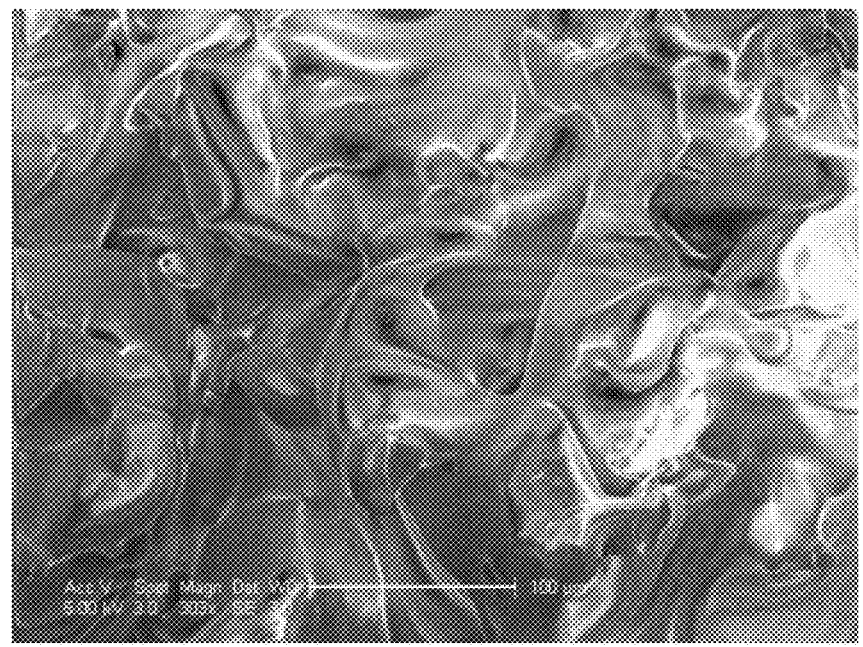
Figure 23L:
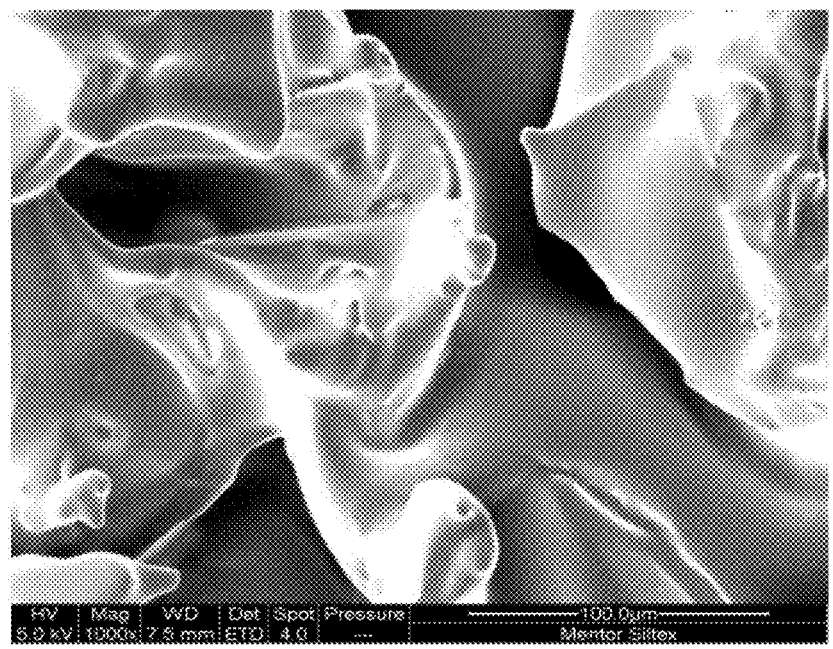

FIG. 15 shows Scanning Electron Microscope (SEM) images of BDF's on an ADM BM surfaces according to the invention after 24 hrs (A) and 48 hours (B,C and D). It is clear to see the spread morphology of the cells on the ADM surface (white circles indicate BDF's which are displaying typical fibroblast spread morphology).

Discussion

ADM BM surface has been comprehensively characterized using a variety of imaging and measuring instruments. Commercially available smooth (Mentor Smooth) and textured (Mentor Textured) implants have also been characterized using the same methods, and have been compared to ADM BM. Extensive quantitative and qualitative data on all surfaces has been gathered, and a number of significant and striking differences between surfaces has been elicited.

Two novel silicone surfaces inspired by ADM BM topography were fabricated. These surfaces were biologically evaluated in vitro, comparing the effect of ADM BM biomimetic silicone surfaces of the invention in comparison to smooth and textured implants on BDF cell attachment, proliferation, survival and expression of a number genes associated with cell attachment and proliferation (Vinculin and PCNA), in addition to the acute inflammatory response (IL8 and TNF alpha).

Based on the above data, ADM BM surfaces according to the invention promoted increased BDF attachment after 6 hours in comparison to smooth and textured implants; increased BDF proliferation from 24 hours up to a week in comparison to smooth and textured implants; PCNA (A gene up-regulated in proliferating cells) was up-regulated in BDF's cultured on ADM BM surfaces according to the invention in comparison to smooth and textured implants, correlating well with the cell proliferation data above; QRT-PCR revealed gene expression of Vinculin (A protein which forms an integral part of the focal adhesion complex and provides a measurement of the number of cells attached to a surface and how well they have attached) was up-regulated in BDF's cultured on ADM BM surfaces according to the invention in comparison to smooth and textured implants; gene expression of IL8 (A chemokine which plays a key role in the acute inflammatory response) was down-regulated in cells cultured on ADM BM surfaces according to the invention in comparison to smooth and textured implants; gene expression of TNF-alpha (A chemokine which plays a key role in the acute inflammatory response) was down-regulated in cells cultured on ADM BM in comparison to smooth and textured implants; immunofluorescence imaging of BDF's for vinculin, alpha smooth muscle actin and F-actin revealed that cells cultured on ADM BM surfaces according to the invention contained better formed and abundant focal adhesions than cells cultured on the comparative smooth and textured implants; BDF's on ADM BM surfaces according to the invention displayed more phenotypic fibroblast morphology in comparison to BDF's on smooth and textured implants; SEM of BDF's on the different surfaces revealed that BDF's on ADM BM surfaces according to the invention were more spread and had a typical morphological appearance of fibroblasts. In comparison, BDF's on smooth implants were rounded.

These promising data indicate that biomimetic inspired breast implant surfaces, based on ADM BM topography, may have a potential clinical application of reducing the formation of capsular contracture and improving cellular response in general, when compared to smooth and textured implants, through improved cell-surface mediated foreign body reaction.

Specific nano-scale and micro-scale features have been shown to improve cell attachment, proliferation and migration. In addition, further downstream responses such as gene expression and cytokine release have been shown to be altered by nano and micro scale topographies. A surface such as ADM BM incorporates all of these features and is extremely effective at performing its roles, one of which is to promote cell attachment and migration of cells, particularly during wound healing and tissue regeneration. Thus, the biomimetic surface implants of the invention show great promise in stimulating a favourable inflammatory and tissue synthesis response in vivo.

ADM BM surface features include a range of sizes with micro and nanoscale features superimposed on top of the macroscale features. In morphological terms, it indicates the nano-topography of the BM on top of the more undulated and rough PD. This complete range of surface feature sizes is expected to confer beneficial properties to an implant through promoting initial cell adhesion and function whilst also encouraging tissue integration into the finely textured surface and prevention of capsular contracture.

The ADM BM surfaces produced by the casting method of the present invention while also containing features on the nano and sub-micron scale, which may influence cell adhesion and therefore all downstream functions, also contains larger features which are 10's of microns large which may begin to influence tissue integration. Thus, ADM BM surfaces according to the invention are likely to show in vivo influence on fibrous capsule formation at a cellular and tissue level. This cannot be said for either smooth or textured implants. Textured implants may be able to encourage tissue integration, implant stability and disruption of parallel collagen bundle formation but they are not able to influence cell response. Further, smooth implants appear to be unable to perform at either of these levels.

The present invention thus provides an extremely valuable contribution to the art in providing new biomimetic surfaces for incorporation generally in implants, particularly breast implants, which enable significantly improved profiles of cell attachment, proliferation, survival and expression of genes associated with cell attachment and proliferation compared to conventional prior art implant surface types, thus making the present surfaces excellent candidates for use in preventing adverse cellular responses to implants when placed in the body.

-oOo-

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

It will be understood that the invention has been described by way of example only and modifications may be made whilst remaining within the scope and the spirit of the invention.

REFERENCES

[Schulte, V. A. 2009] Schulte, V. A. et al., Biomacromolecules 2009; 10(10):2795-2801.
[van Kooten, T. G. 1998] van Kooten, T. G. et al. J Biomed Mater Res 1998; 43(1):1-14.
[Rompen, E. 2006] Rompen, E. et al. Clin Oral Implants Res 2006; 17(52):55-67.
[Barnsley, G. P. 2006] Barnsley, G. P. et al. Plast Reconstr Surg 2006; 117(7):2182-2190.
[Harvey, A. G. 2013] Harvey, A. G., Hill, E. W., Bayat, A. Expert Rev Med Devices 2013; 10(2):257-267.
[Mendonca, G. 2008] Mendonca, G. et al. Biomaterials 2008; 29(28):3822-3835.
[Barr, S. 2011] Barr S, Bayat A. *Aesthet Surg J* 2011; 31(1): 56-67.
[Barr, S. 2009] Barr, S., Hill, E. W., Bayat, A. Open access Journal of Plastic surgery, Current Implant Surface Technology: An Examination of Their Nanostructure and Their Influence on Fibroblast Alignment and Biocompatibility, Volume 9, 16 Jun. 2009.
[Davila, A. A. 2012] Davila, A. A. et al. Arch Plast Surg 2013; 40:19-27.
[Salzberg, C. A. 2012] Salzberg, C. A. et al. Journal of Plastic, Reconstructive & Aesthetic Surgery (2013) 66, 323-328.
[Liu, D. Z. 2013] Liu, D. Z. et al. Annals of Plastic Surgery, 2013, Volume 00, Number 00, pages 1-5.

[Shih, B. 2012] Shih B, Bayat A. Comparative genomic hybridisation analysis of keloid tissue in Caucasians suggests possible involvement of HLA-DRB5 in disease pathogenesis. Arch Dermatol Res. 2012; 304(3):241-9.

[Shih, B. 2010] Shih B, McGrouther D A, Bayat A. Identification of novel keloid biomarkers through profiling of tissue biopsies versus cell cultures in keloid margin specimens compared to adjacent normal skin. Eplasty. 2010; 10:e24.

[Syed 2011] Syed F, Ahmadi E, Iqbal S A, Singh S, McGrouther D A, Bayat A. Fibroblasts from the growing margin of keloid scars produce higher levels of collagen I and III compared with intralesional and extralesional sites: clinical implications for lesional site-directed therapy, Br J Dermatol. 2011; 164(1):83-96.

[Kyle 2013] Kyle D J T, Harvey A G, Shih B, Tan K T, Chaudhry I H, Bayat A. Identification of molecular phenotypic descriptors of breast capsular contracture formation using informatics analysis of the whole genome transcriptome. Wound Repair Regen. 2013; 21(5):762-9.

[Tan 2010] Tan K T, Wjeratne D, Shih B, Baildam A D, Bayat A. Tumour Necrosis Factor-α Expression Is Associated with Increased Severity of Periprosthetic Breast Capsular Contracture. Eur Surg Res. 2010; 45(3-4):327-332.

[D'Andrea 2007] D'Andrea F, Nicoletti G F, Grella E, Grella R, Siniscalco D, Fuccio C, et al. Modification of Cysteinyl Leukotriene Receptor Expression in Capsular Contracture: Preliminary Results. Ann Plast Surg. 2007; 58(2): 212-214.

ISO 25178-2: 2012(E).

The invention claimed is:

1. A breast implant comprising a textured surface having, at an area scale of 1 mm×1 mm:
a mean surface roughness Sa value of from 5 µm to 7 µm;
a root mean square height Sq value of from 5 µm to 10 µm;
a mean surface skewness Ssk value of from −0.4 to +0.4; and
a mean excess kurtosis value (Sku minus 3) of from −0.7 to +0.7;
wherein the surface comprises a biocompatible polymer.

2. The breast implant of claim 1, wherein a maximum peak height to trough depth Sz value of the surface at an area scale of 1 mm×1 mm ranges from 10 µm to 80 µm.

3. The breast implant of claim 1, wherein a maximum peak height to trough depth Sz value of the surface at an area scale of 1 mm×1 mm ranges from 10 µm to 80 µm.

4. The breast implant of claim 1, wherein the mean surface skewness Ssk value ranges from −0.3 to +0.3.

5. The breast implant of claim 1, wherein the mean excess kurtosis value (Sku minus 3) ranges from −0.5 to +0.5.

6. The breast implant of claim 1, wherein the biocompatible polymer comprises polydimethylsiloxane.

7. The breast implant of claim 1, wherein the surface has, at an area scale of 90 µm×90 µm, a mean surface roughness Sa value of from 0.1 µm to 5 µm.

8. A breast implant comprising a biocompatible polymer material that forms an outermost surface of the breast implant, wherein the surface is textured and has, at an area scale of 1 mm×1 mm:
a mean surface roughness Sa value of from 3 µm to 9 µm;
a root mean square height Sq value of from 5 µm to 10 µm;
a mean excess kurtosis value (Sku minus 3) of from −0.7 to +0.7; and
a maximum peak height to trough depth Sz value from 10 µm to 80 µm.

9. The breast implant of claim 8, wherein a ratio of average peak height to average trough depth of the surface ranges from 2:3 to 3:2.

10. The breast implant of claim 8, wherein the mean surface roughness Sa value ranges from 5 µm to 7 µm.

11. The breast implant of claim 8, wherein a mean surface skewness Ssk value of the surface ranges from −0.4 to +0.4.

12. The breast implant of claim 8, wherein the surface is an irregular textured surface.

13. The breast implant of claim 8, wherein the surface forms at least 90% of a total tissue-contacting surface of the breast implant.

14. The breast implant of claim 8, wherein the biocompatible polymer material is polydimethylsiloxane.

15. The breast implant of claim 8, wherein the surface has, at an area scale of 90 µm×90 µm, a mean surface roughness Sa value of from 0.1 µm to 5 µm.

16. A breast implant comprising a biocompatible polymer material that forms an outermost surface of the breast implant, wherein the surface is textured and has, at an area scale of 1 mm×1 mm:
a mean surface roughness Sa value of from 5 µm to 7 µm;
a root mean square height Sq value of from 4 µm to 15 µm;

a mean surface skewness Ssk value of from −0.4 to +0.4; and a mean excess kurtosis value (Sku minus 3) of from −0.7 to +0.7;

wherein the textured surface is an irregular textured surface.

17. The breast implant of claim 16, wherein the root mean square height Sq value ranges from 5 μm to 10 μm, and wherein the surface has a maximum peak height to trough depth Sz value from 10 μm to 80 μm at an area scale of 1 mm×1 mm.

18. The breast implant of claim 16, wherein a ratio of average peak height to average trough depth of the surface ranges from 2:3 to 3:2.

19. The breast implant of claim 16, wherein the surface has, at an area scale of 90 μm×90 μm, a mean surface roughness Sa value of from 0.1 μm to 5 μm.

20. The breast implant of claim 16, wherein the surface has, at an area scale of 90 μm×90 μm, a mean surface skewness Ssk value of −0.9 to +0.9 and a mean excess kurtosis value (Sku minus 3) of from −1.5 to +1.5.

\* \* \* \* \*